United States Patent
Chen et al.

(10) Patent No.: US 12,116,608 B2
(45) Date of Patent: Oct. 15, 2024

(54) EXTENDED METABOLISM METHODS FOR INCREASING AND EXTRACTING METABOLITES FROM ALGAE AND MICROORGANISMS

(71) Applicant: Synergraze Inc., Calgary (CA)

(72) Inventors: Jianwei Chen, Calgary (CA); Tamara Lee Loiselle, Calgary (CA)

(73) Assignee: Synergraze Inc., Calgary (CA)

( * ) Notice: Subject to any disclaimer, the term of this patent is extended or adjusted under 35 U.S.C. 154(b) by 0 days.

(21) Appl. No.: 18/496,409

(22) Filed: Oct. 27, 2023

(65) Prior Publication Data

US 2024/0060092 A1 Feb. 22, 2024

Related U.S. Application Data

(63) Continuation of application No. PCT/IB2023/057246, filed on Jul. 14, 2023.

(60) Provisional application No. 63/446,735, filed on Feb. 17, 2023, provisional application No. 63/389,259, filed on Jul. 14, 2022.

(51) Int. Cl.
*C12P 5/02* (2006.01)

(52) U.S. Cl.
CPC ...................... *C12P 5/02* (2013.01)

(58) Field of Classification Search
CPC ........................................................ C12P 5/02
See application file for complete search history.

(56) References Cited

FOREIGN PATENT DOCUMENTS

AU 2021102541 A4 7/2021
WO WO-2023212121 A2 * 11/2023

OTHER PUBLICATIONS

Thapa HR et al. Supplemental Information for Genetic and biochemical reconstitution of bromoform biosynthesis in Asparagopsis lends insights into seaweed ROS enzymology. ACS Chemical Biology. 2020. p. 1-40 (Year: 2020).*
Tieves F et al. Formate Oxidase from Aspergillus oryzae: One catalyst enables diverse H2O2 Dependent Biocatalytic Oxidation Reactions. 2019. Angew. Chem. Int. Ed. 58, 7873-7877. (Year: 2019).*
Magnusson M et al. Using oil immersion to deliver a naturally-derived, stable bromoform product from the red seaweed *Asparagopsis taxiformis*. 2020. Algal Research. 51. p. 1-7 (Year: 2020).*
Sigma Aldrich. Sodium formate. 2010. p. 1 (Year: 2010).*
Cameron, M. R., et al.; "Growth and slaughter traits of Boer x Spanish, Boer x Angora, and Spanish goats consuming a concentrate-based diet," J Anim Sci. (Jun. 2001); 79(6):1423-1430.
Carter J.N. et al.; "Reactivity of recombinant and mutant vanadium bromoperoxidase from the red alga *Corallina officinalis*," J Inorg Biochem. (2002); 91(1):59-69.
Claffey, N.A., et al.; "Effect of forage to concentrate ratio and duration of feeding on growth and feed conversion efficiency of male lambs," Transl Anim Sci. (Jun. 2018); 2(4):419-427.
International Search Report and Written Opinion for International Application No. PCT/IB2023/057246 dated Oct. 26, 2023, 10 pages.
Johnson, E.D., et al.; "Some effects of methane inhibition in ruminants (steers)," Can. J. Animal. Sci., (Dec. 1972), pp. 703-712.
Kinley, R., et al.; "In Vitro Evaluation of the Antimethanogenic Potency and Effects on Fermentation of Individual and Combinations of Marine Macroalgae," Am. J. Plant Sci., (Oct. 2016), 7(14):2038-2054.
Kinley, R.D. et al.; "Mitigating the carbon footprint and improving productivity of ruminant livestock agriculture using a red seaweed," Journal of Cleaner Production (2020); 259:120836, 10 pages.
Kinley, R.D. et al.; "The red macroalgae *Asparagopsis taxiformis* is a potent natural antimethanogenic that reduces methane production during in vitro fermentation with rumen fluid," Animal Production Science (2016); 56(3):282-289.
Lewis, S. J., et al., "Feedlot performance and carcass traits of Boer goat crosses and Spanish male kids [Abstract]," (1997) Journal of Animal Science, 75(Suppl. 1), p. 40.
Li, X. et al.; "Asparagopsis taxiformis decreases enteric methane production from sheep," Animal Production Science (2016), 58(4):681-688, 8 pages.
Li, X.Z., et al.; "Effects of dietary linseed oil and propionate precursors on ruminal microbial community, composition, and diversity in Yanbian yellow cattle," PLoS ONE (May 2015); 10(5):e0126473, 15 pages.
Liang, Y., et al.; "Effects of spirulina supplementation on lipid metabolism disorder, oxidative stress caused by high-energy dietary in Hu sheep," Meat Sci., (Jun. 2020); 164:108094, 9 pages.
Lin, C.Y. et al.; "Bromoform production from seawater treated with bromoperoxidase," Limnology and Oceanography (2012); 57(6):1857-1866.
Mtolera, M.S.P., et al.; "Stress-induced production of volatile halogenated organic compounds in Eucheuma denticulatum (Rhodophyta) caused by elevated pH and high light intensities," European Journal of Phycology (1996) 31(1):89-95, 8 pages.
Myers, E.W. et al.; "Optimal alignments in linear space," Comput Appl Biosci. (1988); 4(1):11-17.

(Continued)

*Primary Examiner* — Paul J Holland
(74) *Attorney, Agent, or Firm* — COOLEY LLP

(57) ABSTRACT

The present disclosure relates to methods and systems for extending metabolism of algal biomass or enzyme extracts, including the production and extraction of algal secondary metabolites with pharmaceutical, industrial, and agricultural uses. Aspects of this disclosure relate to production of antimethanogenic compounds from algae and other organisms. The disclosure further relates to compositions comprising antimethanogenic compounds and methods of using the same to reduce enteric methane emissions from ruminate animals. Methods of culturing algae in solutions with oil layers and triggering release of secondary metabolites through stress are also described.

16 Claims, 8 Drawing Sheets

Specification includes a Sequence Listing.

(56) References Cited

OTHER PUBLICATIONS

Roque, B.M. et al.; "Inclusion of Asparagopsis armata in lactating dairy cows' diet reduces enteric methane emission by over 50 percent," Journal of Cleaner Production (2019); 234:132-138.

Shike, D. W., "Beef cattle feed efficiency," [Conference session] (2013) Driftless Range Beef Conference, Dubuque, IA, United States. https://dr.lib.iastate.edu/entities/publication/dd175f9a-824e-4ac3-9b79-f56551ad8d13, 2 pages.

Shimonishi, M. et al.; "Cloning and expression of the gene for a vanadium-dependent bromoperoxidase from a marine macro-alga, *Corallina pilulifera*," FEBS Lett., (1998); 428(1-2):105-110.

Stender, D.R., "Swine feed efficiency: Influence of market weight," [Fact sheet] (2012), Iowa State University, 2 pages, https://dr.lib.iastate.edu/handle/20.500.12876/4997.

Thapa, H.R., et al.; "Genetic and Biochemical Reconstitution of Bromoform Biosynthesis in Asparagopsis Lends Insights into Seaweed Reactive Oxygen Species Enzymology," ACS Chemical Biology, Jun. 19, 2020, 15(6):1662-1670, 18 pages.

Wever, R. et al.; "Brominating activity of the seaweed *Ascophyllum nodosum*: Impact on the biosphere," Environ. Sci. Technol. (1991); 25(3):446-449.

Wood, J.M. et al.; "The reaction of multihalogenated hydrocarbons with free and bound reduced vitamin B 12," Biochemistry (May 1968); 7(5):1707-1713.

Zesiger, C., et al., "Market Animal Feed Efficiency: A Tool for Evaluating Feed Conversion," Utah State University Extension (2022) Paper 2269. https://digitalcommons.usu.edu/extension_curall/2269, [retrieved online Nov. 21, 2023], 4 pages.

\* cited by examiner

EXTENDED METABOLISM METHODS FOR INCREASING AND EXTRACTING METABOLITES FROM ALGAE AND MICROORGANISMS

This application is a continuation of International Application No. PCT/IB2023/057246 filed Jul. 14, 2023, which claims the benefit of U.S. Provisional Application No. 63/389,259 filed on Jul. 14, 2022, and U.S. Provisional Application No. 63/446,735 filed on Feb. 17, 2023, both of which are hereby incorporated by reference in their entirety for all purposes.

FIELD

The present disclosure relates to methods for producing and extracting metabolites (including antimethanogenic compounds such as bromoform) from algae and microorganisms. The disclosure further relates to compositions comprising antimethanogenic compounds and methods of using the same to reduce enteric methane emissions from ruminate animals.

DESCRIPTION OF THE TEXT FILE SUBMITTED ELECTRONICALLY

The contents of the text file submitted electronically herewith are incorporated herein by reference in their entirety: The sequence listing details are as follows: SNGZ_001_02WO_SeqList_ST26.xml; Size: 82,017 bytes; and Date of Creation: Jul. 14, 2023.

BACKGROUND

Both microalgae and macroalgae are known to produce secondary metabolites (e.g. bioactives, antimethanogenic compounds) that are of commercial value and that are used in the cosmetic, pharmaceutical, and agricultural industries. These metabolites include antioxidants, anti-bacterial, anti-viral, anti-cancer compounds, and methanogenesis inhibitors (also known as antimethanogenic compounds).

Ruminate animals produce and expel methane as part of their digestive process, specifically during the fermentation of undigested food in the rumen. However, methane is a greenhouse gas that is contributing to global warming. In terms of its potency, methane is 28-times more powerful than $CO_2$ on a 100-year timescale and 80-times more powerful over a 20-year timescale for altering earth's climate.

37% of methane emissions from human activity are the direct result of our livestock and agricultural practices. A single cow can produce between 154 and 264 pounds of methane gas per year; combined, methane emissions from cattle raised specifically for meat production emit at least 231 billion pounds of methane into the atmosphere each year (Agriculture and Aquaculture: Food for Thought, October 2020, available on the world wide web at epa.gov/snep/agriculture-and-aquaculture-food-thought).

Both microalgae and macroalgae are known to produce metabolites (for example halogenated compounds) that inhibit enteric methane production. An example of one such metabolite is bromoform ($CHBR_3$). Bromoform is a halogenated methane that is naturally produced by many types of algae, such as those belonging to the genus *Asparagopsis*. Algae that are known to naturally produce bromoform have an enzyme (bromoperoxidase) that catalyzes the formation of bromoform.

Bromoform is known to be an inhibitor of methanogenesis in ruminant animals, and studies have been conducted on reducing methane production in ruminant animals by including trace amounts of bromoform with their feed. Specifically, halogenated aliphatic compounds with 1 or 2 carbons such as bromoform block the function of corrinoid enzymes and inhibit cobamide-dependent methyl group transfer in methanogenesis (Wood J. et al., Reaction of multihalogenated volatile fatty acids with free and bound reduced vitamin B12, *Biochem.* 7 (1968) pp. 1707-13. See also Roque B. M. et al., Inclusion of *Asparagopsis armata* in lactating dairy cows' diet reduces enteric methane emission by over 50 percent, *J. Clean. Prod.*, 234 (2019) pp. 132-138; Kinley R. D. et al., The red macroalgae *Asparagopsis taxiformis* is a potent natural antimethanogenic that reduces methane production during in vitro fermentation with rumen fluid, *Anim. Prod. Sci.*, 56 (2016), pp. 282-289; Li X. et al., *Asparagopsis taxiformis* decreases enteric methane production from sheep, *Anim. Prod. Sci.*, 58 (2018), pp. 681-688; and Kinley R. D. et al., Mitigating the carbon footprint and improving productivity of ruminant livestock agriculture using a red seaweed, *J. of Cleaner Prod.* 259 (2020).

Currently, one conventional way of including bromoform into animal feed is to collect and freeze-dry algae that are known to naturally produce antimethanogenic compounds (such as those of the genus *Asparagopsis*) and to introduce the freeze-dried algae into the feed. However, algae such as *Asparagopsis* spp. may contain malodorous components. These odor triggering components reduce the palatability of the feed that has been supplemented with compositions derived from algal biomass. Additionally, freeze-drying algae is not cost-effective, and the product has a relatively short shelf-life.

Thus there is a need for more efficient methods for increasing and extracting metabolites from algae, or using alternative algal species apart from *Asparagopsis* to produce methane-inhibiting metabolites for use in applications such as in animal feed.

SUMMARY OF THE DISCLOSURE

In one aspect, the disclosure teaches a method for producing a secondary metabolite in algae, the method comprising the steps of providing an algal biomass; providing a reaction solution, the reaction solution comprising a volatile fatty acid, hydrogen peroxide, and a halide; and contacting the algal biomass with the reaction solution for a time period sufficient to synthesize the secondary metabolite, wherein the algal biomass in the reaction solution produces higher quantities of the secondary metabolite than a comparable algal biomass without the reaction solution.

In another aspect, the disclosure teaches a method for producing a secondary metabolite in algae, the method comprising the steps of providing a haloperoxidase enzyme; providing a reaction solution, the reaction solution comprising a volatile fatty acid, hydrogen peroxide, and a halide; and contacting the peroxidase enzyme with the reaction solution for a time period sufficient to synthesize a secondary metabolite.

In another aspect, the disclosure relates to a composition comprising an algal biomass; a reaction solution, the reaction solution comprising a volatile fatty acid, hydrogen peroxide, and a halide; and a secondary metabolite.

In another aspect, the disclosure relates to an algal cultivation system comprising an algal biomass; an algal growth substrate; and an oil layer. In some embodiments, the algal growth substrate comprises an osmotic regulator, a carbon source, and nutrient mix. In some embodiments, the algal cultivation system comprises a reaction solution, the reaction solution comprising a volatile fatty acid, hydrogen peroxide, and a halide.

In another aspect, the disclosure teaches a method for extracting or inducing release of a secondary metabolite from algae, the method comprising the steps of providing an algal biomass; and exposing said algal biomass to an environmental stress, wherein said environmental stress induces the algae to release the secondary metabolite, thereby allowing extraction of the secondary metabolite.

The foregoing was intended as a summary only and of only some of the aspects of the disclosure. It was not intended to define the limits or requirements of the disclosure. Other aspects of the disclosure will be appreciated by reference to the detailed description of the embodiments.

BRIEF DESCRIPTION OF THE DRAWINGS

The preferred embodiment of the disclosure will be described by reference to the drawings thereof, in which.

DETAILED DESCRIPTION

Definitions

Figure 1:
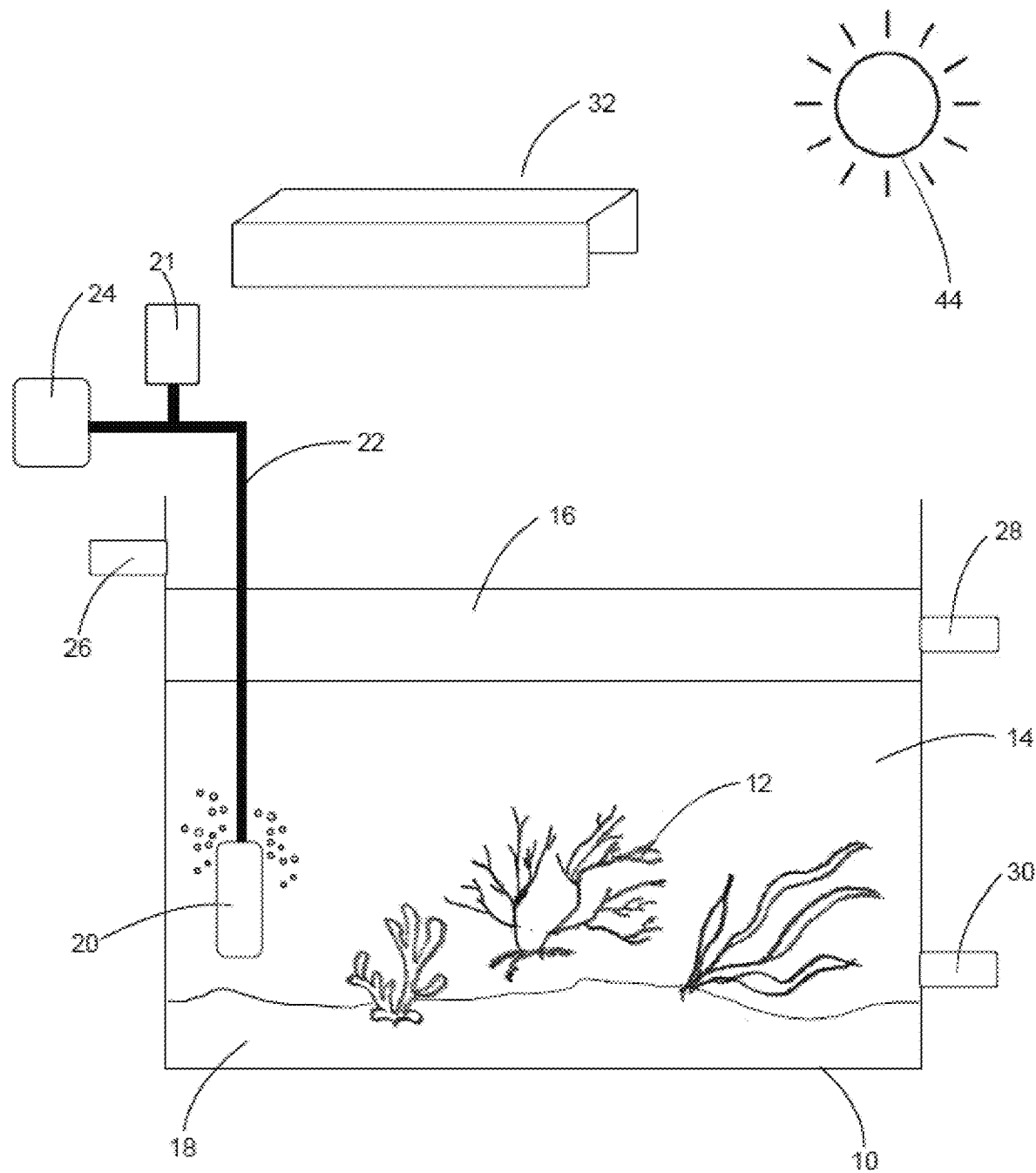
FIG. 1 is a diagram of a vessel for carrying out methods of the present disclosure.

In the description and tables which follow, a number of terms are used. In order to provide a clear and consistent understanding of the specification and claims, including the scope to be given such terms, the following definitions are provided.

The term "a" or "an" refers to one or more of that entity; for example, "a primer" refers to one or more primers or at least one primer. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The term "about" when immediately preceding a numerical value means a range (e.g., plus or minus 10% of that value). For example, "about 50" can mean 45 to 55, "about 25,000" can mean 22,500 to 27,500, etc., unless such an interpretation would result in a value above or below range of possible values, such as below 0% or above 100% of a possible value. Furthermore, the phrases "less than about" a value or "greater than about" a value should be understood in view of the definition of the term "about" provided herein, as applied to any recited endpoint. Similarly, the term "about" when preceding a series of numerical values or a range of values (e.g., "about 10, 20, 30" or "about 10-30") refers, respectively to all values in the series, or the endpoints of the range.

The term "approximately" when immediately preceding a numerical value means a range (e.g., plus or minus 5% of that value). For example, "approximately 50" can mean 47.5 to 52.5, "approximately 25,000" can mean 23,750 to 26,250, etc., unless such an interpretation would result in a value above or below range of possible values, such as below 0% or above 100% of a possible value.

The term "antimethanogenic compound" or "anti-methanogenic compound" refers to any compound that inhibits methanogenesis in a ruminant.

The terms "bioactives" and "metabolites" may be used interchangeably to refer to compounds formed through metabolic activity by algae.

"Bioproduct" as used herein refers to any product produced from or derived from a renewable biological resource.

As used herein, "fresh algae" refers to algae that is alive and has never been frozen.

As used herein, "full spectrum" refers to a composition that retains the complex profile of naturally occurring compounds formed through metabolic activity by algae. For example, in some embodiments, a full spectrum composition from an algal biomass includes the antimethanogenic compound and vitamin B12 produced by the algae.

The terms "microorganism" and "microbe" mean any microscopic unicellular organism and can include bacteria, microalgae, yeast, or fungi.

As used herein, "recombinant" refers to DNA, proteins, cells, or organisms that are man-made by combining genetic material from two different sources. As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by Clustal Omega® using default parameters.

As used herein, a residue (such as a nucleic acid residue or an amino acid residue) in sequence "X" is referred to as corresponding to a position or residue (such as a nucleic acid residue or an amino acid residue) "a" in a different sequence "Y" when the residue in sequence "X" is at the counterpart position of "a" in sequence "Y" when sequences X and Y are aligned using amino acid sequence alignment tools known in the art, such as, for example, Clustal Omega or BLAST®.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988). Similarity is more sensitive measure of relatedness between sequences than identity; it takes into account not only identical (i.e. 100% conserved) residues but also non-identical yet similar (in size, charge, etc.) residues. % similarity is a little tricky since its exact numerical value depends on parameters such as substitution matrix one uses (e.g. permissive BLOSUM45 vs. stringent BLOSUM90) to estimate it.

"W/W" or "w/w", in reference to proportions by weight, refers to the ratio of the weight of one substance in a composition to the weight of the composition.

Overview

The present disclosure relates to extended metabolism methods and systems for producing and extracting antimethanogenic compounds from microorganisms and algae. The disclosure further relates to compositions comprising antimethanogenic compounds and methods of using the same to reduce enteric methane emissions from ruminate animals.

Secondary Metabolites Produced by Algae

Macroalgae, such as seaweed, and microalgae produce a wide range of secondary metabolites that can be used for any number of purposes. Among these are volatile halogenated organic compounds (VHOCs) which can be used as anti-methanogenic compounds to inhibit microbial methanogenesis, the anaerobic respiration that reduces carbon dioxide ($CO_2$) to methane ($CH_4$). These algae produce various peroxidases, which react with hydrogen peroxide and organic matter to form VHOCs. As an example, in species of *Asparagopsis*, a peroxidase catalyzes the conversion of halide anions (i.e. Br-) to hypohalous acid (i.e. HOBr) with hydrogen peroxide acting as the oxidizing agent.

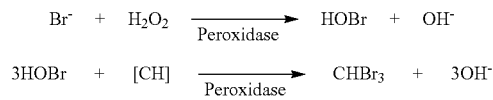

The resulting hypohalous acid (e.g. HOBr) is not stable and will react with selective substrates to form, for example, bromoform and other brominated compounds, such as dibromochloromethane (shown below). As discussed in more detail in later sections of this document, corresponding structures also form when other halides are used in the reaction.

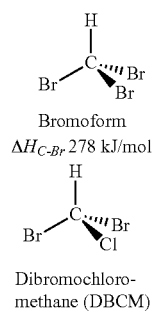

Examples of VHOCs include, but are not limited to, methyl halides —$CH_3Br$, $CH_3Cl$, $CH_3I$, $CH_3F$, bromodichlormethane ($CHBrCl_2$), trichlorethylene ($C_2HCl_3$), bromoform ($CHBr_3$), chloroform ($CHCl_3$), iodoform (CHIS), fluoroform ($CHF_3$), and dibromomethane ($CH_2Br_2$).

Bromoform ($CHBr_3$)

Bromoform is colorless to pale yellow, with a sweet odor. It is denser than water, and soluble in water. Bromoform is the most abundant VHOC produced by seaweeds of the genus *Asparagopsis*, but it is also produced by, for example, other red seaweeds (e.g. *Chondrus crispus, Gigartina stellata*), brown seaweeds (e.g. *Ascophyllum nodosum, Fucus vesiculosis Macrocystis pyrifera*) green seaweeds (e.g. *Enteromorpha linza, Ulva lacta*), blue green algae, microalgae, and phytoplankton.

Bromoperoxidases within these species act on hydrogen peroxide and bromide to produce hypohalous acid (HOBr). Previous studies have shown that the bromoperoxidases within these organisms are able to act on exogenously supplied hydrogen peroxide and bromide (Wever R. et al., Brominating activity of the seaweed *Ascophyllum nodosum*: Impact on the biosphere, *Environ. Sci. Technol.* 1991, 25, 446-449, hereinafter "Wever"). Wever found that, when 2 mM $H_2O_2$ and 100 mM bromide were added to *A. nodosum* tissue, the rate of HOBr formation greatly accelerated. At the time of the Wever publication, the biosynthetic pathway that forms $CHBr_3$ was not known, but Wever hypothesized that HOBr was released in seawater and reacted with dissolved organic compounds to form $CHBr_3$.

Subsequent studies reported that bromoform production is higher in seaweed nearshore versus offshore, possibly due to higher organic matter runoff (e.g. fulvic and humic), thus concurring with Weyer's hypothesis (Lin C. Y., Manley S. L. (2012) Bromoform production from seawater treated with bromoperoxidase. *Limnol. Oceanogr.* 57 (6), 1857-1866).

More recently it's been proposed that the substrate employed by *Asparagopsis* for bromoform production is endogenously produced, as opposed to the exogenous dissolved organic matter proposed by Wever and Lin et al. 2012 (Thapa H. R. et al. Genetic and Biochemical Reconstitution of Bromoform Biosynthesis in *Asparagopsis* Lends Insights into Seaweed Reactive Oxygen Species Enzymology, *ACS Chem. Biol.* 2020 15, 1662-1670 (hereinafter "Thapa")). Thapa found that bromoform could be produced via fatty acid biosynthesis, using the organic compounds 5 (pentane-2,4-dione) or 6 (heptane 2,4,6-trione), but did not provide comparative yield data. Thus, to this day, little is known about the substrates for required for commercial-level bromoform production.

If secondary metabolites are to be used on a larger scale to mitigate the production of methane in ruminants and have an impact on climate change, more efficient and prolific methods are needed to increase metabolite concentrations.

Methods of Extending Metabolism and Producing Secondary Metabolites

Utilizing Algal Biomass to Produce Secondary Metabolites

The present disclosure teaches an extended metabolism method for producing a secondary metabolite in algae, the method comprising the steps of providing an algal biomass; providing a reaction solution, the reaction solution comprising a volatile fatty acid, hydrogen peroxide, and a halide, and contacting the algal biomass with the reaction solution for a time period sufficient to synthesize the secondary metabolite, wherein the algal biomass in the reaction solution produces higher quantities of the secondary metabolite than a comparable algal biomass without the reaction solution.

In accordance with one embodiment of the disclosure, a method for producing a secondary metabolite from algae (FIG. 1) comprises combining a biomass 12 of algae with a mixture comprising a reaction solution 14. The reaction solution 14 comprises substrates required for extended metabolism to produce secondary metabolites, including antimethanogenic compounds such as bromoform. For example, the substrates may include hydrogen peroxide, volatile fatty acids (VFAs) such as an acetate compound or a formate compound, and halide compounds. In one embodiment, the reaction solution 14 comprises hydrogen peroxide, sodium acetate and/or sodium formate, and sodium bromide, although other suitable compounds may also be used. In some embodiments, the concentration of bromide, such as sodium bromide, is between 2.4 mM and 120 mM. In some embodiments, the concentration of volatile fatty acids, such as sodium formate and/or sodium acetate is between 1 and 40 mM. In some embodiments the hydrogen peroxide in the reaction solution is at 1-1,000 mM.

Higher concentrations of bromide, acetate and/or formate have not been found to have deleterious effect on the reactions. However, substantially higher concentrations of hydrogen peroxide can have negative effects on the reaction due to damage of the algal biomass.

TABLE 1

Illustrative Reaction solution

| Ingredient | Amount |
| --- | --- |
| Volatile fatty acid (e.g., formate) | At least 1 mM Between 1 mM and 40 mM |
| Halide (e.g., Bromide ion) | At least 1 mM Between 2.4 mM and 120 mM |
| Optional Buffer | To maintain pH of between 5.0 and 11.0 |
| Hydrogen peroxide | At least 1 mM Between 2 mM and 450 mM |

The haloperoxidases from the biomass will act to catalyze the halogenation of organic compounds in the presence of halide ions and peroxides, such as $H_2O_2$. However, they can also carry out halogenation, sulfoxidation, epoxidation, and oxidation reactions. The resulting products (such as HOBr in the example reaction above) will react with the other substrates (such as volatile fatty acids) in the reaction solution in an extension of the algae's metabolism, resulting in production of secondary metabolites, including antimethanogenic compounds. In some embodiments, the secondary metabolite is a methyl halide. In some embodiments, the secondary metabolite is an antimethanogenic compound. In some embodiments, the secondary metabolite is a VHOC. In some embodiments, the secondary metabolite is selected from methyl bromide, methyl chloride, methyl iodide, methyl fluoride, bromodichlormethane, trichlorethylene, bromoform, chloroform, iodoform, fluoroform, dibromomethane, and combinations thereof.

Persons having skill in the art will recognize that the algal biomass can be contacted with any amount of reaction solution. In some embodiments however, it may be cost effective to utilize less reaction solution. Thus, in some embodiments, the ratio of algal biomass to reaction solution is between approximately 1:1 and 1:50 by weight (w/w). In some embodiments, the ratio of algal biomass to reaction solution is approximately 1:2, approximately 1:3, approximately 1:4, approximately 1:5, approximately 1:6, approximately 1:7, approximately 1:8, approximately 1:9, approximately 1:10, approximately 1:11, approximately 1:12, approximately 1:13, approximately 1:14, approximately 1:15, approximately 1:16, approximately 1:17, approximately 1:18, approximately 1:19, approximately 1:20, approximately 1:21, approximately 1:22, approximately 1:23, approximately 1:24, approximately 1:25, approximately 1:26, approximately 1:27, approximately 1:28, approximately 1:29, approximately 1:30, approximately 1:31, approximately 1:32, approximately 1:33, approximately 1:34, approximately 1:35, approximately 1:36, approximately 1:37, approximately 1:38, approximately 1:39, approximately 1:40, approximately 1:41, approximately 1:42, approximately 1:43, approximately 1:44, approximately 1:45, approximately 1:46, approximately 1:47, approximately 1:48, approximately 1:49, or approximately 1:50 by weight, including all ranges and subranges therebetween. in some embodiments, the ratio of algal biomass to reaction solution is between approximately 1:2 and 1:4 by weight (w/w).

Reaction Solutions

In some embodiments, the reaction solution used with the algal biomass or the haloperoxidase enzyme comprises bromide. Persons having skill in the art however, will recognize that other halides can also be processed and incorporated into different secondary metabolite products, such as antimethanogenic compounds.

Thus, in some embodiments, the reaction solution comprises at least one of a chloride, a fluoride, an iodide, a fluoride, or combinations thereof. In some embodiments, the reaction solution comprises astatine. In some embodiments, the bromide is a bromide-ion. In some embodiments, the bromide is sodium bromide, potassium bromide, calcium bromide, magnesium bromide, ammonium bromide, silver bromide, lead(II) bromide, Iron(III) bromide, Zinc bromide, Copper(II) bromide, or combinations thereof.

In some embodiments, the reaction solution comprises at least 1 mM bromide. In some embodiments, the reaction solution comprises at least 1 mM, at least 1.1 mM, at least 1.2 mM, at least 1.3 mM, at least 1.4, mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.1 mM, at least 3.2 mM, at least 3.3 mM, at least 3.5 mM, at least 3.6 mM, at least 3.7 mM, at least 3.8 mM, at least 3.9 mM, at least 4.0 mM, at least 4.1 mM, at least 4.2 mM, at least 4.3 mM, at least 4.4 mM, at least 4.5 mM, at least 4.6 mM, at least 4.7 mM, at least 4.8 mM, at least 4.9 mM, at least 5.0 mM, at least 5.1 mM, at least 5.2 mM, at least 5.3 mM, at least 5.4 mM, at least 5.5 mM, at least 5.6 mM, at least 5.7 mM, at least 5.8 mM, at least 5.9 mM, at least 6.0 mM, at least 6.1 mM, at least 6.2 mM, at least 6.3 mM, at least 6.4 mM, at least 6.5 mM, at least 6.6 mM, at least 6.7 mM, at least 6.8 mM, at least 6.9 mM, at least 7.0 mM, at least 7.1 mM, at least 7.2 mM, at least 7.3 mM, at least 7.4 mM, at least 7.5 mM, at least 7.6 mM, at least 7.7 mM, at least 7.8 mM, at least 7.9 mM, at least 8.0 mM, at least 8.1 mM, at least 8.2 mM, at least 8.3 mM, at least 8.4 mM, at least 8.5 mM, at least 8.6 mM, at least 8.7 mM, at least 8.8 mM, at least 8.9 mM, at least 9.0 mM, at least 9.1 mM, at least 9.2 mM, at least 9.3 mM, at least 9.4 mM, at least 9.5 mM, at least 9.6 mM, at least 9.7 mM, at least 9.8 mM, at least 9.9 mM, or at least 10 mM bromide, including all ranges and subranges therebetween.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM bromide, including all ranges and subranges therebetween.

In some embodiments, the iodide is an iodide-ion. In some embodiments, the iodide is sodium iodide, potassium iodide, ammonium iodide, silver iodide, lead iodide, mercury iodide, calcium iodide, zinc iodide, barium iodide and/or copper iodide. In some embodiments, the reaction solution comprises at least 1 mM iodide. In some embodiments, the reaction solution comprises at least 1 mM, at least 1.1 mM, at least 1.2 mM, at least 1.3 mM, at least 1.4, mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.1 mM, at least 3.2 mM, at least 3.3 mM, at least 3.5 mM, at least 3.6 mM, at least 3.7 mM, at least 3.8 mM, at least 3.9 mM, at least 4.0 mM, at least 4.1 mM, at least 4.2 mM, at least 4.3 mM, at least 4.4 mM, at least 4.5 mM, at least 4.6 mM, at least 4.7 mM, at least 4.8 mM, at least 4.9 mM, at least 5.0 mM, at least 5.1 mM, at least 5.2 mM, at least 5.3 mM, at least 5.4 mM, at least 5.5 mM, at least 5.6 mM, at least 5.7 mM, at least 5.8 mM, at least 5.9 mM, at least 6.0 mM, at least 6.1 mM, at least 6.2 mM, at least 6.3 mM, at least 6.4 mM, at least 6.5 mM, at least 6.6 mM, at least 6.7 mM, at least 6.8 mM, at least 6.9 mM, at least 7.0 mM, at least 7.1 mM, at least 7.2 mM, at least 7.3 mM, at least 7.4 mM, at least 7.5 mM, at least 7.6 mM, at least 7.7 mM, at least 7.8 mM, at least 7.9 mM, at least 8.0 mM, at least 8.1 mM, at least 8.2 mM, at least 8.3 mM, at least 8.4 mM, at least 8.5 mM, at least 8.6 mM, at least 8.7 mM, at least 8.8 mM, at least 8.9 mM, at least 9.0 mM, at least 9.1 mM, at least 9.2 mM, at least 9.3 mM, at least 9.4 mM, at least 9.5 mM, at least 9.6 mM, at least 9.7 mM, at least 9.8 mM, at least 9.9 mM, or at least 10 mM iodide, including all ranges and subranges therebetween.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM iodide, including all ranges and subranges therebetween.

In some embodiments, the chloride is a chloride-ion. In some embodiments, the chloride is sodium chloride, potassium chloride, calcium chloride, magnesium chloride, iron (iii) chloride, copper(II) chloride, zinc chloride, ammonium chloride, silver chloride, lead(ii) chloride, or combinations thereof. In some embodiments, the reaction solution comprises at least 1 mM chloride. In some embodiments, the reaction solution comprises at least 1 mM, at least 1.1 mM, at least 1.2 mM, at least 1.3 mM, at least 1.4, mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.1 mM, at least 3.2 mM, at least 3.3 mM, at least 3.5 mM, at least 3.6 mM, at least 3.7 mM, at least 3.8 mM, at least 3.9 mM, at least 4.0 mM, at least 4.1 mM, at least 4.2 mM, at least 4.3 mM, at least 4.4 mM, at least 4.5 mM, at least 4.6 mM, at least 4.7 mM, at least 4.8 mM, at least 4.9 mM, at least 5.0 mM, at least 5.1 mM, at least 5.2 mM, at least 5.3 mM, at least 5.4 mM, at least 5.5 mM, at least 5.6 mM, at least 5.7 mM, at least 5.8 mM, at least 5.9 mM, at least 6.0 mM, at least 6.1 mM, at least 6.2 mM, at least 6.3 mM, at least 6.4 mM, at least 6.5 mM, at least 6.6 mM, at least 6.7 mM, at least 6.8 mM, at least 6.9 mM, at least 7.0 mM, at least 7.1 mM, at least 7.2 mM, at least 7.3 mM, at least 7.4 mM, at least 7.5 mM, at least 7.6 mM, at least 7.7 mM, at least 7.8 mM, at least 7.9 mM, at least 8.0 mM, at least 8.1 mM, at least 8.2 mM, at least 8.3 mM, at least 8.4 mM, at least 8.5 mM, at least 8.6 mM, at least 8.7 mM, at least 8.8 mM, at least 8.9 mM, at least 9.0 mM, at least 9.1 mM, at least 9.2 mM, at least 9.3 mM, at least 9.4 mM, at least 9.5 mM, at least 9.6 mM, at least 9.7 mM, at least 9.8 mM, at least 9.9 mM, or at least 10 mM chloride, including all ranges and subranges therebetween.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM chloride, including all ranges and subranges therebetween.

In some embodiments, the fluoride is a fluoride-ion. In some embodiments, the fluoride is sodium fluoride, potassium fluoride, calcium fluoride, ammonium fluoride, lithium fluoride, aluminum fluoride, lithium fluoride, ammonium fluoride, silver fluoride, lead(II) fluoride, zinc fluoride, iron (III) fluoride, or combinations thereof. In some embodiments, the reaction solution comprises at least 1 mM fluoride. In some embodiments, the reaction solution comprises at least 1 mM, at least 1.1 mM, at least 1.2 mM, at least 1.3 mM, at least 1.4, mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.1 mM, at least 3.2 mM, at least 3.3 mM, at least 3.5 mM, at least 3.6 mM, at least 3.7 mM, at least 3.8 mM, at least 3.9 mM, at least 4.0 mM, at least 4.1 mM, at least 4.2 mM, at least 4.3 mM, at least 4.4 mM, at least 4.5 mM, at least 4.6 mM, at least 4.7 mM, at least 4.8 mM, at least 4.9 mM, at least 5.0 mM, at least 5.1 mM, at least 5.2 mM, at least 5.3 mM, at least 5.4 mM, at least 5.5 mM, at least 5.6 mM, at least 5.7 mM, at least 5.8 mM, at least 5.9 mM, at least 6.0 mM, at least 6.1 mM, at least 6.2 mM, at least 6.3 mM, at least 6.4 mM, at least 6.5 mM, at least 6.6 mM, at least 6.7 mM, at least 6.8 mM, at least 6.9 mM, at least 7.0 mM, at least 7.1 mM, at least 7.2 mM, at least 7.3 mM, at least 7.4 mM, at least 7.5 mM, at least 7.6 mM, at least 7.7 mM, at least 7.8 mM, at least 7.9 mM, at least 8.0 mM, at least 8.1 mM, at least 8.2 mM, at least 8.3 mM, at least 8.4 mM, at least 8.5 mM, at least 8.6 mM, at least 8.7 mM, at least 8.8 mM, at least 8.9 mM, at least 9.0 mM, at least 9.1 mM, at least 9.2 mM, at least 9.3 mM, at least 9.4 mM, at least 9.5 mM, at least 9.6 mM, at least 9.7 mM, at least 9.8 mM, at least 9.9 mM, or at least 10 mM fluoride, including all ranges and subranges therebetween.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM fluoride, including all ranges and subranges therebetween.

In some embodiments, the volatile fatty acid comprises acetate. In some embodiments, the acetate is selected from the group consisting of, sodium acetate, potassium acetate, aluminum acetate, and ammonium acetate. In some embodiments, the acetate is sodium acetate or potassium acetate. In some embodiments, the acetate is sodium acetate.

In some embodiments, the reaction solution comprises at least 1 mM acetate. In some embodiments, the reaction solution comprises at least 2 mM, at least 3 mM, at least 4 mM, at least 5, mM, at least 6 mM, at least 7 mM, at least 8 mM, at least 9 mM, or at least 10 mM acetate, including all ranges and subranges therebetween. In some embodiments, the reaction solution comprises between about 1 mM and 40 mM acetate. In some embodiments, the reaction solution comprises between 1 mM and 5 mM, between 5 mM and 10 mM, between 10 mM and 15 mM, between 15 mM and 20 mM, between 20 mM and 25 mM, between 25 mM and 30 mM, between 30 mM and 35 mM, between 35 mM and 40 mM acetate.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM acetate, including all ranges and subranges therebetween.

In some embodiments, the reaction solution comprises at least 1 mM acetone. In some embodiments, the reaction solution comprises at least 2 mM, at least 3 mM, at least 4 mM, at least 5, mM, at least 6 mM, at least 7 mM, at least 8 mM, at least 9 mM, or at least 10 mM acetone, including all ranges and subranges therebetween.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM acetone, including all ranges and subranges therebetween.

In some embodiments, the volatile fatty acid comprises formate. In some embodiments, the formate is sodium formate or potassium formate. In some embodiments, the reaction solution comprises at least 1 mM formate. In some embodiments, the reaction solution comprises at least 1 mM, at least 1.1 mM, at least 1.2 mM, at least 1.3 mM, at least 1.4, mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.1 mM, at least 3.2 mM, at least 3.3 mM, at least 3.5 mM, at least 3.6 mM, at least 3.7 mM, at least 3.8 mM, at least 3.9 mM, at least 4.0 mM, at least 4.1 mM, at least 4.2 mM, at least 4.3 mM, at least 4.4 mM, at least 4.5 mM, at least 4.6 mM, at least 4.7 mM, at least 4.8 mM, at least 4.9 mM, at least 5.0 mM, at least 5.1 mM, at least 5.2 mM, at least 5.3 mM, at least 5.4 mM, at least 5.5 mM, at least 5.6 mM, at least 5.7 mM, at least 5.8 mM, at least 5.9 mM, at least 6.0 mM, at least 6.1 mM, at least 6.2 mM, at least 6.3 mM, at least 6.4 mM, at least 6.5 mM, at least 6.6 mM, at least 6.7 mM, at least 6.8 mM, at least 6.9 mM, at least 7.0 mM, at least 7.1 mM, at least 7.2 mM, at least 7.3 mM, at least 7.4 mM, at least 7.5 mM, at least 7.6 mM, at least 7.7 mM, at least 7.8 mM, at least 7.9 mM, at least 8.0 mM, at least 8.1 mM, at least 8.2 mM, at least 8.3 mM, at least 8.4 mM, at least 8.5 mM, at least 8.6 mM, at least 8.7 mM, at least 8.8 mM, at least 8.9 mM, at least 9.0 mM, at least 9.1 mM, at least 9.2 mM, at least 9.3 mM, at least 9.4 mM, at least 9.5 mM, at least 9.6 mM, at least 9.7 mM, at least 9.8 mM, at least 9.9 mM, or at least 10 mM formate, including all ranges and subranges therebetween.

In some embodiments, the reaction solution comprises between 2.4 mM and 120 mM formate. In some embodiments, the reaction solution comprises between 1 mM and 40 mM formate. In some embodiments, the reaction solution comprises between 1 mM and 5 mM, between 5 mM and 10 mM, between 10 mM and 15 mM, between 15 mM and 20 mM, between 20 mM and 25 mM, between 25 mM and 30 mM, between 30 mM and 35 mM, between 35 mM and 40 mM formate.

In some embodiments, the reaction solution comprises between 40 mM and 45 mM, between 45 mM and 50 mM, between 50 mM and 55 mM, between 55 mM and 60 mM, between 60 mM and 65 mM, between 65 mM and 70 mM, between 70 mM and 75 mM, between 75 mM and 80 mM, between 80 mM and 85 mM, between 85 mM and 90 mM, between 90 mM and 95 mM, between 95 mM and 100 mM, between 100 mM and 105 mM, between 105 mM and 110 mM, between 110 mM and 115 mM, between 115 mM and 120 mM formate.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM formate, including all ranges and subranges therebetween.

In some embodiments, the volatile fatty acid comprises acetate and/or formate. In some embodiments, the reaction solution comprises any of the following substrates instead of, or as the VFA: methanol, formaldehyde, formic acid, urine, ethanol, acetaldehyde, acetic acid, glycolic acid, ethylene glycol, glyoxal, oxalic acid, methoxymethane, methyl formate, 1-Propanol, Isopropanol, Propylene glycol, 1,3-propanediol, Glycerin, Propionaldehyde, Malondialdehyde, malonic acid, pyruvic acid, Mesoxalic acid, Tartronic acid, Methoxyethane, 2-Methoxyethanol, Ethyl formate, methyl acetate, Butanol, Isobutanol, tert-Butanol, 2-Butanol, 1,2-Butanediol, 1,3-Butane diol, 1,4-Butanediol, 2,3-Butane diol, 2-Methyl-1,2-propanediol, 2-Methyl-1,3-propanediol, 2-Methyl-2,4-pentanediol, 1,2,3-Butanetri ol, 1,2,4-Butanetriol, 1,3,4-Butanetriol, Erythritol, Butyraldehyde, Succinaldehyde, Isobutyraldehyde, Methyl Ethyl Ketone, Diacetyl, α-Ketobutyric acid, butyric acid, Isobutyric acid, Acetoacetic acid, 4-oxobutanoate, 3-Hydroxy3-formyl propanoic acid, 3-oxobutanoic acid, Succinic Acid, Maleic acid, Fumaric acid, Methoxypropane, Diethyl ether, Methyl propionate, Dimethyl malonate, propyl formate, isopropyl formate, butyl formate, methyl butyrate, ethyl acetate, dimethyl oxalate, Acetonedicarboxylic acid, Glucose, Fructose, Sucrose, Lactose, Maltose, Galactose, Ribose, Xylose, Mannose, sobutyric acid, Valeric acid, Isovaleric acid, Caproic acid, Caprylic acid, Capric acid, Lauric acid, Lactic acid, Citric acid, Pyruvate, Succinate, Oxaloacetate, α-Ketoglutaric acid, Fumarate, Malate, Glutamate, Dimethyl sulfoxide, Sorbitol, Gluconic acid, Methanesulfonic acid, Polyethylene glycol, and combinations thereof (collectively, and individually herein referred to as "alternative substrates").

In some embodiments, the reaction solution comprises at least 1 mM alternative substrate. In some embodiments, the reaction solution comprises at least 1 mM, at least 1.1 mM, at least 1.2 mM, at least 1.3 mM, at least 1.4, mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.1 mM, at least 3.2 mM, at least 3.3 mM, at least 3.5 mM, at least 3.6 mM, at least 3.7 mM, at least 3.8 mM, at least 3.9 mM, at least 4.0 mM, at least 4.1 mM, at least 4.2 mM, at least 4.3 mM, at least 4.4 mM, at least 4.5 mM, at least 4.6 mM, at least 4.7 mM, at least 4.8 mM, at least 4.9 mM, at least 5.0 mM, at least 5.1 mM, at least 5.2 mM, at least 5.3 mM, at least 5.4 mM, at least 5.5 mM, at least 5.6 mM, at least 5.7 mM, at least 5.8 mM, at least 5.9 mM, at least 6.0 mM, at least 6.1 mM, at least 6.2 mM, at least 6.3 mM, at least 6.4 mM, at least 6.5 mM, at least 6.6 mM, at least 6.7 mM, at least 6.8 mM, at least 6.9 mM, at least 7.0 mM, at least 7.1 mM, at least 7.2 mM, at least 7.3 mM, at least 7.4 mM, at least 7.5 mM, at least 7.6 mM, at least 7.7 mM, at least 7.8 mM, at least 7.9 mM, at least 8.0 mM, at least 8.1 mM, at least 8.2 mM, at least 8.3 mM, at least 8.4 mM, at least 8.5 mM, at least 8.6 mM, at least 8.7 mM, at least 8.8 mM, at least 8.9 mM, at least 9.0 mM, at least 9.1 mM, at least 9.2 mM, at least 9.3 mM, at least 9.4 mM, at least 9.5 mM, at least 9.6 mM, at least 9.7 mM, at least 9.8 mM, at least 9.9 mM, or at least 10 mM alternative substrate, including all ranges and subranges therebetween.

In some embodiments, the reaction solution comprises between 2.4 mM and 120 mM alternative substrate. In some embodiments, the reaction solution comprises between 1 mM and 40 mM alternative substrate. In some embodiments, the reaction solution comprises between 1 mM and 5 mM, between 5 mM and 10 mM, between 10 mM and 15 mM, between 15 mM and 20 mM, between 20 mM and 25 mM, between 25 mM and 30 mM, between 30 mM and 35 mM, between 35 mM and 40 mM alternative substrate.

In some embodiments, the reaction solution comprises at least 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, 550 mM, 600 mM, 650 mM, 700 mM, 750 mM, 800 mM, 850 mM, 900 mM, 950 mM, 1000 mM alternative substrate, including all ranges and subranges therebetween.

Reaction Yields

As noted above, the methods of the present disclosure cause the algal biomass in the reaction solution to produce higher quantities of secondary metabolites, such as antimethanogenic compounds, than a comparable algal biomass without the reaction solution.

For example, in some embodiments, the algal biomass or enzyme produces at least 10%, 20%, 30%, 40%, 50%, 60%, 70%, 80%, 90% 100%, 200%, 300%, 400%, 500%, 600%, 700%, 800%, 900%, 1,000%, 2,000%, 3,000%, 4,000%, 5,000%, 6,000%, 7,000%, 8,000%, 9,000%, 10,000%, 15,000%, 20,000%, 25,000%, or at least 30,000% higher quantities of secondary metabolites than a comparable biomass or enzyme without the reaction solution, including all ranges and subranges therebetween.

In some embodiments, the present disclosure teaches the criticality of the chosen VFA substrate. Thus, in some embodiments, the algal biomass or enzyme in the reaction solution of the present disclosure produces higher quantities of secondary metabolites than a comparable algal biomass and comparable reaction solution lacking a VFA or with a different VFA substrate (e.g., seawater organic runoff, organic compounds 5 (pentane-2,4-dione) or 6 (heptane 2,4,6-trione)).

For example, in some embodiments, the algal biomass or enzyme produces at least 10%, 20%, 30%, 40%, 50%, 60%, 70%, 80%, 90% 100%, 200%, 300%, 400%, 500%, 600%, 700%, 800%, 900%, 1,000%, 2,000%, 3,000%, 4,000%, 5,000%, 6,000%, 7,000%, 8,000%, 9,000%, 10,000%, 15,000%, 20,000%, 25,000%, or at least 30,000% higher quantities of secondary metabolites than a comparable algal biomass and comparable reaction solution lacking a VFA or with a different VFA substrate (e.g., seawater organic runoff, organic compounds 5 (pentane-2,4-dione) or 6 (heptane 2,4,6-trione)).

In some embodiments, the method for producing a secondary metabolite in an algal biomass produces at least 0.1 mg, at least 1 mg, at least 2 mg, at least 3 mg, at least 4 mg, at least 5 mg, at least 6 mg, at least 7 mg, at least 8 mg, at least 9 mg, at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1000 mg, at least 2,000 mg, at least 3,000 mg, at least 4,000 mg, or at least 5000 mg of a secondary metabolite per gram of algal biomass, including all ranges and subranges therebetween.

In some embodiments, the secondary metabolite is a methyl halide. In some embodiments, the secondary metabolite is an antimethanogenic compound. In some embodiments, the secondary metabolite is selected from the group consisting of methyl bromide, methyl chloride, methyl iodide, methyl fluoride, bromodichlormethane, trichlorethylene, bromoform, chloroform, iodoform, fluoroform, dibromomethane, and combinations thereof.

In some embodiments, the algal biomass comprises a species of *Asparagopsis* and produces at least 1 mg/g, at least 1.1 mg/g, at least 1.2 mg/g, at least 1.3 mg/g, at least 1.4 mg/g, at least 1.5 mg/g, at least 1.6 mg/g, at least 1.7 mg/g, at least 1.8 mg/g, at least 1.9 mg/g, at least 2.0 mg/g, at least 2.1 mg/g, at least 2.2 mg/g, at least 2.3 mg/g, at least 2.4 mg/g, at least 2.5 mg/g, at least 2.6 mg/g, at least 2.7 mg/g, at least 2.8 mg/g, at least 2.9 mg/g, at least 3.0 mg/g, at least 3.1 mg/g, at least 3.2 mg/g, at least 3.3 mg/g, at least 3.4 mg/g, at least 3.5 mg/g, at least 3.6 mg/g, at least 3.7 mg/g, at least 3.8 mg/g, at least 3.9 mg/g, or at least 4.0 mg/g dry biomass bromoform.

In some embodiments, algal biomass comprises a species of *Gracilaria* and produces at least 100 µg/g, at least 150 µg/g, at least 200 µg/g, at least 250 µg/g, at least 300 µg/g, at least 350 µg/g, at least 400 µg/g, at least 450 µg/g, at least 500 µg/g, at least 550 µg/g, at least 600 µg/g, at least 650 µg/g, at least 700 µg/g, at least 750 µg/g, at least 800 µg/g, at least 850 µg/g, at least 900 µg/g, at least 950 µg/g, or at least 1 mg/g dry biomass bromoform.

In some embodiments, algal biomass comprises a species of *Macrocystis* and produces at least 1 mg/g, at least 1.1 mg/g, at least 1.2 mg/g, at least 1.3 mg/g, at least 1.4 mg/g, at least 1.5 mg/g, at least 1.6 mg/g, at least 1.7 mg/g, at least 1.8 mg/g, at least 1.9 mg/g, at least 2.0 mg/g, at least 2.1 mg/g, at least 2.2 mg/g, at least 2.3 mg/g, at least 2.4 mg/g, at least 2.5 mg/g, at least 2.6 mg/g, at least 2.7 mg/g, at least 2.8 mg/g, at least 2.9 mg/g, at least 3.0 mg/g, at least 3.1 mg/g, at least 3.2 mg/g, at least 3.3 mg/g, at least 3.4 mg/g, at least 3.5 mg/g, at least 3.6 mg/g, at least 3.7 mg/g, at least 3.8 mg/g, at least 3.9 mg/g, at least 4.0 mg/g, at least 4.1 mg/g, at least 4.2 mg/g, at least 4.3 mg/g, at least 4.4 mg/g, at least 4.5 mg/g, at least 4.6 mg/g, at least 4.7 mg/g, at least 4.8 mg/g, at least 4.9 mg/g, at least 5.0 mg/g dry biomass bromoform.

Reaction Vessel

In some embodiments, the method may be carried out in a vessel 10. The biomass 12 of algae is combined with the reaction solution 14 in the vessel 10. The vessel 10 may be a closed vessel.

The vessel 10 may also comprise a mixture outlet 30 that is adapted to allow for the release of the mixture (including any secondary metabolites) from the vessel 10. The vessel 10 may further include a vessel inlet 26 adapted to allow for the introduction of the biomass 12, the reaction solution 14, and any other substances into the vessel 10.

The biomass 12 of algae may comprise fresh, frozen, and/or freeze-dried algae. The algae may be dead or alive, or a combination of both. If the biomass 12 of algae comprises dead (or predominantly dead) algae, the biomass 12 may be first crushed, homogenized, lysed, or otherwise treated in order to release enzymes (such as bromoperoxidase) from within the cell bodies.

If the biomass 12 comprises living algae, suitable growing media 18 may also be introduced into the vessel 10 to assist in the growth of the algae within the biomass 12. The vessel 10 may further comprise an aerator 20 that is located within the mixture layer 34. The aerator 32 is configured to introduce air bubbles, which may be helpful in supplying air, including oxygen or carbon dioxide. The aerator 20 may also be connected to a carbon dioxide tank 24 to provide carbon dioxide ($CO_2$) to the biomass 12 for photosynthesis. The aerator 20 may be connected by an air tube 22 to an air pump 21 or the carbon dioxide tank 24.

A water outlet 26 may also be provided to allow for the transfer of water and/or the biomass 12 from the mixture. In addition, one or more growing lights 32 may be provided over the vessel 10 to provide light energy for the biomass 12. The growing lights 48 may comprise light-emitting diodes (LED) lighting or some other suitable forms of lighting. Alternatively, the vessel 10 may instead be exposed to the sun 44 to provide light energy for the biomass 12.

Figure 2:
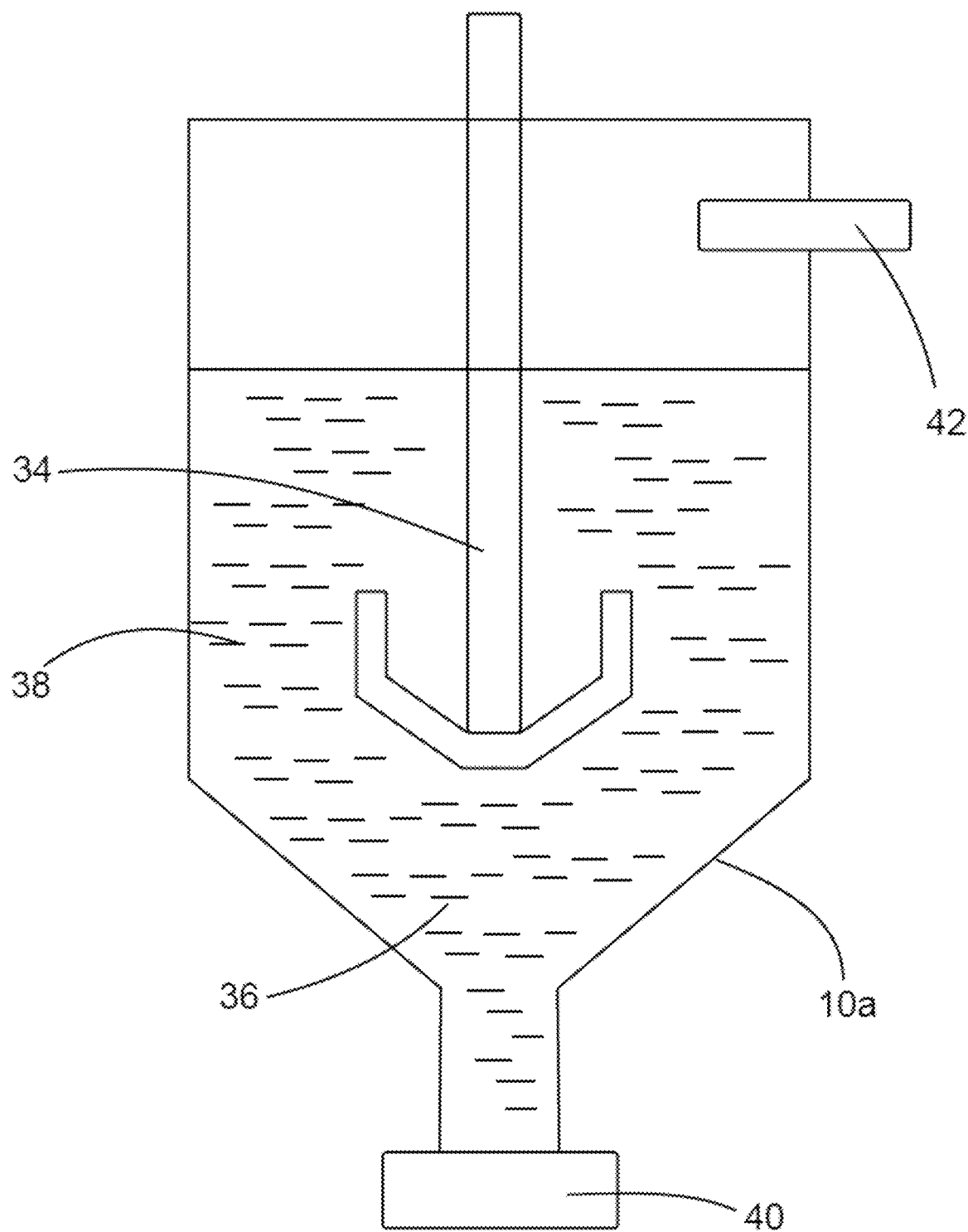
FIG. 2 is a diagram of a vessel for carrying out methods of the present disclosure.

As shown in FIG. 2, the vessel 10a may comprise a mixer 34 adapted to mix or agitate the biomass of algae and/or the reaction solution within the vessel in order to promote or facilitate the reaction process.

Utilizing Isolated and/or Purified Enzymes to Produce Secondary Metabolites

In another embodiment, the disclosure teaches a method for producing a secondary metabolite, the method comprising the steps of providing a haloperoxidase enzyme; providing a reaction solution, the reaction solution comprising: a volatile fatty acid, hydrogen peroxide, and a halide; and contacting the haloperoxidase enzyme with the reaction solution for a time period sufficient to synthesize the secondary metabolite. Reaction solutions compatible with this technique are described above in the "Reaction Solutions" section.

In some embodiments, the haloperoxidase is isolated and purified from a species of macroalgae. In some embodiments, the haloperoxidase is isolated and purified from a species of microalgae. In some embodiments, the haloperoxidase is isolated and purified from a species of cyanobacteria. In some embodiments, the haloperoxidase is a recombinant. In some embodiments, the haloperoxidase is an artificially synthesized protein.

Methods of producing isolated/purified haloperoxidases are known in the art, including in (Thapa H. R. et al. Genetic and Biochemical Reconstitution of Bromoform Biosynthesis in *Asparagopsis* Lends Insights into Seaweed Reactive Oxygen Species Enzymology, *ACS Chem. Biol.* 2020 15, 1662-1670, which is hereby incorporated for all purposes). The methods of the present disclosure are compatible with various degrees of enzyme purification, including simple fractionation to recombinant expression of the enzyme.

In some embodiments, the method for producing a secondary metabolite using isolated and/or purified enzymes produces at least 1.1 mg of secondary metabolite per mg of haloperoxidase enzyme. In some embodiments, the method produces at least 10 mg of secondary metabolite per mg of haloperoxidase enzyme. In some embodiments, the method produces at least 100 mg of secondary metabolite per mg of haloperoxidase enzyme. In some embodiments, the method produces at least 1000 mg of secondary metabolite per mg of haloperoxidase enzyme.

In some embodiments, the method for producing a secondary metabolite using isolated and/or purified enzymes produces at least 2 mg, at least 3 mg, at least 4 mg, at least 5 mg, at least 6 mg, at least 7 mg, at least 8 mg, at least 9 mg, at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1000 mg, at least 2,000 mg, at least 3,000 mg, at least 4,000 mg, or at least 5000 mg of a secondary metabolite per mg of haloperoxidase enzyme, including all ranges and subranges therebetween.

Reaction Parameters for Producing Secondary Metabolites

Person having skill in the art are able to determine when a reaction should be stopped. For example, a person having skill in the art may choose to keep the algal biomass in contact with the reaction solution only during the time of highest production of secondary metabolites. In other embodiments the algal biomass and reaction solution can be kept in contact until the rate of production of secondary metabolites is higher than the rate of degradation. In some embodiments, the algal biomass may be kept in contact with the reaction solution indefinitely, while secondary compounds are separated out over time (e.g., such as in the oil-layered embodiment described in this document). Secondary metabolites, such as antimethanogenic compounds are detectable via well-known techniques, thus permitting skilled practitioners to decide when to stop a reaction and/or when to begin separating out products.

In some embodiments, the methods of producing a secondary metabolite described herein may be allowed to process for a time period from 30 minutes to up to 36 hours. In some embodiments, the time period is at least 30 minutes, at least 90 minutes, at least 6 hours, at least 12 hours, at least 18 hours, at least 24 hours, or at least 36 hours.

In some embodiments, the methods of producing a secondary metabolite described herein occur at between approximately 5° C. and 40° C. In some embodiments, the methods of producing a secondary metabolite described herein occur at between approximately 15° C. and 35° C. In some embodiments, the methods of producing a secondary metabolite described herein occur at between approximately 20° C. and 30° C. In some embodiments, a heat source and/or a cooling device may be provided to maintain or heat the mixture to the appropriate temperature.

In some embodiments, the reaction solution has a pH of at least 5.0. In some embodiments, the reaction solution has a pH of at least 6.0. In some embodiments, the reaction solution has a pH of between approximately 5.0 and 11.0. In some embodiments, the reaction solution has a pH of between approximately 6.0 and approximately 7.8. As the process proceeds and more compounds are produced, the pH of the mixture may drop. Thus, in some embodiments, a buffering agent may be added to maintain the pH at approximately neutral pH conditions while the reaction proceeds.

Persons having skill in the art will be familiar with various buffers that can be used to maintain the desired pH. A non-limiting list of known buffers and their pH ranges is provided as Table 2. In some embodiments, the buffer is added to the reaction solution at between 10 mM and 100 mM. In some embodiments, the buffering agent is HEPES.

TABLE 2

Illustrative buffers

| Common name and/or chemical name | Useful pH range |
|---|---|
| ACES | 6.1-7.5 |
| Acetic acid (Ethanoic acid) | 3.8-5.8 |
| ADA | 6.0-7.2 |
| AMP | 9.0-10.5 |
| AMPD | 7.8-9.7 |
| AMPSO | 8.3-9.7 |
| BES | 6.4-7.8 |
| Bicine (2-(bis(2-hydroxyethyl)amino)acetic acid) | 7.6-9.0 |
| Bis-Tris | 5.8-7.2 |
| Bis-Tris Propane | 6.3-9.5 |
| Boric acid | 8.25-10.25 |
| CABS | 10.0-11.4 |
| Cacodylate (dimethylarsenic acid) | 5.0-7.4 |
| CAPS | 9.7-11.1 |
| CAPSO | 8.9-10.3 |
| CHES (N-Cyclohexyl-2-aminoethanesulfonic acid) | 8.3-10.3 |
| Citric acid (2-Hydroxypropane-1,2,3-tricarboxylic acid) | 2.1-7.4 |
| DIPSO | 7.0-8.2 |
| EPPS | 7.3-8.7 |
| Gly-Gly | 7.5-8.9 |
| HEPBS | 7.6-9.0 |
| HEPES (4-(2-hydroxyethyl)-1-piperazineethanesulfonic acid) | 2.5-3.5 or 6.8-8.2 |
| HEPPSO | 7.1-8.5 |
| Imidazole | 6.2-7.8 |
| $KH_2PO_4$ (Monopotassium phosphate) | 6.2-8.2 |
| $K_2HPO_4$, | 8.7-9.4 |
| $K_3PO_4$ | 11.5-12.3 |
| MES (2-(N-morpholino)ethanesulfonic acid) | 5.5-6.7 |
| Malic acid | 3.7-6.0 |
| MOBS | 6.9-8.3 |
| MOPS (3-(N-morpholino)propanesulfonic acid) | 6.5-7.9 |
| MOPSO | 6.2-7.6 |
| PBS or high buffering capacity PBS | 5.8-8.0 |
| PIPES | 6.1-7.5 |
| PIPES (piperazine-N,N'-bis(2-ethanesulfonic acid)) | 6.1-7.5 |
| POPSO | 7.2-8.5 |
| Sodium cacodylate trihydrate | 5.0-7.4 |
| Succinic acid | 3.2-6.5 |
| Sodium acetate trihydrate | 3.6-5.6 |
| TABS | 8.2-9.6 |
| TAPS ([tris(hydroxymethyl)methylamino]propanesulfonic acid) | 7.7-9.1 |
| TAPSO (3-[N-tris(hydroxymethyl)methylamino]-2-hydroxypropanesulfonic acid) | 7.0-8.2 |
| TEA | 7.3-8.3 |
| TES (2-[[1,3-dihydroxy-2-(hydroxymethyl)propan-2-yl]amino]ethanesulfonic acid) | 6.8-8.2 |
| Tricine (N-[tris(hydroxymethyl)methyl]glycine) | 7.4-8.8 |
| Tris (tris(hydroxymethyl)aminomethane) or (2-amino-2-(hydroxymethyl)propane-1,3-diol) | 7.1-9.1 |

In some embodiments, the methods of producing secondary metabolites described herein are carried out at standard atmospheric pressure (approximately 1 bar). In some embodiments, the method is carried out in conditions less than 1.5 bar.

Extraction of Secondary Metabolites, Including Antimethanogenic Compounds

The resulting secondary metabolites metabolized by the methods disclosed herein may be extracted, enriched, and formulated using a number of techniques.

Oil Extraction of Secondary Metabolites

Referring to FIG. 1, in another embodiment of the disclosure, the secondary metabolites, such as bromoform, may be extracted from the reaction by introducing an oil layer 16 above the reaction solution 14 comprising the algal biomass or the enzyme, and the reaction solution.

As described above, the haloperoxidase (either from the biomass or in an isolated and/or purified form) catalyzes the oxidation of halide ions, which subsequently reacts with other substrates to form bioactives and metabolites including antimethanogenic compounds such as bromoform. The resulting compounds are released into the reaction solution. As the antimethanogenic compounds are typically oil-soluble, they will accumulate in the oil layer, thus allowing for the antimethanogenic compounds to be removed over time without disrupting the reaction. In some embodiments, the oil layer may be replenished with new oil. Therefore, as the antimethanogenic compounds are produced, they can be extracted and removed from the reaction in a continuous or semi-continuous manner. Multiple types of metabolites and bioactives may be extracted by the oil in the oil layer.

In some embodiments, the oil layer may comprise any suitable oil, including, for example, vegetable oil. In some embodiments, the oil layer comprises an oil selected from the group consisting of canola oil, olive oil, corn oil, mineral oil, and combinations thereof. In some embodiments, the oil is selected from soybean oil, corn oil, palm kernel oil, rapeseed oil, sunflower oil, safflower oil, coconut oil, rice bran oil, sesame oil, flaxseed oil, hemp oil, or cottonseed oil. In some embodiments, the oil is peanut oil, almond oil, beech nut oil, brazil nut oil, cashew oil, hazelnut oil, macadamia oil, mongongo nut oil, pecan oil, pine nut oil, pistachio oil, walnut oil, or pumpkin seed oil. In some embodiments, the oil is grapefruit seed oil, lemon oil, apricot oil, apple seed oil, argan oil, avocado oil, or orange oil.

In some embodiments the oil layer is sufficiently large so as to form a continuous layer over the reaction solution. Persons having skill in the art will be able to determine how much oil to add to a reaction based on the container shape, expected yield, and planned recoveries/oil replacement plan. In some embodiments the ratio of biomass to the at least one oil may be 0.01 g:1 mL, 0.05 g:1 mL, 0.1 g:1 mL, 0.2 g:1 mL, 0.3 g:1 mL, 0.4 g:1 mL, 0.5 g:1 mL, 0.6 g:1 mL, 0.7 g:1 mL, 0.8 g:1 mL, 0.9 g:1 mL, 1 g:1 mL, 1.1 g:1 mL, 1.2 g:1 mL, 1.3 g:1 mL, 1.4 g:1 mL, 1.5 g:1 mL, 2 g:1 mL, 3 g:1 mL, 4 g:1 mL, 5 g:1 mL, 6 g:1 mL, 7 g:1 mL, 8 g:1 mL, 9 g:1 mL, 10 g:1 mL, 20 g:1 mL, 30 g:1 mL, 40 g:1 mL, 50 g:1 mL, 60 g:1 mL, 70 g:1 mL, 80 g:1 mL, 90 g:1 mL or 100 g:1 mL.

The use of an oil layer may also serve to act as a barrier to the algal biomass or enzyme plus reaction solution mixture. Biological contaminants (such as those in the air) will become trapped within the oil layer, thus preventing the contaminants from affecting the enzymatic reactions. Furthermore, metal ions and other undesirable ions (e.g. arsenic, aluminum, fluoride, and iodide ions) that may be present in the algal biomass are not well absorbed by the oil. Therefore, these undesirable ions are not extracted with the bioactives and metabolites in the oil layer and into the final product.

Therefore, in some embodiments, the oil method of extraction reduces heavy metals and metal ions in the final product.

Stress-Induced Methods to Extract/Induce Release of Secondary Metabolites

In another embodiment, the disclosure teaches a method of extracting secondary metabolites from algae and microorganisms, the method comprising the steps of providing an algal biomass, and exposing the algal biomass to an environmental stress, wherein the environmental stress induces the algae or microorganism to release the secondary metabolite, thereby allowing extraction of the commercially valuable bioactives and metabolites, including antimethanogenic compounds.

In some embodiments, the environmental stress is selected from the group consisting of, increased acidity, reduced acidity, reduced oxygen content, cold stress, heat stress, light stress, osmotic shock, and combinations thereof.

In some embodiments, the environmental stress is reduced oxygen content in aqueous solution containing algal biomass. In some embodiments, the reduced oxygen content is less than one parts per million (<1 ppm) dissolved oxygen.

In some embodiments, the stress-induced method of extracting secondary metabolites produces at least a 1.5-fold increase in secondary metabolites compared to non-stressed algae. In some embodiments, the method produces 2-fold more secondary metabolites than non-stressed algae. In some embodiments, the method produces at least 3-fold, at least 4-fold, at least 5-fold, at least 6-fold, at least 7-fold, at least 8-fold, at least 9-fold, or at least 10-fold more secondary metabolites than non-stressed algae.

Additional methods for extracting and collecting bioactives and metabolites are well known in the art, and include, for example, mechanical pressing, use of chemical solvents, enzymatic extraction, precipitation, supercritical $CO_2$ extraction, chromatography, adsorption, electrophoresis, crystallization, binding, foam fractionation, distillation, and combinations thereof.

Algal Cultivation Systems

In some embodiments, the disclosure provides an algal cultivation system comprising an algal biomass; an algal growth substrate; and an oil layer. As relayed above, the antimethanogenic compounds produced by the algal biomass are typically oil-soluble, thus the oil layer may comprise bioactives, including antimethanogenic compounds, which can be extracted by removing the oil layer.

In some embodiments, the algal growth substrate comprises an osmotic regulator, a carbon source, and a nutrient mix. In some embodiments, the carbon source is carbon dioxide, bicarbonate, carbonic acid, and/or carbonate. In some embodiments the algal growth substrate comprises less than 100 ppm, less than 90 ppm, less than 80 ppm, less than 70 ppm, less than 60 ppm, less than 50 ppm, less than 40 ppm, less than 30 ppm, less than 20 ppm, or less than 10 ppm dissolved $CO_2$, bicarbonate, carbonic acid, and/or carbonate. In some embodiments, the algal growth substrate also contains a physical substrate to hold the algae, such as sand, soil, or other known physical growth substrates.

In some embodiments, the osmotic regulator is salt. In some embodiments, the algal growth substrate comprises a salinity of between about 1 and 50 parts per thousand (ppt). In some embodiments, the algal growth substrate comprises a salinity of at least 10 ppt, at least 15 ppt, at least 20 ppt, at least 25 ppt, at least 30 ppt, at least 35 ppt, at least 40 ppt, at least 45 ppt, or at least 50 ppt. In some embodiments, the algal growth substrate comprises a salinity of between about 33 ppt and 37 ppt. In some embodiments, where freshwater algae is grown, the osmotic regulator can be omitted.

In some embodiments, the salt is sodium chloride. Other salts may be used, for example, sodium carbonate, ammonium chloride, sodium acetate, sodium bromide, potassium cyanide, zinc chloride hydroxide, potassium chlorate, calcium phosphate, sodium nitrate, potassium cerium fluoride, potassium chloride, sodium bicarbonate, phosphate buffer, and combinations thereof. In some embodiments, the osmotic regulator is a sugar or sugar alcohol. In some embodiments, the osmotic regulator is glycerol.

As used herein, "nutrient mix" refers to any growth medium comprising nutrients usable to support the growth of microorganisms and/or algae. A growth medium may comprise waste materials such as, without limitation, wastewater, sewage, raw sewage, liquefied solid waste, washing water, grey water, drainage, black water, industrial effluvia, residential effluvia, commercial effluvia, other waste, or combinations thereof. The nutrient mix may also comprise non-waste materials, such as, without limitation, food processing by-products, sugar solutions, starch solutions, wort, mash, malt, grist, and agar. The nutrient mix may also comprise, without limitation, organics, nitrogen-containing materials, and/or phosphorous-containing materials.

In some embodiments, the nutrient mix comprises a nitrogen source, for example nitrate, ammonium, urea or organic nitrogen such as from amino acids. In some embodiments, the nutrient mix comprises a phosphorus source, for example an inorganic combination of dihydrogen phosphate, hydrogen phosphate, and $PO_4^{3-}$). Vitamins such as B12, thiamine-HC, biotin, $Ca^{2+}$, $Mg^{2+}$, iron (as $Fe^{2+}$, or $Fe^{3+}$), and some trace elements may also be included in the nutrient mix. Nutrient mixes are well known in the art and commercially available for purchase. See for example, Pentair aquatic nutrient mix (part A and part B), also known as "F/2" media. In some embodiments, the system comprises a reaction solution as described herein.

Compositions

In some embodiments, the disclosure relates to compositions comprising an algal biomass, a reaction solution, the reaction solution comprising a volatile fatty acid, hydrogen peroxide, and a halide, and a secondary metabolite.

In some embodiments, the disclosure relates to compositions comprising an isolated and purified haloperoxidase, a reaction solution, the reaction solution comprising a volatile fatty acid, hydrogen peroxide, and a halide, and a secondary metabolite.

In some embodiments, the disclosure relates to compositions comprising an oil and a full spectrum of bioactives, metabolites, and antimethanogenic compounds produced by an algal biomass.

In some embodiments, the full spectrum oil comprises at least 2 mg/L of an antimethanogenic compound. In some embodiments, the full spectrum oil comprises at least 4 mg/L, at least 6 mg/L, at least 8 mg/L, or at least 10 mg/L of an antimethanogenic compound. In some embodiments, the full spectrum oil comprises between 10 mg/L and 20 mg/L, between 20 mg/L and 30 mg/L, between 30 mg/L and 40 mg/L, between 40 mg/L and 50 mg/L, between 50 mg/L and 60 mg/L, between 60 mg/L and 70 mg/L, between 70 mg/L and 80 mg/L, between 80 mg/L and 90 mg/L, or between 90 mg/L and 100 mg/L of an antimethanogenic compound.

Formulations

In some embodiments, the extracted commercially valuable bioactives and metabolites including antimethanogenic compounds or full spectrum oil may be formulated and/or incorporated into animal feed for feeding to ruminant animals. Thus, in some embodiments, the disclosure relates to a composition comprising a full spectrum oil as described herein and an animal feed.

In some embodiments, the extracted commercially valuable bioactives and metabolites including antimethanogenic compounds is added directly to the ration of food (as a so-called top-dress). When used as a feed additive, the commercially valuable bioactives and metabolites and antimethanogenic compounds may be further formulated to enhance the flavor, nutrition, and/or shelf life. Non-limiting examples of formulations may include preservatives, antioxidants, emulsifiers, stabilising agents, acidity regulators, silage additives, sensory additives, flavours, colorants, nutritional additives such as vitamins, amino acids and trace elements, and zootechnical additives, such as digestibility enhancers and gut flora stabilizers.

In some embodiments, the commercially valuable bioactives and metabolites including antimethanogenic compounds are incorporated into the manufacture of compounded animal feeds. Compounded animal feeds as used herein refers to any composition suitable for use as an animal feed and which is blended from various materials (e.g., wheat bran, rice bran, corn meal, cereal grains, such as barley, wheat, rye and oat, soybean meal, alfalfa meal, cottonseed meal, wheat powder). Compounded animal feed may be liquid, solid, or semi-solid.

In some embodiments, the extracted oil comprising the commercially valuable bioactives and metabolites including antimethanogenic compounds may be formulated and/or incorporated into a lick block.

Example Organisms for Use with the Disclosed Extended Metabolism Methods, Systems, and Compositions One of the unexpected benefits of the presently disclosed methods is that, in some embodiments, they allow for the production of commercially valuable bioactives, metabolites including antimethanogenic compounds from other algae previously thought to not produce or accumulate high levels of such compounds (e.g., bromoform, fluoroform, chloroform, iodoform). Without wishing to be bound by any one theory, the inventors hypothesize that many algal species are capable of producing commercially valuable bioactives, metabolites including antimethanogenic compounds, but do not accumulate the compound in their tissues, and/or otherwise lack the ability to produce a regular supply of one or more of the necessary reactants. In some embodiments, algae that produce relatively low to no contents of antimethanogenic compounds (e.g., bromoform) are able to produce higher quantities than well-established bromoform accumulating algae such as *Asparagopsis*, when contacted with the reaction solution.

In one embodiment of the disclosure, algae of the genus *Asparagopsis* may be used in the biomass. However, it is understood that other species of macroalgae and microalgae may be used as well. For example, other types of red algae besides *Asparagopsis* may be used, including, but not limited to, those of the Order Rhodophyta, Class Florideophyceae, including *Gracilaria* and *Plocamium*. In still a further embodiment, the red algae is of the genus *Gracilariales*. In another embodiment, the red algae is of the order Gigartinales or *Chondrus*.

In addition, besides red algae, brown algae may also be used, including, but not limited to, those of the genus *Laminaria*, including *Macrocystis pyrifera, Nereocystis* and other kelps, as well as *Dichtyota*.

Furthermore, the biomass may comprise single or multiple species of algae and may comprise microalgae, macroalgae, or a combination of both.

In some embodiments, the methods, systems, and compositions of the disclosure comprise a microorganism of the order Rhodophyta, Class Florideophyceae, for example, *Gracilaria* and *Plocamium*.

In some embodiments, the methods, systems, and compositions of the disclosure comprise a species of red algae. In some embodiments, the red algae is a species of *Asparagopsis, Bonnemaisonia, Delisea, Ptilonia, Leptophyllis*, and/or *Pleuroblepharidella*. Species of *Asparagopsis* include *A. armata, A. taxiformis, A. svedelli, A. delilei, A. hamifera, A. sanfordiana*

In some embodiments, the methods, systems, and compositions of the disclosure comprise a species of brown algae. In some embodiments, the methods, systems, and compositions of the disclosure comprise a microorganism from the genus *Laminaria*. In some embodiments, the methods, systems, and compositions of the disclosure comprise a microorganism from the genus *Nereocystis*. In some embodiments, the methods, systems, and compositions of the disclosure comprise a microorganism from the genus *dichtyota*.

In some embodiments, the methods, systems, and compositions of the disclosure comprise *Laminaria saccharina, Laminaria digitata, Fucus vesiculosis, Fuscus distichus, Alaria esculenta, Chorda filum, Ceramium rubrum, Corallina pilulifera, Pelvetia canaliculate, Ascophyllum nodusum, Chondrus crispus, Plocamium hamatum, Gigartina stellata, Enteromorpha lima, Ulva lacta, Bonnemaisonia hamifera, Asparagopsis taxiformis, Asparagopsis Armata, Gracilaria spp., Antithamnionella sarniensis, Antithamnion plumula*, or *Macrocystis pyrifera*.

In some embodiments, the methods, systems, and compositions of the disclosure comprise phytoplankton. In some embodiments, the methods, systems, and compositions of the disclosure comprise a diatom species from *Nitzschia* and/or *Porosira*.

In some embodiments, the methods, systems, and compositions of the disclosure comprise a species of blue green algae (also known as cyanobacteria). In some embodiments, the species of blue green algae comprise at least one species of *Chlorella*. In some embodiments, the species of algae comprises *Chlorella protothecoides, Chlorella vulgaris*, and/or *Spirulina-Arthrospira platensis*.

In some embodiments, the methods, systems, and compositions of the disclosure comprise an algal biomass comprising live algae. In some embodiments, the live algae is fresh algae. In some embodiments, the live algae is thawed algae. In some embodiments, the algal biomass comprises dead algae. In some embodiments, the algal biomass comprises lysed algae. In some embodiments, the algal biomass comprises freeze-dried algae. In some embodiments, the algal biomass comprises macroalgae. In some embodiments, thealgal biomass comprises microalgae.

In some embodiments, the algal biomass comprises red algae of the order Rhodophyta. In some embodiments, the algal biomass comprises red algae of the order Bonnemaisoniales. In some embodiments, the algal biomass comprises red algae of the genus *Asparagopsis*.

In some embodiments, the algal biomass comprises algae selected from the group consisting of: algae of class Florideophyceae, algae of genus *Gracilaria*, algae of genus *Palmeria*, and genus *Chondrus*.

In some embodiments, the algal biomass comprises brown algae of class Phaeophyceae. In some embodiments, the algal biomass comprises green algae.

In some embodiments, the algal biomass comprises an algae selected from the group consisting of *Laminaria*, *Macrocystis pyrifera* and *Dichtyota*.

In some embodiments, the biomass is a fungi. In some embodiments, the biomass is a yeast.

In some embodiments, the extended metabolism methods of the present disclosure are compatible with any algae or microorganism encoding a haloperoxidase enzyme.

In some embodiments, the gene encoding the haloperoxidase in the algae or microbe, exhibits at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or 100% sequence identity with any one of SEQ ID NO: 1-53.

Engineered or Natural Microbes for use With the Disclosed Methods, Systems, and Compositions The methods, systems, and compositions disclosed herein may also be used with natural and/or genetically modified organisms. Methods of cloning and expressing genes are well known in the art. For example, vanadium bromoperoxidase from the marine red alga *Corallina officinalis* has been cloned and heterologously expressed in Esherichia coli. The recombinant vanadium bromoperoxidase behaved similarly to native vanadium bromoperoxidase from the alga (Carter J N, et al. Reactivity of recombinant and mutant vanadium bromoperoxidase from the red alga *Corallina officinalis*. J Inorg Biochem. 2002 Jul. 25; 91(1):59-69).

In another example, a bromoperoxidase from macro-alga *Corallina piluhliera* was cloned and expressed in *E. coli* (Shimonishi M, et al., Cloning and expression of the gene for a vanadium-dependent bromoperoxidase from a marine macro-alga, *Corallina pilulifera*. FEBS Lett. 1998 May 22; 428(1-2): 105-10).

Example peroxidase genes are provided in Table 3 below.

TABLE 3

Illustrative peroxidases

| Gene | Species of origin | Accession no. | Sequence |
|---|---|---|---|
| Mbb1 | *A. A. taxiformis* | MN966723 | SEQ ID NO: 1 |
| Mbb4 | *A. taxiformis* | MN893468 | SEQ ID NO: 2 |
| Bpo1 | *Corallina pilulifera* | D81657 | SEQ ID NO: 3 |
| Bpo2 | *Corallina pilulifera* | D87658 | SEQ ID NO: 4 |
| Haloperoxidase | *Amycolatopsis mediterranei* U32 | YP 003765940.1 | SEQ ID NO: 5 |
| Mc140 | *Streptomyces* sp. CNH189 | AGH68925.1 | SEQ ID NO: 6 |
| Mc124 | *Streptomyces* sp. CNH189 | AGH68909.1 | SEQ ID NO: 7 |
| vanadium-dependent haloperoxidase | *Gramella forsetii* KT0803 | YP 861074.1 | SEQ ID NO: 8 |
| vanadium-dependent haloperoxidase | *Zobellia galactanivorans* | YP 004736687.1 | SEQ ID NO: 9 |
| vanadium-dependent haloperoxidase | *Zobellia galactanivorans* | YP 004736527.1 | SEQ ID NO: 10 |
| vanadium-dependent haloperoxidase | *Zobellia galactanivorans* | YP 004735706.1 | SEQ ID NO: 11 |
| vanadium-dependent haloperoxidase | *Zunongwangia profunda* SM-A87 | YP 003584965.1 | SEQ ID NO: 12 |
| vanadium-dependent bromoperoxidase | *Acaryochloris marina* MBIC11017 | YP 001515553.1 | SEQ ID NO: 13 |
| vanadium-dependent bromoperoxidase 2 | *Synechococcus* sp. CC9311 | YP 731869.1 | SEQ ID NO: 14 |
| vanadium-dependent haloperoxidase | *Clostridium botulinum* A str. ATCC 3502 | YP 001252786.1 | SEQ ID NO: 15 |
| vanadium-dependent haloperoxidase | *Clostridium botulinum* F str. Langeland | YP 001389606.1 | SEQ ID NO: 16 |
| vanadium-dependent haloperoxidase family | *Dyadobacter fermentans* DSM 18053 | YP 003089105.1 | SEQ ID NO: 17 |
| chloride peroxidase | *Rhodopseudomonas palustris* HaA2 | YP 487110.1 | SEQ ID NO: 18 |
| chloride peroxidase | *Sorangium cellulosum* So ce56 | YP 001615269.1 | SEQ ID NO: 19 |
| vanadium chloroperoxidase | *Curvularia inaequalis* | CAA59686.1 | SEQ ID NO: 20 |
| vanadium chloroperoxidase | *Embellisia didymospora* | CAA72622.1 | SEQ ID NO: 21 |
| vanadium chloroperoxidase | *Gaeumannomyces graminis* var. *tritici* R3-111a-1 | EJT71764.1 | SEQ ID NO: 22 |
| vanadium chloroperoxidase | *Pyrenophora tritici-repentis* Pt-1C-BFP | XP 001933850.1 | SEQ ID NO: 23 |
| PAP2 haloperoxidase domain-containing protein | *Naegleria gruberi* | XP 002679676.1 | SEQ ID NO: 24 |

TABLE 3-continued

Illustrative peroxidases

| Gene | Species of origin | Accession no. | Sequence |
|---|---|---|---|
| PAP2 haloperoxidase domain-containing protein | Naegleria gruberi | XP 002674918.1 | SEQ ID NO: 25 |
| PAP2 haloperoxidase domain-containing protein | Naegleria gruberi | XP 002670991.1 | SEQ ID NO: 26 |
| PAP2-like haloperoxidase | Chondrus crispus | CDF38596.1 | SEQ ID NO: 27 |
| PAP2/haloperoxidase-like protein | Chondrus crispus | CDF38595.1 | SEQ ID NO: 28 |
| vanadium-dependent bromoperoxidase | Chondrus crispus | CDF37939.1 | SEQ ID NO: 29 |
| PAP2/haloperoxidase-like protein | Chondrus crispus | CDF36854.1 | SEQ ID NO: 30 |
| PAP2/haloperoxidase-like protein | Chondrus crispus | CDF36853.1 | SEQ ID NO: 31 |
| PAP2/haloperoxidase-like protein | Chondrus crispus | CDF36848.1 | SEQ ID NO: 32 |
| PAP2/haloperoxidase-like protein | Chondrus crispus | CDF36845.1 | SEQ ID NO: 33 |
| vanadium-dependent bromoperoxidase vBPO | Chondrus crispus | CDF34463.1 | SEQ ID NO: 34 |
| vanadium-dependent bromoperoxidase vBPO | Chondrus crispus | CDF34418.1 | SEQ ID NO: 35 |
| PAP2/haloperoxidase-like protein | Chondrus crispus | CDF41387.1 | SEQ ID NO: 36 |
| PAP2-like haloperoxidase | Chondrus crispus | CDF40783.1 | SEQ ID NO: 37 |
| PAP2-like haloperoxidase | Chondrus crispus | CDF40781.1 | SEQ ID NO: 38 |
| vanadium-dependent bromoperoxidase vBPO | Chondrus crispus | CDF40600.1 | SEQ ID NO: 39 |
| vanadium-dependent bromoperoxidase | Corallina officinalis | AAM46061.1 | SEQ ID NO: 40 |
| vanadium-dependent bromoperoxidase 2 | Corallina pilulifera | BAA31262.1 | SEQ ID NO: 41 |
| vanadium-dependent bromoperoxidase 1 | Corallina pilulifera | BAA31261.1 | SEQ ID NO: 42 |
| vanadium-dependent bromoperoxidase 1 | Gracilaria changii | AGE00855.1 | SEQ ID NO: 43 |
| vanadium-dependent bromoperoxidase 2 | Ascophyllum nodosum | CCD42013.1 | SEQ ID NO: 44 |
| Vanadium-dependent bromoperoxidase | Ascophyllum nodosum | P81701.1 \| PRXV ASCNO | SEQ ID NO: 45 |
| vanadium-dependent bromoperoxidase | Ectocarpus siliculosus | CBN73942.1 | SEQ ID NO: 46 |
| vanadium bromoperoxidase | Fucus distichus | AAC35279.1 | SEQ ID NO: 47 |
| vanadium-dependent iodoperoxidase 1 | Laminaria digitata | CAF04025.1 | SEQ ID NO: 48 |
| putative vanadium-dependent iodoperoxidase 3 | Laminaria digitata | CAQ51446.1 | SEQ ID NO: 49 |
| putative vanadium-dependent bromoperoxidase 3 | Laminaria digitata | CAQ51441.1\| | SEQ ID NO: 50 |
| vanadium-dependent bromoperoxidase 1 | Laminaria digitata | CAD37191.1 | SEQ ID NO: 51 |
| haloperoxidase-like protein | Chlamydomonas reinhardtii | XP 001703431.1 | SEQ ID NO: 52 |
| acid phosphatase/ Vanadium-dependent haloperoxidase | Coccomyxa subellipsoidea C-169 | EIE20494.1 | SEQ ID NO: 53 |
| vCPO | Embellisia didymospora | CAA72344 | — |
| vCPO | Drechslera biseptata | CAA72008 | — |
| vCPO | Curvularia inaequalis | 1VNC | — |
| vBPO | C. officinalis | 1QHBA | — |
| vBPO | C. officinalis | AAM46061 | — |
| VBPO1 | Corallina pilulifera | BAA31261 | — |
| vBPO1 | L. digitata | CAD37191 | — |
| vBPO2 | L. digitata | CAD37192 | — |
| vBPO | Fucus distichus | AAC35279 | — |
| vBPO | Ascophyllum nodosum | P81701 | — |
| vIPO | Laminaria digitata | AJ619804 | — |

In some embodiments, naturally occurring and/or engineered microbes of the present disclosure encode and express a haloperoxidase exhibiting at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9% or 100% sequence identity with any one of SEQ ID NOs: 1-53 or those listed in Table 3.

Activating Endogenous Enzymes, Including Haloperoxidases

Many organisms have genes encoding for various peroxidases. The inventors of the present disclosure discovered that, in some embodiments, exposure to the appropriate substrates can trigger or enhance activation of haloperoxidases capable of producing antimethanogenic compounds. For example, bromide is present in sea water at about 65 mg/L, however in fresh water it is only present in trace amounts. Thus, ocean algae have active bromoperoxidases and produce bromoform, but species of freshwater algae may also be able to produce metabolites such as bromoform, fluoroform, iodoform, chloroform if provided the appropriate substrates.

In some embodiments, the disclosure teaches methods of inducing extended metabolism compounds via activating endogenous peroxidases.

Use of the Disclosed Antimethanogenic Compounds and Compositions in a Ruminant Animal Ruminant animals are those mammals in the suborder Ruminantia. Most have four-chambered stomachs and two-toed feet. The first chamber of the stomach is called the rumen and is the primary site microbial fermentation, where hard to digest plant material like cellulose is broken down. Including wild and domesticated species, there are roughly 200 species of ruminants. Example ruminants include, but are not limited to, bovine (cattle), goats, sheep, bison, giraffes, deer, elk, gazelles, antelopes, alpacas, llamas, and camels.

In some embodiments, the disclosure teaches a method of reducing enteric methane production in a ruminant animal over an extended period comprising administering an effective amount of an antimethanogenic compound. The antimethanogenic compound may be extracted and/or purified and incorporated into an animal feed, or may be administered as an oil extract (for example as a top-dress), with or without additives, as disclosed herein. In some embodiments, the antimethanogenic compound is administered in a range from 1 to 120 mg per kg of body weight. In some embodiments, the compound is administered in a range from 1 to 10 mg per kg of body weight.

In some embodiments, the ruminant animals supplemented with an antimethanogenic compound or a composition comprising an antimethanogenic compound of the present disclosure emit about 1%, 2%, 3%, 4%, 5%, 6%, 7%, 8%, 9%, 10% or 11% less methane than ruminant animals fed the same unsupplemented diet. In some embodiments, the ruminant animals supplemented with the antimethanogenic compounds and compositions of the present disclosure emit about 10% to 20%, 21% to 30%, 31% to 40%, 41% to 50%, 51% to 60%, 61% to 70%, 71% to 80%, 81% to 90%, 91% to 99% or 100% less methane than ruminant animals fed the same unsupplemented diet.

In another embodiment, the antimethanogenic compound or composition disclosed herein is administered to a ruminant animal continuously, every hour, every day, every 1.5 days, every 2 days, every 3 days or every 4.5 days. In another embodiment, the antimethanogenic compound or composition disclosed herein is administered to a ruminant animal every 7 days. In another embodiment, the antimethanogenic compound or composition disclosed herein is administered to a ruminant animal every month, every 3 months, every 6 months, every year, every 2 years. In another embodiment, the antimethanogenic compound or composition disclosed herein is administered to a ruminant animal once per lifetime of the animal.

In some embodiments, the animal is a breed of cattle. Exemplary cattle breeds include, but are not limited to, Angus, or Aberdeen-Angus, Ayrshire, Beefmaster, Belgium Blue, Belted Galloway, Brahman, or Zebu, Brangus, British White, Brown Swiss, Charolais, Chianina, Devon, Dexter, English Longhorn, Galloway, Gloucester, Guernsey, Hereford, or Whiteface, Highland, Holstein-Friesian, Irish Moiled, Jersey, Kerry, Limousin, Luing, Milking Devon, Milking Shorthorn, Normande, Polled Hereford, Red Angus, Red Poll, Santa Gertrudis, Shorthorn, or Durham, South Devon, Simmental, Sussex, Welsh Black, and White Park.

In some embodiments the animal is selected from the group consisting of Sheep, Goats, Deer, (including reindeer), Moose, Giraffes, Bison, Antelopes (including gazelles), Camels (including dromedaries and Bactrian camels), Yaks, Muskoxen, Water buffalo, Pronghorns, Ibexes, Chamois, Saiga antelope, Gemsbok, Wildebeest, Markhor, Sable antelope.

Additional Uses for Algae Secondary Metabolites

Different types of algae have different medicinal properties making them unique from other. They are used for various treatments and below is a small list of such algae and their medicinal cures.

*Enteromorpha*: It can be used to treat hemorrhoids, parasitic disease, goiter, coughing and bronchitis; fever reducyion capacity and ease pain.

*Acetabularia*: This can be used to treat urinary diseases and edema.

*Laminaria*: It can be used for thyroid problems and urinary diseases.

*Sargassum*: It can be used to treat cervical lymphadenitis, edema; diminishes inflammation; induces urination; contains both iodine and potassium

*Gelidium*: can be used to extract agar

*Corallina*: It can be used as pesticides

*Grateloupia*: Blood sugar lowing capability

*Gloeopeltis*: Treatment for tonsils, goitre

Applications and Future of Algal Drugs

Algal drugs are having many applications which make it a new boon for the future in drug and pharmaceutical sectors. The applications include, for example, high value oils, cosmetics, colorants, wastewater treatment, food supplements, personalized drugs, fertilizers, and forensic medicines.

In some embodiments, the extended metabolism methods of the present disclosure can be used to enhance the production of secondary metabolites for a variety of pharmaceutical, agricultural and industrial uses. Persons having skill in the art are familiar with the various applications of algae products. A non limiting list of applications include: pain management, hemorrhoid treatment, treatments of parasitic diseases, goiters, coughing and bronchitis, fever reduction, blood sugar reduction, edema reduction, and treatment of thyroid diseases, urinary diseases, and cervical lymphadenitis. Additional applications include use as a pesticide, cosmetics, colorants, wastewater treatment, food supplements, personalized drugs, fertilizers, and forensic medicines.

The disclosure will be further described by way of the following examples, which are meant to serve to assist one of ordinary skill in the art in carrying out the disclosure and are not intended in any way to limit the scope of the disclosure.

EXAMPLES

The foregoing examples of the related art and limitations related therewith are intended to be illustrative and not exclusive. Other limitations of the related art will become apparent to those of skill in the art upon a reading of the specification.

Example 1—Extended Metabolism Reactions in *Asparagopsis* spp.

*Asparagopis* spp. was obtained from an oceanic grow site and was immediately frozen for later use.

2 g of the frozen *Asparagopsis* spp. biomass was ground manually in a mortar and added to a 70 mL reaction solution comprising sodium acetate, sodium formate, sodium bromide, HEPES, and sodium bicarbonate with a pH of 7.0 (Table 4).

TABLE 4

Example reaction solution

| Ingredient | Amount |
|---|---|
| Sodium acetate | 12.2 mM |
| Sodium formate | 23.5 mM |
| Sodium bromide | 14.6 mM |
| HEPES | 16.8 mM |
| Sodium bicarbonate | 17.9 mM |

After homogenizing the mixture, 42 mL of the mixture was transferred to a control vessel and sealed, and 24 mL of the mixture was transferred to an experimental vessel. To the experimental vessel, 18 mL of 3% hydrogen peroxide was added slowly to make a 42 mL solution (a ratio of $H_2O_2$: reaction solution of between 1:1.3 and 1:1.4 in volume, or between approximately 368 and 384 mM final $H_2O_2$ concentration). The control and experimental vessels were left in the dark at room temperature for about 24 hours. Other experiments confirmed that the order of $H_2O_2$ ingredient addition did not affect outcomes, such that $H_2O_2$: reaction was added with other ingredients in the reaction solution.

Figure 3:
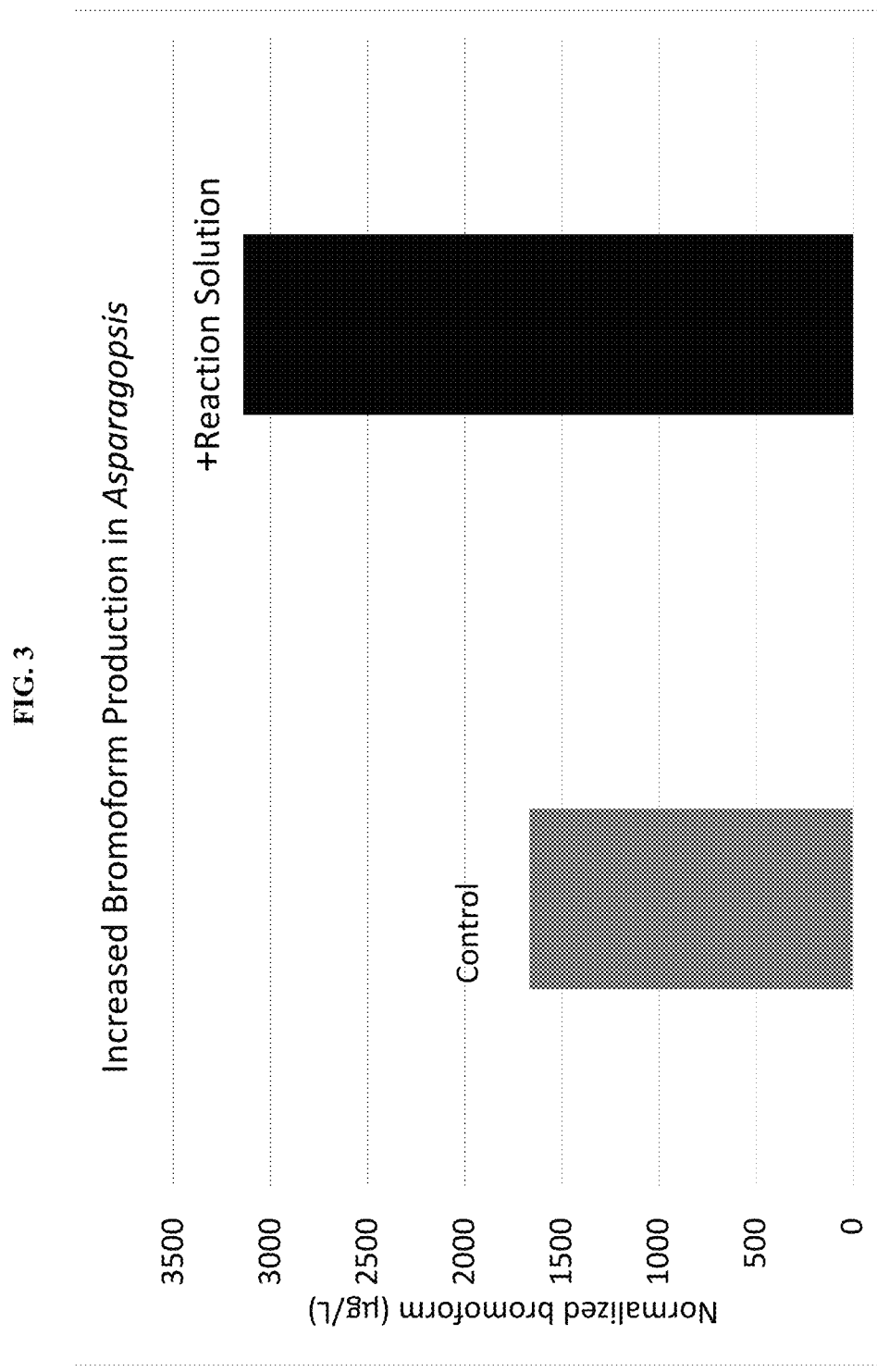
FIG. 3 is a bar graph showing increased secondary metabolite production of bromoform in *Asparagopsis* using the disclosed extended metabolism methods, compositions, and systems.

Both the mixtures from the control vessel and the experimental vessel were sent to a certified third-party lab for testing. The mixture from the control vessel had a bromoform concentration of 1019.2 µg/g dry biomass (1,664 µg/L of solution). The mixture from the experimental vessel had a bromoform concentration of 1923.3 µg/g dry biomass (3,140 µg/L of solution). Thus, the amount of bromoform was approximately double that of the control (1.89). (FIG. 3)

As hydrogen peroxide was not added to the control vessel, bromoperoxidase present in the control vessel would not have been able to catalyze the reaction to produce HOBr. Instead, the bromoform content detected in the control vessel was likely due to bromoform and/or HOBr already present in the algae. *Asparagopsis* in particular, is known for its ability to accumulate bromoform in its tissues. In the experimental vessel, the increase in bromoform content (as compared to the control vessel) would have resulted from the activity of the bromoperoxidase in catalyzing the formation of HOBr, which subsequently reacted with the other substrates (sodium acetate, sodium formate) to form secondary metabolites, including bromoform.

This experiment will be repeated, with initial bromoform measurements taken at time point 0, to be able to better measure increased production, by accounting for already existing bromoform content.

Example 2—Extended Metabolism Reactions in *Gracilaria* spp.

*Gracilaria* spp. was obtained from an oceanic grow site and was immediately frozen for later use.

To prepare the control vessel, 5.80 g of frozen *Gracilaria* spp. biomass was ground manually in a mortar and suspended in 20 mL of reaction solution (same composition as in Example 1, Table 2, above). 18 mL of distilled water was then added.

For the experimental vessel, 5.80 g of raw *Gracilaria* spp. biomass was ground manually in a mortar and suspended in 20 mL of reaction solution (with the same composition as in Example 1, Table 1 above). Instead of distilled water however, 18 mL of 3% hydrogen peroxide was added to the mixture, or approximately 418 mM final concentration. Both the experimental and control vessels were sealed and left in a dark at room temperature for about 24 hours.

Figure 4:
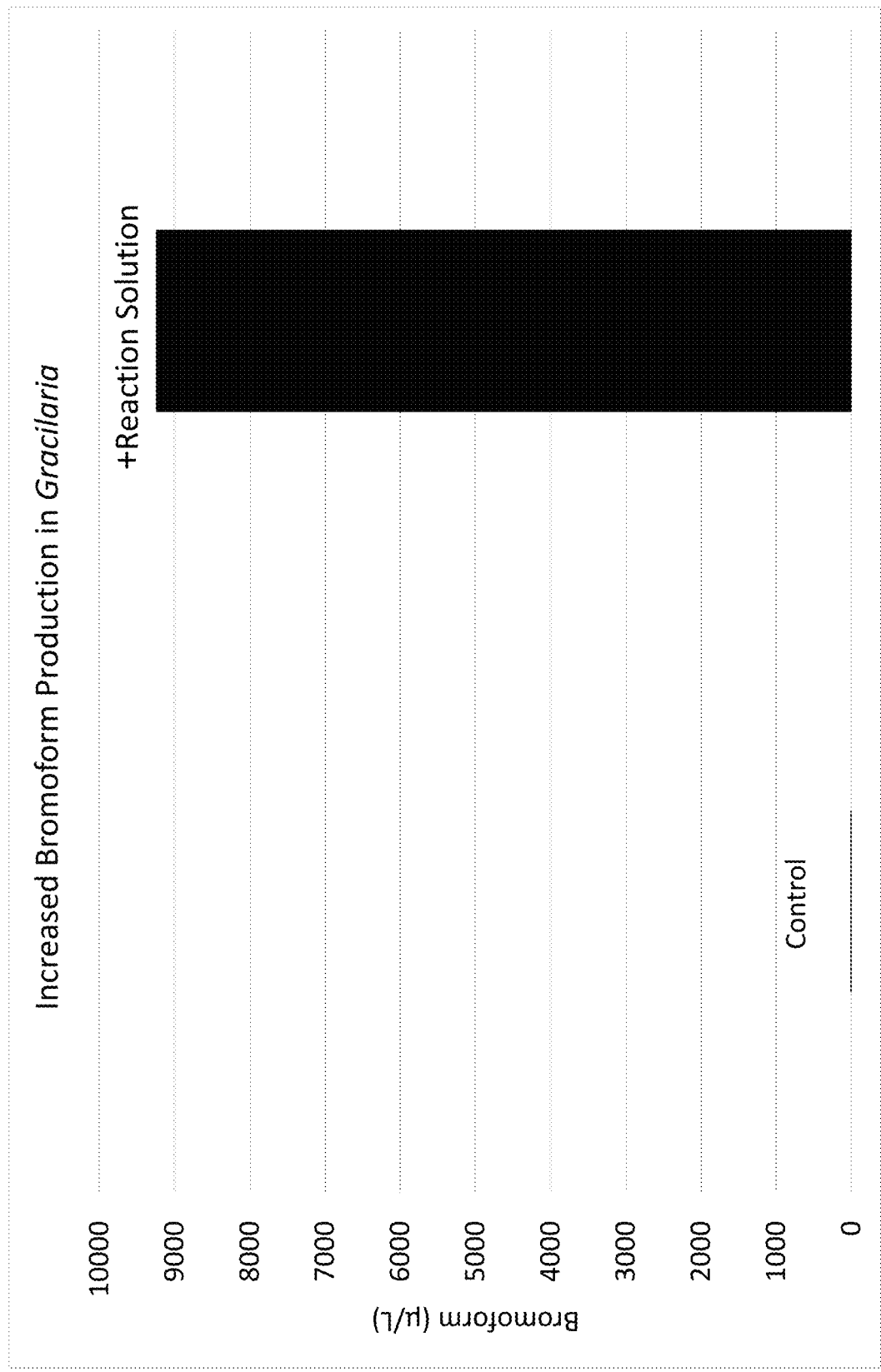
FIG. 4 is a bar graph showing increased secondary metabolite production of bromoform in *Gracilaria* using the disclosed extended metabolism methods, compositions, and systems.

Both the mixtures from the control vessel and the experimental vessel were tested for bromoform content. The mixture from the control vessel had a bromoform content of 0.85 µg/g dry biomass (13 µg/L of solution). The mixture from the experimental vessel had a bromoform concentration of 606 µg/g dry biomass (9,250 µg/L of solution), an increase of approximately 712 times compared to the control vessel (FIG. 4).

Similar to the results in Example 1, the bromoform content detected in the control vessel would have been from the bromoform and/or HOBr already present in the algae. In the experimental vessel, the increase in bromoform content (as compared to the control vessel) would have resulted from the activity of the bromoperoxidase in catalyzing the formation of HOBr, which subsequently reacted with the other substrates to form secondary metabolites, including bromoform.

Example 3—Extended Metabolism Reactions in *Macrocystis pyrifera*

*Macrocystis pyrifera* was obtained from an oceanic grow site and was immediately frozen for later use.

2.93 g of frozen *Macrocystis pyrifera* biomass was mixed with 20 mL of the reaction solution (with the same composition as in Example 1) in the control vessel. 15 mL of distilled water was added to the control vessel. For the experimental vessel, 2.93 g of raw *Macrocystis pyrifera* was mixed with 20 mL of the reaction solution (with the same composition as in Example 1). Instead of distilled water, 15 mL of 3% hydrogen peroxide solution was added to the mixture, approximately 378 mM final concentration. The experimental and control vessels were sealed and left in the dark at room temperature for an entire day.

Figure 5A:
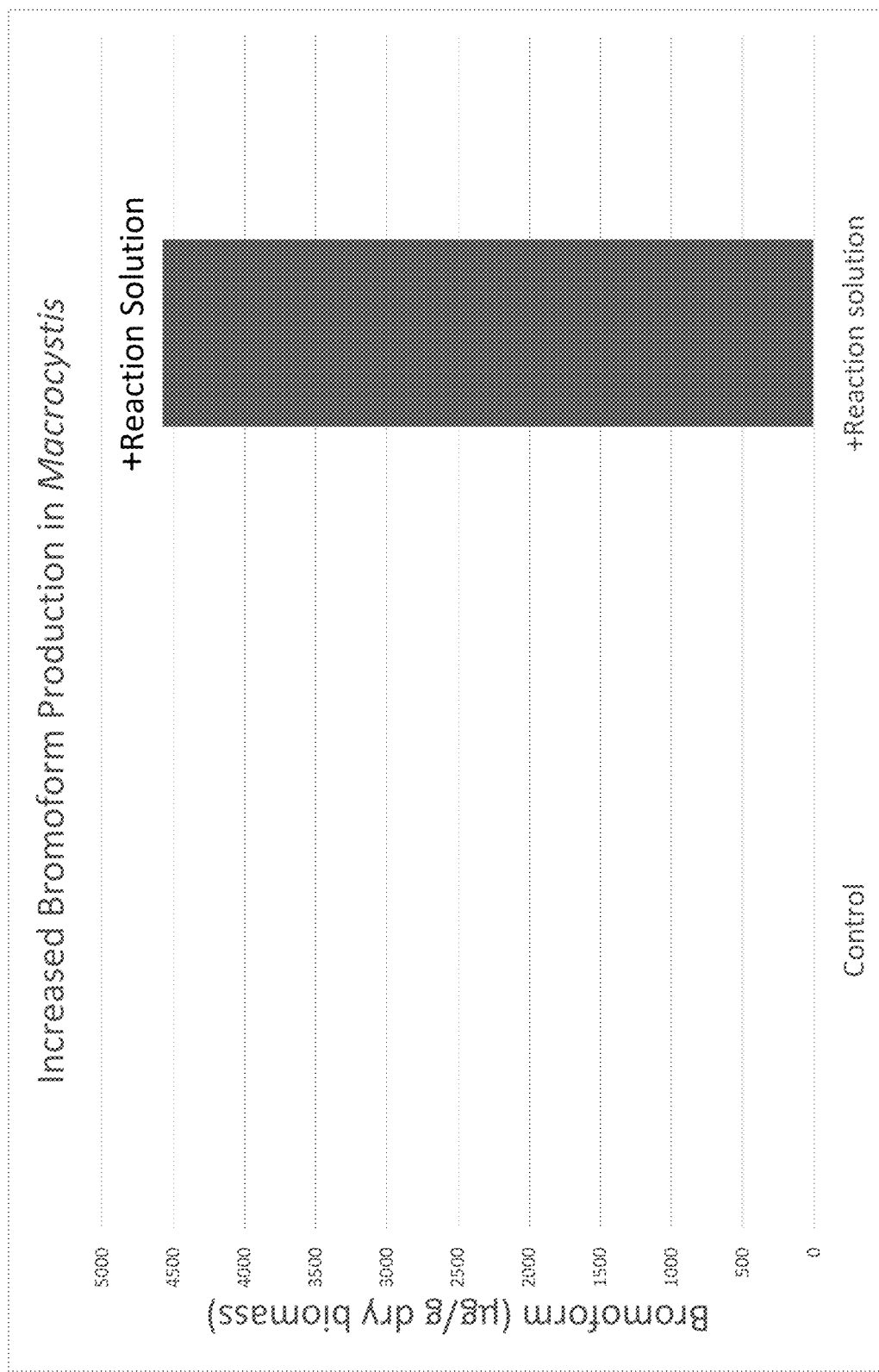
FIGS. 5A and 5B are bar graphs showing increased secondary metabolite production of bromoform production in *Macrocystis pyrifera* using the disclosed extended metabolism methods, compositions, and systems.
Figure 5B:
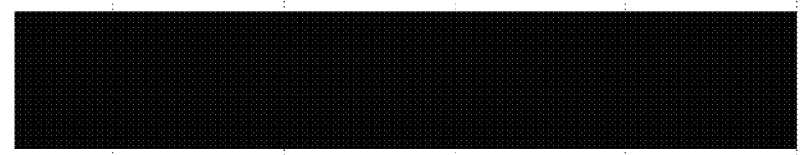

Both the mixtures from the control vessel and the experimental vessel were tested for bromoform concentration. The mixture from the control vessel had a bromoform concentration of 1.7 µg/g dry biomass. The mixture from the experimental vessel had a bromoform concentration of 4575.1 µg/g dry biomass, an increase of 2,735 times compared to the control vessel (FIG. 5A).

Figure 6:
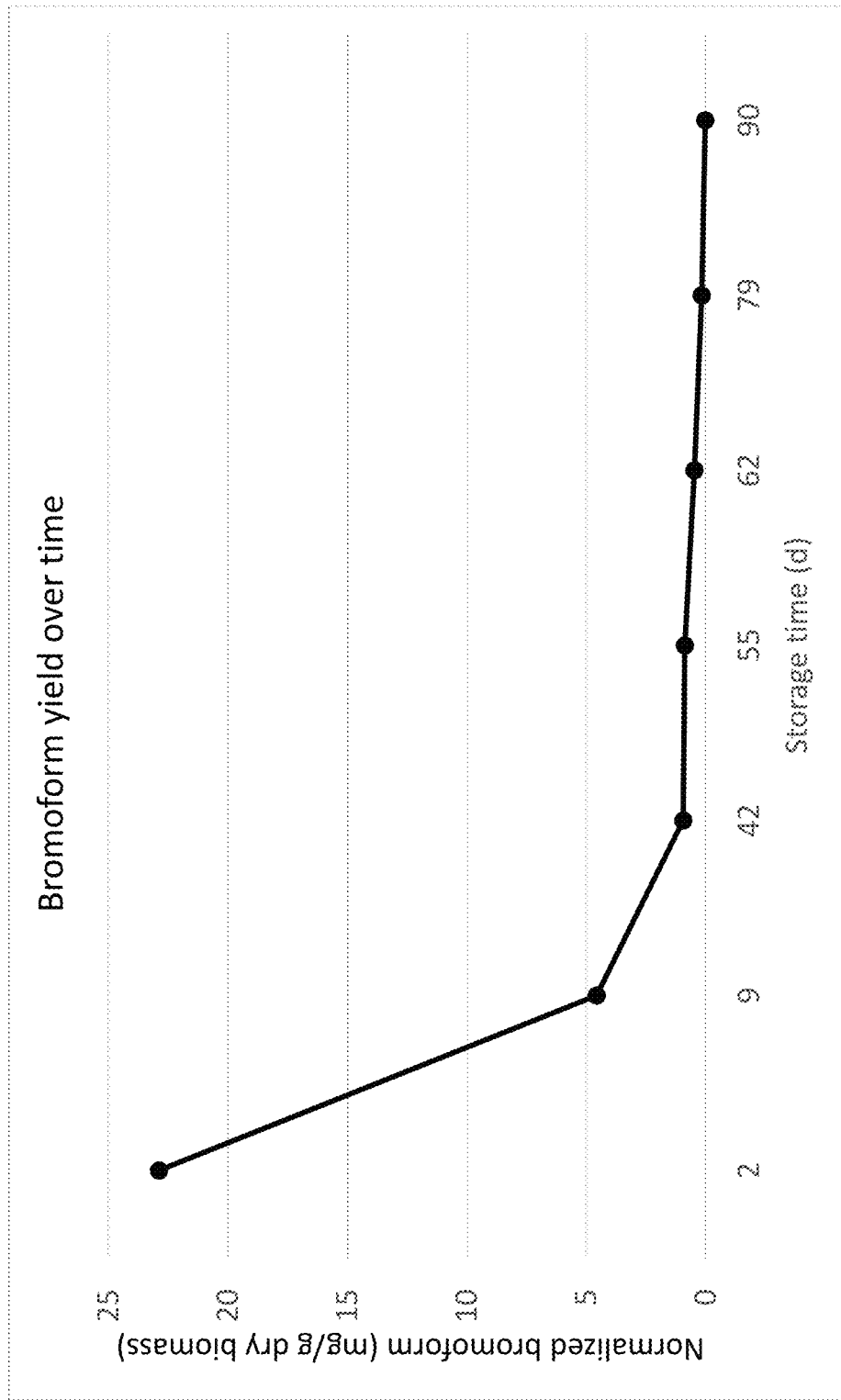
FIG. 6 is a line graph showing degradation algal biomass ability to produce secondary metabolites such as bromoform, over time in storage (mg/g dry biomass over days in storage).

In another experiment, 2.0 g frozen *Macrocystis pyrifera* biomass was mixed with 40 ml of the reaction solution (same composition as Example 1) in a glass bottle. 30 ml of 3% hydrogen peroxide solution was added to the bottle, or approximately 378 mM final concentration. After gently shaking for 2 min, the bottle was left in dark at room temperature for 24 hours before submitted to a third-party lab for bromoform testing. Control 1 included the same solution mixture but no algae biomass. Control 2 included the same reaction solution with biomass but no hydrogen peroxide. The results are shown in FIG. 6. Without any algae biomass (Control 1), the bromoform concentration is 0. Without hydrogen peroxide, the normalized bromoform concentration in the algal biomass (i.e., the background level) is 1.7 ug bromoform/g dry biomass (Control 2). When both substrate and hydrogen peroxide are provided to the algal biomass, 22.9 mg bromoform/g dry biomass (normalized) was produced, which is >13,000 times the normal yield of *Macrocystis pyrifera*.

Example 4—The Effectiveness of Extended Metabolism Reactions Rapidly Decrease with Algal Biomass Frozen Storage Time To investigate the effect of freezing the algae prior to processing with the disclosed methods, *Macrocystis pyrifera* was obtained from an oceanic grow site and was immediately frozen for later use.

At two, nine, 42, 55, 62, 79, and 90 days post freezing, samples of biomass were taken and mixed with 40 ml of the reaction solution (same composition as Example 1, freshly prepared each time) in a glass bottle. 30 ml of 3% hydrogen peroxide solution was added to the bottle, or approximately 378 mM final concentration. After gently shaking for 2 min, the bottle was left in dark at room temperature for 24 hours before submitted to a third-party lab for bromoform testing.

As shown in FIG. 6, bromoform yield dropped significantly between two and nine days post freezing. Bromoform yield continued to decrease with time in frozen storage, suggesting that the bromoperoxidase present in the algae cells loses activity. Fresh, never frozen algae, or recently frozen algae thus present the best algal biomass or source of enzyme for the extended metabolism experiments.

Example 5—Inducing Extended Metabolism in a Mixed Culture of Cyanobacteria

While haloperoxidases have been traditionally found in macroalgae, the inventors hypothesized that microalgae and cyanobacteria also utilize haloperoxidases and are capable of forming antimethanogenic compounds.

Three microalgae strains, obtained from UTEX algae collection centre, namely *Chlorella protothecoides* (UTEX 1806), *Chlorella vulgaris* (UTEX 2714) and *Spirulina-Arthrospira platensis* (UTEX LB 2340) were grown together in an inorganic medium with added bromide (65 mg/L). After the culture density achieved 1 g dry biomass/L, 60 ml of the mixed culture was centrifuged at 5000 rpm for 5 min. The supernatant was removed, and 24 ml of reaction solution (Table 4) and 16 ml 3% hydrogen peroxide (approximately 353 mM final concentration) was added to the tube containing the pellet of biomass. The sample was left in dark at room temperature for about 24 hours before being submitted to a third-party lab for bromoform testing. A control background reaction without the reaction solution was also run. The results showed that the background bromoform was nearly 0, while the normalized bromoform concentration in the experimental sample was 0.17 mg bromoform/g dry biomass, demonstrating the extended metabolism can be applied to organisms not previously identified as producers of antimethanogenic compounds.

Example 6—Bromoform Production Varies Based on Type of Substrate

To examine the contributions of different substrates in bromoform production, an experiment was carried out testing different compounds in the same reaction solution, using identical procedures (Table 5). Frozen *Macrocystis* spp. was used for the algal biomass.

TABLE 5

Substrates for Extending Metabolism

| | Algae biomass | $H_2O_2$ | Bromide | Formate | Acetate | Acetone |
|---|---|---|---|---|---|---|
| 1 | x | — | — | — | — | — |
| 2 | x | x | — | — | — | — |
| 3 | x | x | x | — | — | — |
| 4 | x | x | x | x | — | — |
| 5 | x | x | x | — | x | — |
| 6 | x | x | x | — | — | x |

As shown in Table 5 above, six different reactions were completed. Reaction 1 only comprised only algae biomass (and distilled water). Reaction 2 comprised algae biomass and hydrogen peroxide. Reaction 3 comprised algae biomass, hydrogen peroxide, and bromide. Reaction 4 comprised algae biomass, hydrogen peroxide, bromide, and formate. Reaction 5 comprised algae biomass, hydrogen peroxide, bromide, and acetate. Lastly, reaction 6 comprised algae biomass, hydrogen peroxide, bromide, and acetone.

Figure 7:
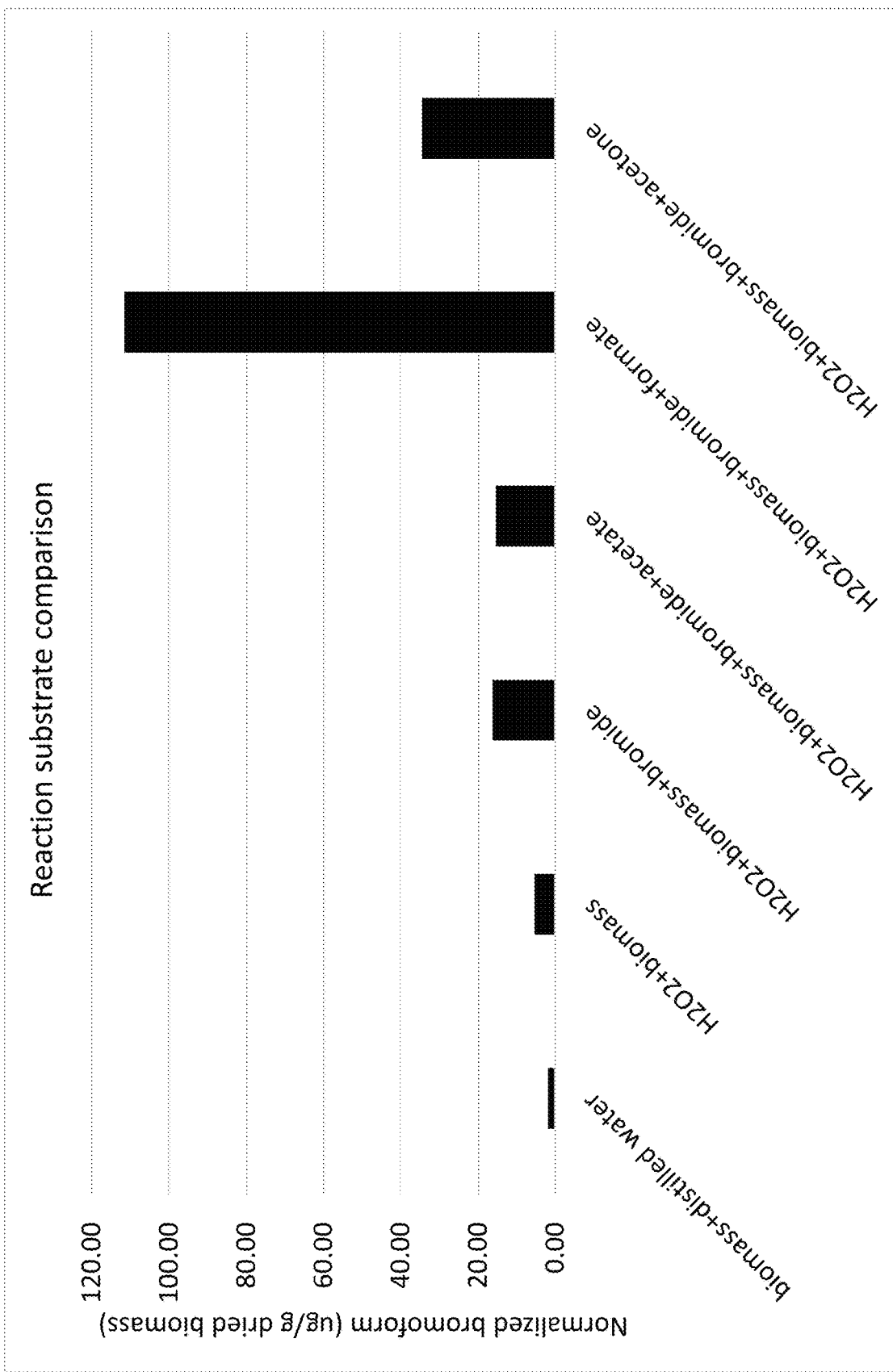
FIG. 7 is a bar graph showing secondary metabolite bromoform production with various substrates.

The results are shown in FIG. 7 as normalized micrograms of bromoform produced per gram of dried biomass. Reaction 1 shows the level of background bromoform concentration originating from the algae biomass alone, which is <5 µg/g dried biomass. Adding hydrogen peroxide (reaction 2) makes use of the stored organic carbon and bromide available within the algae biomass and nearly doubles the amount of bromoform. With the addition of bromide, (reaction 3), the amount of bromoform produced is further increased 2-fold over reaction 2. Surprisingly, when individual substrates (acetate, formate, or acetone) were added to the algae biomass, hydrogen peroxide, and bromide mix, formate (reaction 4) produced far more bromoform than either acetate or acetone (FIG. 7).

Example 7—Substrates for Extending Metabolism and Increasing Metabolite Concentrations of the Present Disclosure are Superior to Those Previously Disclosed This example will compare bromoform production with the presently disclosed VFA substrates versus others proposed substrates described in the art. Specifically, this example will measure bromoform production using acetate, acetone, or formate compared against i) sea water with organic runoff; ii) 5 (pentane-2,4-dione), and iii) 6 (heptane 2,4,6-trione). The contributions of these substrates in bromoform production is evaluated in otherwise identical reaction solutions using identical procedures (Table 6). Any of the algal biomasses of the present disclosure can be used for this experiment, for example, *Macrocystis* spp.

TABLE 6

Substrates for Extending Metabolism and Increasing Metabolite and Bioactives Concentrations

| | Algae biomass | $H_2O_2$ | Bromide | Formate | Acetate | Acetone | Sea Water Organics | 5 (pentane-2,4-dione) | 6 (heptane 2,4,6-trione) |
|---|---|---|---|---|---|---|---|---|---|
| 1 | X | X | X | X | — | — | — | — | — |
| 2 | X | X | X | — | X | — | — | — | — |
| 3 | X | X | X | — | — | X | — | — | — |
| 4 | X | X | X | — | — | — | X | — | — |
| 5 | X | X | X | — | — | — | — | X | — |
| 6 | X | X | X | — | — | — | — | — | X |

The results from this experiment are expected to show that acetate, acetone, and/or formate are superior to other tested substrates.

Example 8—Additional Substrates Extending Metabolism

This example will evaluate additional substrates within the extended metabolism method of the present disclosure. Specifically, this example will measure bromoform production using a substrate selected from methanol, formaldehyde, formic acid, urine, ethanol, acetaldehyde, acetic acid, glycolic acid, ethylene glycol, glyoxal, oxalic acid, methoxymethane, methyl formate, 1-Propanol, Isopropanol, Propylene glycol, 1,3-propanediol, Glycerin, Propionaldehyde, Malondialdehyde, malonic acid, pyruvic acid, Mesoxalic acid, Tartronic acid, Methoxyethane, 2-Methoxyethanol, Ethyl formate, methyl acetate, Butanol, Isobutanol, tert-Butanol, 2-Butanol, 1,2-Butanediol, 1,3-Butanediol, 1,4-Butanediol, 2,3-Butanediol, 2-Methyl-1,2-propanediol, 2-Methyl-1,3-propanediol, 2-Methyl-2,4-pentanediol, 1,2,3-Butanetriol, 1,2,4-Butanetriol, 1,3,4-Butanetriol, Erythritol, Butyraldehyde, Succinaldehyde, Isobutyraldehyde, Methyl Ethyl Ketone, Diacetyl, α-Ketobutyric acid, butyric acid, Isobutyric acid, Acetoacetic acid, 4-oxobutanoate, 3-Hydroxy3-formyl propanoic acid, 3-oxobutanoic acid, Succinic Acid, Maleic acid, Fumaric acid, Methoxypropane, Diethyl ether, Methyl propionate, Dimethyl malonate, propyl formate, isopropyl formate, butyl formate, methyl butyrate, ethyl acetate, dimethyl oxalate, Acetonedicarboxylic acid, Glucose, Fructose, Sucrose, Lactose, Maltose, Galactose, Ribose, Xylose, Mannose, sobutyric acid, Valeric acid, Isovaleric acid, Caproic acid, Caprylic acid, Capric acid, Lauric acid, Lactic acid, Citric acid, Pyruvate, Succinate, Oxaloacetate, α-Ketoglutaric acid, Fumarate, Malate, Glutamate, Dimethyl sulfoxide, Sorbitol, Gluconic acid, Methanesulfonic acid, Polyethylene glycol, and combinations thereof. Each of these substrates will be tested with other ingredients described herein for the reaction solution (e.g., hydrogen peroxide and a halide, such as bromide).

The contributions of these substrates on bromoform production will be evaluated in otherwise identical reaction solutions using identical procedures. Any of the algal biomasses of the present disclosure can be used for this experiment, for example, *Macrocystis* spp.

Example 9—Extended Metabolism with Other Halides

Other examples in this application have show the value of extended metabolism across different organisms, with different reaction solutions, and different algal processing. These examples have used bromide as the halogen substrate.

After reviewing these results, persons having skill in the art will recognize however that extended metabolism can be used to incorporate additional halides for the production of secondary metabolites, such as antimethanogenic compounds.

This example will thus measure the production of antimethanogenic compounds in extended metabolism reactions with reaction solutions that are identical except for the type of halide that is included. Specifically, reaction solutions with hydrogen peroxide, a VFA such as formate, and pH buffer, will be conducted using bromide, iodide, chloride, fluoride, and/or mixtures thereof as the halide. Endpoints of this experiment will review profiles of produced secondary metabolites, including the concentrations of bromoform, chloroform, iodoform, and/or fluoroform. Any of the algal biomasses of the present disclosure can be used for this experiment, for example, *Macrocystis* spp.

Results are expected to show that the extended metabolism reactions of the present disclosure are also effective with chloride, iodide, and/or fluoride as the halide in the reaction solution.

Example 10—Reduced Enteric Methane Emissions from Ruminant Animals

The antimethanogenic compounds and compositions described herein can be administered to ruminant animals, such as cattle, to reduce enteric methane emissions. For example, the extracted antimethanogenic compound or composition can be used as a feed additive, added directly to the food (as a so-called top-dress). When used as a feed additive, additional ingredients may be added enhance the flavor, nutrition, and/or shelf life. The antimethanogenic compound or composition may also be incorporated in the manufacture of compounded animal feeds or lick blocks.

Depending on the ruminant animal, the antimethanogenic compound or composition may be administered continuously, every hour, every day, every other day, once a week, etc., in a range from 0.01 mg to 1200 mg per kg of the animal's body weight.

As the ruminant animal consumes the antimethanogenic compound or composition, enteric methane emissions may be reduced from 1% to 100% compared to other ruminant animals fed the same unsupplemented diet.

Example 11—Methane Reducing Properties of Full Spectrum Extracts vs Purified Bromoform This example tests the antimethanogenic properties of full spectrum bromoform-containing products produced from the methods of the present disclosure, vs commercially-available bromoform products. For example, the full spectrum antimethanogenic compositions obtained by methods of the present disclosure will be administered to a population of ruminants (e.g., a population of cows). Commercially-available bromoform will be administered to a control population of ruminants. Both the control and test populations of ruminants will be monitored over several weeks, to measure feed consumption, weight gain, and methane emissions.

It is expected that the full spectrum bromoform-containing products will exhibit greater potency compared to the control commercial product Example 12—Additional Haloperoxidase Sequences and Organisms that Express Them Sequence databases within the National Center for Biotechnology Information were searched for additional haloperoxidase enzymes. These enzymes are expected to be compatible with the reaction solution methods of the present disclosure, and also helpful in identifying organisms amenable to the extended metabolism techniques described herein. The NCBI query was based on sequence annotation, to capture all sequences with predicted or confirmed haloperoxidase activity. Relevant hits from this search are provided below. Sequences and related publication information for each hit are available on the NCBA database via the Gene Identifier listed in Table 7.

TABLE 7

Additional Haloperoxidases in NCBI Sequence Databases

| Gene ID | Species | Gene ID | Species |
|---|---|---|---|
| Additional Identified Bromoperoxidases | | | |
| 54313346 | *Aspergillus lentulus* | 115960874 | *Quercus lobata* |
| 102717292 | *Oryza brachyantha* | 112516644 | *Cynara cardunculus* subsp. *cardunculus* |
| 45022953 | *Bacillus anthracis* str. 'Ames Ancestor' | 887535 | *Mycobacterium tuberculosis* H37Rv |
| 67467506 | *Bacillus thuringiensis* serovar *berliner* ATCC 10792 | 17325528 | *Chondrus crispus* |
| 56652888 | *Bacillus tropicus* | 17321997 | *Chondrus crispus* |
| 72449796 | *Bacillus cereus* | 17321963 | *Chondrus crispus* |
| 58158692 | *Bacillus albus* | 17318615 | *Chondrus crispus* |
| 8078634 | *Sorghum bicolor* | | |
| Additional Identified Chloroperoxidases | | | |
| 6341748 | *Pyrenophora tritici-repentis* Pt-1C-BFP | 81614593 | *Penicillium angulare* |
| 62200662 | *Alternaria burnsii* | 81588150 | *Penicillium hordei* |
| 117634072 | *Prunus dulcis* | 81559590 | *Penicillium crustosum* |
| 20667641 | *Heterobasidion irregulare* TC 32-1 | 81458646 | *Penicillium concentricum* |
| 20666955 | *Heterobasidion irregulare* TC 32-1 | 81416404 | *Penicillium coprophilum* |
| 13402220 | *Zymoseptoria tritici* IPO323 | 81410199 | *Penicillium bovifimosum* |
| 20638368 | *Phytophthora sojae* | 77782213 | *Diaporthe amygdali* |
| 36869124 | *Rhizophagus irregularis* DAOM 181602 = DAOM 197198 | 76142726 | *Pisolithus orientalis* |
| 36859406 | *Rhizophagus irregularis* DAOM 181602 = DAOM 197198 | 76142721 | *Pisolithus orientalis* |
| 56021682 | *Lasiodiplodia theobromae* | 76137492 | *Pisolithus orientalis* |
| 56021043 | *Lasiodiplodia theobromae* | 76136671 | *Pisolithus orientalis* |
| 56013312 | *Lasiodiplodia theobromae* | 70312844 | *Fusarium solani* |
| 11511481 | *Thermothelomyces thermophilus* ATCC 42464 | 70306896 | *Fusarium solani* |
| 54547931 | *Westerdykella ornata* | 70304113 | *Fusarium solani* |
| 54478924 | *Neohortaea acidophila* | 70300150 | *Fusarium solani* |
| 54471877 | *Neohortaea acidophila* | 70282200 | *Ilyonectria robusta* |
| 54471591 | *Neohortaea acidophila* | 70282090 | *Ilyonectria robusta* |
| 38140329 | *Aspergillus welwitschiae* | 70277962 | *Ilyonectria robusta* |

TABLE 7-continued

Additional Haloperoxidases in NCBI Sequence Databases

| Gene ID | Species | Gene ID | Species |
| --- | --- | --- | --- |
| 38135837 | Aspergillus welwitschiae | 70276638 | Ilyonectria robusta |
| 19264597 | Metarhizium robertsii ARSEF 23 | 70266695 | Lentinula edodes |
| 19262545 | Metarhizium robertsii ARSEF 23 | 70265802 | Lentinula edodes |
| 19262259 | Metarhizium robertsii ARSEF 23 | 70263075 | Lentinula edodes |
| 19255362 | Metarhizium robertsii ARSEF 23 | 70263074 | Lentinula edodes |
| 19255264 | Metarhizium robertsii ARSEF 23 | 70259102 | Lentinula edodes |
| 20377788 | Wallemia ichthyophaga EXF-994 | 70256932 | Lentinula edodes |
| 56016027 | Lasiodiplodia theobromae | 70255794 | Lentinula edodes |
| 28741979 | Phialophora attae | 70243261 | Talaromyces proteolyticus |
| 28733225 | Phialophora attae | 70225243 | Fusarium redolens |
| 28732381 | Phialophora attae | 70224334 | Fusarium redolens |
| 27364281 | Rhodotorula toruloides NP11 | 70222185 | Fusarium redolens |
| 20668257 | Heterobasidion irregulare TC 32-1 | 70221696 | Fusarium redolens |
| 20667158 | Heterobasidion irregulare TC 32-1 | 70218958 | Fusarium redolens |
| 20666471 | Heterobasidion irregulare TC 32-1 | 70214709 | Fusarium redolens |
| 19890356 | Beauveria bassiana ARSEF 2860 | 70205624 | Alternaria rosae |
| 18759021 | Drepanopeziza brunnea f. sp. 'multigermtubi' MB m1 | 70197880 | Alternaria rosae |
| 2681280 | Pyricularia oryzae 70-15 | 70194280 | Alternaria rosae |
| 35407607 | Fusarium fujikuroi IMI 58289 | 70191584 | Microdochium trichocladiopsis |
| 35403921 | Fusarium fujikuroi IMI 58289 | 70191456 | Microdochium trichocladiopsis |
| 35399139 | Fusarium fujikuroi IMI 58289 | 70180934 | Microdochium trichocladiopsis |
| 35396219 | Fusarium fujikuroi IMI 58289 | 70180414 | Microdochium trichocladiopsis |
| 35395609 | Fusarium fujikuroi IMI 58289 | 70178871 | Microdochium trichocladiopsis |
| 28850296 | Pochonia chlamydosporia 170 | 70176238 | Boeremia exigua |
| 28848718 | Pochonia chlamydosporia 170 | 70176046 | Boeremia exigua |
| 26247897 | Metarhizium brunneum ARSEF 3297 | 70175162 | Boeremia exigua |
| 26247835 | Metarhizium brunneum ARSEF 3297 | 70162149 | Fusarium flagelliforme |
| 26246542 | Metarhizium brunneum ARSEF 3297 | 70159786 | Fusarium flagelliforme |
| 26244399 | Metarhizium brunneum ARSEF 3297 | 70154635 | Fusarium flagelliforme |
| 20656926 | Phytophthora sojae | 70151662 | Fusarium flagelliforme |
| 20644425 | Phytophthora sojae | 70138030 | Truncatella angustata |
| 20643672 | Phytophthora sojae | 70137730 | Truncatella angustata |
| 20641761 | Phytophthora sojae | 70136280 | Truncatella angustata |
| 20641760 | Phytophthora sojae | 70133946 | Truncatella angustata |
| 20639518 | Phytophthora sojae | 70132801 | Truncatella angustata |
| 20638530 | Phytophthora sojae | 70129225 | Truncatella angustata |
| 20637847 | Phytophthora sojae | 70129007 | Truncatella angustata |
| 19245086 | Metarhizium acridum CQMa 102 | 70125019 | Truncatella angustata |
| 18085499 | Agaricus bisporus var. bisporus H97 | 63788153 | Protomyces lactucae-debilis |
| 30993622 | Hyphopichia burtonii NRRL Y-1933 | 63787785 | Protomyces lactucae-debilis |

TABLE 7-continued

Additional Haloperoxidases in NCBI Sequence Databases

| Gene ID | Species | Gene ID | Species |
|---|---|---|---|
| 18834081 | Dichomitus squalens LYAD-421 SS1 | 63787499 | Protomyces lactucae-debilis |
| 54488292 | Pseudovirgaria hyperparasitica | 63786951 | Protomyces lactucae-debilis |
| 54475232 | Neohortaea acidophila | 63784753 | Protomyces lactucae-debilis |
| 54473205 | Neohortaea acidophila | 63784752 | Protomyces lactucae-debilis |
| 54307438 | Arthroderma uncinatum | 63784074 | Protomyces lactucae-debilis |
| 42060762 | Fusarium proliferatum ET1 | 63778763 | Pseudomassariella vexata |
| 42058833 | Fusarium proliferatum ET1 | 63775974 | Pseudomassariella vexata |
| 42054016 | Fusarium proliferatum ET1 | 63775887 | Pseudomassariella vexata |
| 42052061 | Fusarium proliferatum ET1 | 63775773 | Pseudomassariella vexata |
| 42051710 | Fusarium proliferatum ET1 | 63773736 | Pseudomassariella vexata |
| 42050274 | Fusarium proliferatum ET1 | 62163171 | Colletotrichum karsti |
| 42049379 | Fusarium proliferatum ET1 | 62161327 | Colletotrichum karsti |
| 42048776 | Fusarium proliferatum ET1 | 43669294 | Aspergillus pseudonomiae |
| 39622382 | Alternaria arborescens | 43668779 | Aspergillus pseudonomiae |
| 36516707 | [Candida] sorbophila | 43658436 | Aspergillus caelatus |
| 35604713 | Ramularia collocygni | 43654665 | Aspergillus caelatus |
| 35604296 | Ramularia collocygni | 43652011 | Aspergillus caelatus |
| 35595757 | Ramularia collocygni | 43647005 | Aspergillus pseudotamarii |
| 35428454 | Cercospora beticola | 43635670 | Aspergillus pseudotamarii |
| 35426798 | Cercospora beticola | 43633611 | Aspergillus alliaceus |
| 31019246 | Diplodia corticola | 43628479 | Aspergillus alliaceus |
| 31014766 | Diplodia corticola | 43623514 | Aspergillus alliaceus |
| 31013105 | Diplodia corticola | 36408963 | Plasmopara halstedii |
| 25276119 | Exophiala aquamarina CBS 119918 | 36408879 | Plasmopara halstedii |
| 20351476 | Gaeumannomyces tritici R3-111a-1 | 36407354 | Plasmopara halstedii |
| 19196600 | Cladophialophora psammophila CBS 110553 | 36402574 | Plasmopara halstedii |
| 18671292 | Fomitiporia mediterranea MF3/22 | 36401937 | Plasmopara halstedii |
| 10030898 | Nannizzia gypsea CBS 118893 | 28872846 | Colletotrichum higginsianum IMI 349063 |
| 9229326 | Microsporum canis CBS 113480 | 28866137 | Colletotrichum higginsianum IMI 349063 |
| 4983615 | Aspergillus niger CBS 513.88 | 28866136 | Colletotrichum higginsianum IMI 349063 |
| 4355094 | Aspergillus terreus NIH2624 | 28862650 | Colletotrichum higginsianum IMI 349063 |
| 882669 | Pseudomonas aeruginosa PAO1 | 28862314 | Colletotrichum higginsianum IMI 349063 |
| 77727696 | Dioszegia hungarica | 28860867 | Colletotrichum higginsianum IMI 349063 |
| 70297431 | Emericellopsis atlantica | 11848540 | Klebsiella pneumoniae subsp. pneumoniae HS11286 |
| 27682723 | Penicillium expansum | 71988863 | Fulvia fulva |
| 27680933 | Penicillium expansum | 69015489 | Colletotrichum gloeosporioides |
| 27674126 | Penicillium expansum | 63827683 | Laetiporus sulphureus 93-53 |
| 77700261 | Fimicolochytrium jonesii | 63821229 | Laetiporus sulphureus 93-53 |
| 77698770 | Fimicolochytrium jonesii | 62300705 | Cantharellus anzutake |
| 69017181 | Colletotrichum gloeosporioides | 62297830 | Cantharellus anzutake |
| 63742193 | Metarhizium album ARSEF 1941 | 59365656 | Colletotrichum truncatum |

TABLE 7-continued

Additional Haloperoxidases in NCBI Sequence Databases

| Gene ID | Species | Gene ID | Species |
|---|---|---|---|
| 63740451 | Metarhizium album ARSEF 1941 | 59365560 | Colletotrichum truncatum |
| 62301158 | Cantharellus anzutake | 59310034 | Fusarium subglutinans |
| 62300708 | Cantharellus anzutake | 59297158 | Fusarium tjaetaba |
| 62298585 | Cantharellus anzutake | 55981540 | Colletotrichum scovillei |
| 62296633 | Cantharellus anzutake | 28886660 | Purpureocillium lilacinum |
| 62295612 | Cantharellus anzutake | 72059317 | Xylaria bambusicola |
| 62292040 | Cantharellus anzutake | 81913775 | Penicillium waksmanii |
| 59364414 | Colletotrichum truncatum | 81803916 | Penicillium subrubescens |
| 59321768 | Fusarium subglutinans | 81759761 | Penicillium manginii |
| 59320648 | Fusarium subglutinans | 81729046 | Penicillium macrosclerotiorum |
| 59313400 | Fusarium subglutinans | 81630002 | Penicillium hispanicum |
| 59311180 | Fusarium subglutinans | 81377860 | Penicillium cosmopolitanum |
| 59306558 | Fusarium tjaetaba | 77784716 | Diaporthe amygdali |
| 59305551 | Fusarium tjaetaba | 77783934 | Diaporthe amygdali |
| 59302394 | Fusarium tjaetaba | 74441550 | Penicillium oxalicum |
| 59295810 | Fusarium tjaetaba | 73326215 | Colletotrichum spaethianum |
| 72126316 | Neoantrodia serialis | 71971672 | Psilocybe cubensis |
| 72001055 | Rhodofomes roseus | 70285044 | Ilyonectria robusta |
| 77769964 | Zychaea mexicana | 70199065 | Alternaria rosae |
| 77762523 | Zychaca mexicana | 62161241 | Colletotrichum karsti |
| 75927545 | Mucor mucedo | 59277067 | Colletotrichum siamense |
| 75906157 | Gilbertella persicaria | 59275196 | Colletotrichum siamense |
| 75891909 | Radiomyces spectabilis | 59248986 | Colletotrichum aenigma |
| 75890706 | Radiomyces spectabilis | 59246928 | Colletotrichum aenigma |
| 75867049 | Halteromyces radiatus | 28871486 | Colletotrichum higginsianum IMI 349063 |
| 75848433 | Cokeromyces recurvatus | 28870601 | Colletotrichum higginsianum IMI 349063 |
| 75786756 | Hypoxylon trugodes | 28867000 | Colletotrichum higginsianum IMI 349063 |
| 72052326 | Xylaria bambusicola | 28861119 | Colletotrichum higginsianum IMI 349063 |
| 64717581 | Suillus bovinus | 19412291 | Trametes versicolor FP-101664 SS1 |
| 64716781 | Suillus bovinus | 121790842 | Salvia splendens |
| 64712191 | Suillus bovinus | 121749619 | Salvia splendens |
| 64712190 | Suillus bovinus | 121748173 | Salvia splendens |
| 64708829 | Suillus bovinus | 120672359 | Panicum virgatum |
| 64706935 | Suillus bovinus | 110893716 | Helianthus annuus |
| 64698821 | Suillus discolor | 108868769 | Brassica rapa |
| 64697993 | Suillus discolor | 106451123 | Brassica napus |
| 64695914 | Suillus discolor | 103320565 | Prunus mume |
| 64694724 | Suillus discolor | 25011547 | Sinorhizobium meliloti GR4 |
| 64692007 | Suillus discolor | 105221006 | Zeugodacus cucurbitae |
| 64690611 | Suillus discolor | 104767019 | Camelina sativa |
| 64690608 | Suillus discolor | 821299 | Arabidopsis thaliana |
| 64684315 | Suillus subalutaceus | 80350794 | Nocardia wallacei |
| 64683443 | Suillus subalutaceus | 80331671 | Nocardia otitidiscaviarum |
| 64682880 | Suillus subalutaceus | 80330954 | Nocardia otitidiscaviarum |
| 64675912 | Suillus subalutaceus | 61151589 | Nocardia seriolae |
| 64673567 | Suillus subalutaceus | 41369732 | Nitrosospira multiformis ATCC 25196 |
| 64666546 | Suillus fuscotomentosus | 68114800 | Naegleria fowleri |
| 64666536 | Suillus fuscotomentosus | 59330422 | Letharia lupina |
| 64659471 | Suillus fuscotomentosus | 59294466 | Letharia columbiana |
| 64659214 | Suillus fuscotomentosus | 54584887 | Trematosphaeria pertusa |
| 64655174 | Suillus fuscotomentosus | 54430191 | Lindgomyces ingoldianus |

TABLE 7-continued

Additional Haloperoxidases in NCBI Sequence Databases

| Gene ID | Species | Gene ID | Species |
|---------|---------|---------|---------|
| 64654657 | Suillus fuscotomentosus | 19398599 | Exserohilum turcica Et28A |
| 64654009 | Suillus clintonianus | 41960409 | Pyricularia grisea |
| 64653109 | Suillus clintonianus | 40736361 | Pyricularia pennisetigena |
| 64650494 | Suillus clintonianus | 25840836 | Bipolaris maydis ATCC 48331 |
| 64645140 | Suillus clintonianus | 19134423 | Bipolaris sorokiniana ND90Pr |
| 64642933 | Suillus clintonianus | 814646 | Arabidopsis thaliana |
| 64642597 | Suillus clintonianus | 18808160 | Stereum hirsutum FP-91666 SS1 |
| 64639669 | Suillus clintonianus | 18806171 | Stereum hirsutum FP-91666 SS1 |
| 64635511 | Suillus subaureus | 18805520 | Stereum hirsutum FP-91666 SS1 |
| 64633871 | Suillus subaureus | 18800652 | Stereum hirsutum FP-91666 SS1 |
| 64632329 | Suillus subaureus | 18798189 | Stereum hirsutum FP-91666 SS1 |
| 64632298 | Suillus subaureus | 18794460 | Stereum hirsutum FP-91666 SS1 |
| 64630389 | Suillus subaureus | 838072 | Arabidopsis thaliana |
| 64622356 | Suillus paluster | 828351 | Arabidopsis thaliana |
| 64621875 | Suillus paluster | 821350 | Arabidopsis thaliana |
| 64620854 | Suillus paluster | 8863483 | Naegleria gruberi |
| 64620312 | Suillus paluster | 19316222 | Pseudozyma flocculosa PF-1 |
| 64614739 | Suillus paluster | 18762016 | Drepanopeziza brunnea f. sp. 'multigermtubi' MB m1 |
| 64614229 | Suillus paluster | 18761359 | Drepanopeziza brunnea f. sp. 'multigermtubi' MB m1 |
| 64605375 | Suillus plorans | 3503887 | Aspergillus fumigatus Af293 |
| 64599917 | Suillus plorans | 65094584 | Fusarium mangiferae |
| 64599916 | Suillus plorans | 65092576 | Fusarium mangiferae |
| 64593664 | Suillus plorans | 65087929 | Fusarium mangiferae |
| 64593136 | Suillus plorans | 65086071 | Fusarium mangiferae |
| 64592188 | Suillus plorans | 65085789 | Fusarium mangiferae |
| 81934620 | Penicillium samsonianum | 65083567 | Fusarium mangiferae |
| 81906211 | Penicillium vulpinum | 65082958 | Fusarium mangiferae |
| 81896865 | Penicillium soppii | 59345446 | Mycena indigotica |
| 81877757 | Penicillium robsamsonii | 20386016 | Trypanosoma grayi |
| 81827813 | Penicillium paradoxum | 20384265 | Trypanosoma grayi |
| 81823757 | Penicillium paradoxum | 20379449 | Trypanosoma grayi |
| 81741167 | Penicillium malachiteum | 20378682 | Trypanosoma grayi |
| 81648380 | Penicillium brevicompactum | 20378681 | Trypanosoma grayi |
| 17354454 | Chlorella variabilis | 24101541 | Fibroporia radiculosa |
| 18817009 | Serpula lacrymans var. lacrymans S7.9 | | |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

Numbered Embodiments of the Disclosure

Notwithstanding the appended claims, the disclosure sets forth the following numbered embodiments:

1. A method for producing a secondary metabolite in algae, said method comprising the steps of:
   a) providing an algal biomass;
   b) providing a reaction solution, said reaction solution comprising:
      i) a volatile fatty acid;
      ii) hydrogen peroxide;
      ii) a halide; and
   c) contacting the algal biomass with the reaction solution for a time period sufficient to synthesize the secondary metabolite;

wherein the algal biomass in the reaction solution produces higher quantities of the secondary metabolite than a comparable algal biomass without the reaction solution.
2. The method of embodiment 1, wherein the algal biomass is selected from live algae, fresh algae, thawed algae, and combinations thereof.
3. The method of embodiment 1, wherein the algal biomass is selected from dead algae, lysed algae, freeze-dried algae, and combinations thereof.
4. The method of any one of embodiments 1-3, wherein the algal biomass comprises macroalgae.
5. The method of any one of embodiments 1-3, wherein the algal biomass comprises microalgae.
6. The method of any one of embodiments 1-3, wherein the algal biomass comprises red algae of the order Rhodophyta.
7. The method of any one of embodiments 1-3, wherein the algal biomass comprises red algae of the order Bonnemaisoniales.
8. The method of any one of embodiments 1-3, wherein the algal biomass comprises red algae of the genus *Asparagopsis*.
9. The method of any one of embodiments 1-3, wherein the algal biomass comprises algae selected from the group consisting of: algae of class Florideophyceae, algae of genus *Gracilaria*, algae of genus *Palmeria*, and genus *Chondrus*.
10. The method of any one of embodiments 1-3, wherein the algal biomass comprises brown algae of class Phaeophyceae.
11. The method of any one of embodiments 1-3, wherein the algal biomass comprises green algae.
12. The method of any one of embodiments 1-3, wherein the algal biomass comprises an algae selected from the group consisting of *Laminaria, Macrocystis pyrifera* and *Dichtyota*.
13. The method of any one of embodiments 1-12, wherein the algal biomass comprises haloperoxidase.
14. The method of embodiment 13, wherein the haloperoxidase is a bromoperoxidase.
15. The method of embodiment 13, wherein the haloperoxidase is an iodoperoxidase.
16. The method of embodiment 13, wherein the haloperoxidase is a chloroperoxidase.
17. The method of any one of embodiments 13-16, wherein the haloperoxidase is a vanadium-dependent haloperoxidase.
18. The method of any one of embodiments 13-17, wherein the haloperoxidase shares at least 80%, 85%, 90%, 95%, 97%, 98%, 99%, or 100% sequence identity with a peptide selected from Table 3.
19. The method of any one of embodiments 1-2 or 4-18, comprising exposing said algal biomass to an environmental stress.
20. The method of embodiment 19, wherein the environmental stress is selected from the group consisting of, increased acidity, reduced acidity, reduced oxygen content, cold stress, heat stress, and light stress.
21. The method of embodiment 19 or 20, wherein the environmental stress is reduced oxygen content in aqueous solution containing algal biomass.
22. The method of embodiment 21, wherein reduced oxygen content is less than one ppm dissolved oxygen.
23. The method of any one of embodiments 1-22, wherein the ratio of algal biomass to reaction solution is between 1:1 and 1:50.
24. The method of any one of embodiments 1-22, wherein the ratio of algal biomass to reaction solution is between 1:2 and 1:4.
25. The method of any one of embodiments 1-24, wherein the contacting the algal biomass with the reaction solution occurs at a temperature between 5° C. and 40° C.
26. The method of any one of embodiments 1-24, wherein the contacting the algal biomass with the reaction solution occurs at a temperature between 15° C. and 35° C.
27. The method of any one of embodiments 1-24, wherein the contacting the algal biomass with the reaction solution occurs at a temperature between 20° C. and 30° C.
28. A method for producing a secondary metabolite, said method comprising the steps of:
    a) providing a haloperoxidase enzyme;
    b) providing a reaction solution, said reaction solution comprising:
        i) a volatile fatty acid;
        ii) hydrogen peroxide;
        iii) a halide; and
    c) contacting the peroxidase enzyme with the reaction solution for a time period sufficient to synthesize a secondary metabolite.
29. The method of embodiment 28, wherein the haloperoxidase selected from bromoperoxidase, iodoperoxidase, chloroperoxidase, a fluoroperoxidase, and combinations thereof.
30. The method of embodiment 28 or 29, wherein the haloperoxidase is selected from a vanadium-dependent haloperoxidase, and heme iron-dependent haloperoxidase.
30.1 The method of embodiment 28 or 29, wherein the haloperoxidase is s non-heme haloperoxidase.
31. The method of any one of embodiments 28-30.1, wherein the haloperoxidase is a recombinant peroxidase.
32. The method of any one of embodiments 1-31, wherein the halide is selected from fluoride, bromide, iodide, chloride, and combinations thereof.
33. The method of any one of embodiments 1-31, wherein the halide is selected from sodium bromide, sodium chloride, potassium chloride, sodium fluoride, potassium bromide, potassium chloride, potassium iodide, potassium fluoride, calcium bromide, calcium chloride, calcium iodide, calcium fluoride, and combinations thereof.
34. The method of any one of embodiments 1-33, wherein the secondary metabolite is a methyl halide.
35. The method of any one of embodiments 1-34, wherein the secondary metabolite is an antimethanogenic compound.
36. The method of any one of embodiments 1-35, wherein the secondary metabolite is selected from methyl bromide, methyl chloride, methyl iodide, methyl fluoride, bromodichlormethane, trichlorethylene, bromoform, chloroform, iodoform, fluoroform, dibromomethane, and combinations thereof.
37. The method of any one of embodiments 1-36, wherein the volatile fatty acid comprises acetate.
38. The method of any one of embodiments 1-36, wherein the volatile fatty acid comprises acetone.
39. The method of any one of embodiments 1-36, wherein the volatile fatty acid comprises formate.

40. The method of any one of embodiments 1-36, wherein the volatile fatty acid comprises acetate and formate.
41. The method of embodiment 37 or 40, wherein the acetate is selected from the group consisting of, sodium acetate, potassium acetate, aluminum acetate, and ammonium acetate.
42. The method of embodiment 37 or 40, wherein the acetate is sodium acetate or potassium acetate.
43. The method of embodiment 37 or 40, wherein the acetate is sodium acetate.
44. The method of embodiment 39 or 40, wherein the formate is sodium formate or potassium formate.
45. The method of any one of embodiments 1-36, wherein the halide is bromide, the volatile fatty acid is formate, and the metabolite is bromoform.
46. The method of any one of embodiments 1-36, wherein the halide is chloride, the volatile fatty acid is formate, and the metabolite is chloroform.
47. The method of any one of embodiments 1-36, wherein the halide is iodide, the volatile fatty acid is formate, and the metabolite is iodoform.
48. The method of any one of embodiments 1-36, wherein the halide is fluoride, the volatile fatty acid is formate, and the metabolite is fluoroform.
49. The method of any one of embodiments 1-48, wherein the reaction solution comprises at least 1 mM of the volatile fatty acid.
50. The method of any one of embodiments 1-48, wherein the reaction solution comprises at least 2.4 mM of the volatile fatty acid.
51. The method of any one of embodiments 1-48, wherein the reaction solution comprises at least 10 mM of the volatile fatty acid.
52. The method of any one of embodiments 1-48, wherein the reaction solution comprises between 1 mM and 40 mM of the volatile fatty acid.
53. The method of any one of embodiments 1-48, wherein the reaction solution comprises between 40 mM and 80 mM of the volatile fatty acid.
54. The method of any one of embodiments 1-48, wherein the reaction solution comprises between 80 mM and 120 mM of the volatile fatty acid.
55. The method of any one of embodiments 1-48, wherein the reaction solution comprises between 120 mM and 200 mM of the volatile fatty acid.
56. The method of any one of embodiments 1-48, wherein the reaction solution comprises at least 200 mM of the volatile fatty acid.
57. The method of any one of embodiments 1-48, wherein the reaction solution comprises at least 500 mM of the volatile fatty acid.
58. The method of any one of embodiments 1-48, wherein the reaction solution comprises at least 1 M of the volatile fatty acid.
59. The method of any one of embodiments 1-58, wherein the reaction solution comprises between 1 mM and 1 M hydrogen peroxide.
60. The method of any one of embodiments 1-58, wherein the reaction solution comprises at between 100 mM and 400 mM hydrogen peroxide.
61. The method of any one of embodiments 1-58, wherein the reaction solution comprises about 300 mM hydrogen peroxide.
62. The method of any one of embodiments 1-61, wherein the reaction solution has a pH of at least 5.0.
63. The method of embodiment 62, wherein the reaction solution has a pH between 6.0 and 7.8.
64. The method of embodiment 62, wherein the reaction solution has a pH between 5.0 and 11.0.
65. The method of any one of embodiments 1-64, wherein the time period is at least 30 minutes.
66. The method of any one of embodiments 1-59, wherein the time period is at least 90 minutes.
67. The method of any one of embodiments 1-59, wherein the time period is at least 6 hours.
68. The method of any one of embodiments 1-59, wherein the time period is at least 12 hours.
69. The method of any one of embodiments 1-59, wherein the time period is at least 18 hours.
70. The method of any one of embodiments 1-59, wherein the time period is at least 24 hours.
71. The method of any one of embodiments 1-59, wherein the time period is at least 36 hours.
72. The method of any one of embodiments 1-66, comprising the step of enriching the secondary metabolite from the reaction solution.
73. The method of any one of embodiments 1-67, comprising the step of separating the secondary metabolite from the reaction solution.
74. The method of any one of embodiments 1-67, wherein a layer of oil is added on top of the reaction solution.
75. The method of embodiment 74, wherein the oil is selected from canola oil, olive oil, corn oil, mineral oil, soybean oil, corn oil, palm kernel oil, rapeseed oil, sunflower oil, safflower oil, coconut oil, rice bran oil, sesame oil, flaxseed oil, hemp oil, cottonseed oil, peanut oil, almond oil, beech nut oil, brazil nut oil, cashew oil, hazelnut oil, macadamia oil, mongongo nut oil, pecan oil, pine nut oil, pistachio oil, walnut oil, pumpkin seed oil, grapefruit seed oil, lemon oil, apricot oil, apple seed oil, argan oil, avocado oil, orange oil, and combinations thereof.
76. The method of embodiment 74 or 75, wherein the oil layer accumulates the secondary metabolite.
77. The method of any one of embodiments 74-76, comprising the step of collecting oil from the oil layer, wherein said oil layer comprises the secondary metabolite.
78. The method of any one of embodiments 1-27 or 32-77, wherein the method produces at least 0.1 mg of secondary metabolite per gram of biomass.
79. The method of any one of embodiments 1-27 or 32-77, wherein the method produces at least 10 mg of secondary metabolite per gram of biomass.
80. The method of any one of embodiments 1-27 or 32-77, wherein the method produces at least 100 mg of secondary metabolite per gram of biomass.
81. The method of any one of embodiments 1-27 or 32-77, wherein the method produces at least 1000 mg of secondary metabolite per gram of biomass.
82. The method of any one of embodiments 1-81, comprising the step of formulating the metabolite.
83. The method of any one of embodiments 28-77, wherein the method produces at least 1.1 mg of secondary metabolite per mg of haloperoxidase enzyme.
84. The method of any one of embodiments 28-77, wherein the method produces at least 10 mg of secondary metabolite per mg of haloperoxidase enzyme.
85. The method of any one of embodiments 28-77, wherein the method produces at least 100 mg of secondary metabolite per mg of haloperoxidase enzyme.

86. The method of any one of embodiments 28-77, wherein the method produces at least 1000 mg of secondary metabolite per mg of haloperoxidase enzyme.

87. The method of any one of embodiments 1-86, comprising the step of formulating the metabolite.

88. A composition comprising:
   a) an algal biomass;
   b) a reaction solution, said reaction solution comprising:
      i) a volatile fatty acid;
      ii) hydrogen peroxide;
      iii) a halide; and
   c) a secondary metabolite.

89. The composition of embodiment 88, wherein the algal biomass is selected from live algae, fresh algae, thawed algae, and combinations thereof.

90. The composition of embodiment 88, wherein the algal biomass is selected from dead algae, lysed algae, freeze-dried algae, and combinations thereof.

91. The composition of any one of embodiments 88-90, wherein the algal biomass comprises macroalgae.

92. The composition of any one of embodiments 88-90, wherein the algal biomass comprises microalgae.

93. The composition of any one of embodiments 88-90, wherein the algal biomass comprises red algae of the order Rhodophyta.

94. The composition of any one of embodiments 88-90, wherein the algal biomass comprises red algae of the order Bonnemaisoniales.

95. The composition of any one of embodiments 88-90, wherein the algal biomass comprises red algae of the genus *Asparagopsis*.

96. The composition of any one of embodiments 88-90, wherein the algal biomass comprises algae selected from the group consisting of: algae of class Florideophyceae, algae of genus *Gracilaria*, algae of genus *Palmeria*, and genus *Chondrus*.

97. The composition of any one of embodiments 88-90, wherein the algal biomass comprises brown algae of class Phaeophyceae.

98. The composition of any one of embodiments 88-90, wherein the algal biomass comprises green algae.

99. The composition of any one of embodiments 88-90, wherein the algal biomass comprises an algae selected from the group consisting of *Laminaria, Macrocystis pyrifera* and *Dichtyota*.

100. The composition of any one of embodiments 88-99, wherein the algal biomass comprises haloperoxidase.

101. The composition of embodiment 100, wherein the haloperoxidase is a bromoperoxidase.

102. The composition of embodiment 100, wherein the haloperoxidase is an iodoperoxidase.

103. The composition of embodiment 100, wherein the haloperoxidase is a chloroperoxidase.

104. The composition of embodiment 100, wherein the haloperoxidase is a recombinant peroxidase or a synthetic peroxidase.

105. The composition of any one of embodiments 100-104, wherein the haloperoxidase is a vanadium-dependent haloperoxidase.

106. The composition of any one of embodiments 100-105, wherein the haloperoxidase shares at least 80%, 85%, 90%, 95%, 97%, 98%, 99%, or 100% sequence identity with a peptide selected from Table 3.

107. The composition of any one of embodiments 88-106, wherein the ratio of algal biomass to reaction solution is between 1:1 and 1:50.

108. The composition of any one of embodiments 88-106, wherein the ratio of algal biomass to reaction solution is between 1:2 and 1:4.

109. The composition of any one of embodiments 88-108, wherein the halide is selected from fluoride, bromide, iodide, chloride, and combinations thereof.

110. The composition of any one of embodiments 88-108, wherein the halide is selected from sodium bromide, sodium chloride, potassium chloride, sodium fluoride, potassium bromide, potassium chloride, potassium iodide, potassium fluoride, calcium bromide, calcium chloride, calcium iodide, calcium fluoride, and combinations thereof.

111. The composition of any one of embodiments 88-110, wherein the secondary metabolite is a methyl halide.

112. The composition of any one of embodiments 88-111, wherein the secondary metabolite is an antimethanogenic compound.

113. The composition of any one of embodiments—88-112, wherein the secondary metabolite is selected from methyl bromide, methyl chloride, methyl iodide, methyl fluoride, bromodichlormethane, trichlorethylene, bromoform, chloroform, iodoform, fluoroform, dibromomethane, and combinations thereof 114. The composition of any one of embodiments 88-113, wherein the volatile fatty acid comprises acetate.

115. The composition of any one of embodiments 88-113, wherein the volatile fatty acid comprises acetone.

116. The composition of any one of embodiments 88-113, wherein the volatile fatty acid comprises formate.

117. The composition of any one of embodiments 88-113, wherein the volatile fatty acid comprises acetate and formate.

118. The composition of embodiment 114 or 117, wherein the acetate is selected from the group consisting of, sodium acetate, potassium acetate, aluminum acetate, and ammonium acetate.

119. The composition of embodiment 114 or 117, wherein the acetate is sodium acetate or potassium acetate.

120. The composition of embodiment 114 or 117, wherein the acetate is sodium acetate.

121. The composition of embodiment 116 or 117, wherein the formate is sodium formate or potassium formate.

122. The composition of any one of embodiments 88-121, wherein the halide is bromide, the volatile fatty acid is formate, and the metabolite is bromoform.

123. The composition of any one of embodiments 88-121, wherein the halide is chloride, the volatile fatty acid is formate, and the metabolite is chloroform.

124. The composition of any one of embodiments 88-121, wherein the halide is iodide, the volatile fatty acid is formate, and the metabolite is iodoform.

125. The composition of any one of embodiments 88-121, wherein the halide is fluoride, the volatile fatty acid is formate, and the metabolite is fluoroform.

126. The composition of any one of embodiments 88-125, wherein the reaction solution comprises at least 1 mM of the volatile fatty acid.

127. The composition of any one of embodiments 88-125, wherein the reaction solution comprises at least 2.4 mM of the volatile fatty acid.

128. The composition of any one of embodiments 88-125, wherein the reaction solution comprises at least 10 mM of the volatile fatty acid.

129. The composition of any one of embodiments 88-125, wherein the reaction solution comprises between 1 mM and 40 mM of the volatile fatty acid.
130. The composition of any one of embodiments 88-125, wherein the reaction solution comprises between 40 mM and 80 mM of the volatile fatty acid.
131. The composition of any one of embodiments 88-125, wherein the reaction solution comprises between 80 mM and 120 mM of the volatile fatty acid.
132. The composition of any one of embodiments 88-125, wherein the reaction solution comprises between 120 mM and 200 mM of the volatile fatty acid.
133. The composition of any one of embodiments 88-125, wherein the reaction solution comprises at least 200 mM of the volatile fatty acid.
134. The composition of any one of embodiments 88-125, wherein the reaction solution comprises at least 500 mM of the volatile fatty acid.
135. The composition of any one of embodiments 88-125, wherein the reaction solution comprises at least 1 M of the volatile fatty acid.
136. The composition of any one of embodiments 88-135, wherein the reaction solution comprises at least 1 mM hydrogen peroxide.
137. The composition of any one of embodiments 88-135, wherein the reaction solution comprises at least 5 mM hydrogen peroxide.
138. The composition of any one of embodiments 88-135, wherein the reaction solution comprises at between 2 mM and 200 mM hydrogen peroxide.
139. The composition of any one of embodiments 88-138, wherein the reaction solution has a pH of at least 5.0.
140. The composition of embodiment 139, wherein the reaction solution has a pH between 6.0 and 7.8.
141. The composition of embodiment 139, wherein the reaction solution has a pH between 5.0 and 11.0.
142. The composition of any one of embodiments 88-141, further comprising an oil.
143. The composition of embodiment 142, wherein the oil is selected from canola oil, olive oil, corn oil, mineral oil, soybean oil, corn oil, palm kernel oil, rapeseed oil, sunflower oil, safflower oil, coconut oil, rice bran oil, sesame oil, flaxseed oil, hemp oil, cottonseed oil, peanut oil, almond oil, beech nut oil, brazil nut oil, cashew oil, hazelnut oil, macadamia oil, mongongo nut oil, pecan oil, pine nut oil, pistachio oil, walnut oil, pumpkin seed oil, grapefruit seed oil, lemon oil, apricot oil, apple seed oil, argan oil, avocado oil, orange oil, and combinations thereof.
144. An algal cultivation system comprising:
    a) an algal biomass;
    b) an algal growth substrate; and
    c) an oil layer.
145. The algal cultivation system of embodiment 144, wherein the oil layer comprises a secondary metabolite.
146. The algal cultivation system of embodiment 145, wherein the secondary metabolite is a methyl halide.
147. The algal cultivation system of embodiment 145, wherein the secondary metabolite is an antimethanogenic compound.
148. The algal cultivation system of embodiment 145, wherein the secondary metabolite is selected from methyl bromide, methyl chloride, methyl iodide, methyl fluoride, bromodichlormethane, trichlorethylene, bromoform, chloroform, iodoform, fluoroform, dibromomethane, and combinations thereof.
149. The algal cultivation system of any one of embodiments 144-148, wherein the oil layer is capable of removing the secondary metabolite from the algal growth substrate.
150. The algal cultivation system of any one of embodiments 144-149, wherein the oil the oil is selected from canola oil, olive oil, corn oil, mineral oil, soybean oil, corn oil, palm kernel oil, rapeseed oil, sunflower oil, safflower oil, coconut oil, rice bran oil, sesame oil, flaxseed oil, hemp oil, cottonseed oil, peanut oil, almond oil, beech nut oil, brazil nut oil, cashew oil, hazelnut oil, macadamia oil, mongongo nut oil, pecan oil, pine nut oil, pistachio oil, walnut oil, pumpkin seed oil, grapefruit seed oil, lemon oil, apricot oil, apple seed oil, argan oil, avocado oil, orange oil, and combinations thereof.
151. The algal cultivation system of any one of embodiments 144-150, wherein the algal growth substrate comprises:
    i) osmotic regulator;
    ii) a carbon source; and
    iii) nutrient mix.
152. The algal cultivation system of embodiment 151, wherein the osmotic regulator is a salt.
153. The algal cultivation system of embodiment 152, wherein the salt is selected from sodium chloride, sodium carbonate, ammonium chloride, sodium acetate, sodium bromide, potassium cyanide, zinc chloride hydroxide, potassium chlorate, calcium phosphate, sodium nitrate, potassium cerium fluoride, potassium chloride, sodium bicarbonate, phosphate buffer, and combinations thereof.
154. The algal cultivation system of any one of embodiments 151-153, wherein the osmotic regulator maintains a salinity of between 10 and 50 parts per thousand.
155. The algal cultivation system of embodiment 154, wherein the salinity is between 33 and 37 parts per thousand.
156. The algal cultivation system of any one of embodiments 151-155, wherein the nutrient mix comprises a nitrogen source and a phosphorus source.
157. The algal cultivation system of embodiment 156, wherein the nitrogen source is nitrate, ammonium, urea, amino acids, or combinations thereof.
158. The algal cultivation system of embodiment 156, wherein the phosphorus source is dihydrogen phosphate, hydrogen phosphate, phosphate, or combinations thereof.
159. The algal cultivation system of any one of embodiments 151-155, wherein the nutrient mix comprises waste material.
160. The algal cultivation system of embodiment 159, wherein the waste material is wastewater, sewage, raw sewage, liquefied solid waste, washing water, grey water, drainage, black water, industrial effluvia, residential effluvia, commercial effluvia, or combinations thereof.
161. The algal cultivation system of any one of embodiments 151-155, wherein the nutrient mix comprises food processing by-products, sugar solutions, starch solutions, wort, mash, malt, grist, agar, or combinations thereof.
162. The algal cultivation system of any one of embodiments 151-161, wherein the carbon source carbon dioxide, bicarbonate, carbonic acid, carbonate, or combinations thereof 163. The algal cultivation system of any one of embodiments 151-162, comprising:
    a reaction solution, said reaction solution comprising:
        i) a volatile fatty acid;
        ii) hydrogen peroxide; and
        iii) a halide.
164. The algal cultivation system of any one of embodiments 144-163, wherein the algal biomass comprises macroalgae.
165. The algal cultivation system of any one of embodiments 144-163, wherein the algal biomass comprises microalgae.
166. The algal cultivation system of any one of embodiments 144-163, wherein the algal biomass comprises red algae of the order Rhodophyta.
167. The algal cultivation system of any one of embodiments 144-163, wherein the algal biomass comprises red algae of the order Bonnemaisoniales.
168. The algal cultivation system of any one of embodiments 144-163, wherein the algal biomass comprises red algae of the genus *Asparagopsis*.
169. The algal cultivation system of any one of embodiments 144-163, wherein the algal biomass comprises algae selected from the group consisting of: algae of class Florideophyceae, algae of genus *Gracilaria*, algae of genus *Palmeria*, and genus *Chondrus*.
170. The algal cultivation system of any one of embodiments 144-163, wherein the algal biomass comprises brown algae of class Phaeophyceae.
171. The algal cultivation system of any one of embodiments 144-163, wherein the algal biomass comprises green algae.
172. The algal cultivation system of any one of embodiments 144-163, wherein the algal biomass comprises an algae selected from the group consisting of *Laminaria*, *Macrocystis pyrifera* and *Dichtyota*.
173. The algal cultivation system of any one of embodiments 144-163, wherein the algal biomass comprises haloperoxidase.
174. The algal cultivation system of any one of embodiments 163-173, wherein the halide is selected from fluoride, bromide, iodide, chloride, and combinations thereof.
175. The algal cultivation system of any one of embodiments 163-173, wherein the halide is selected from sodium bromide, sodium chloride, potassium chloride, sodium fluoride, potassium bromide, potassium chloride, potassium iodide, potassium fluoride, calcium bromide, calcium chloride, calcium iodide, calcium fluoride, and combinations thereof
176. The algal cultivation system of any one of embodiments 163-175, wherein the volatile fatty acid comprises acetate.
177. The algal cultivation system of any one of embodiments 163-175, wherein the volatile fatty acid comprises acetone.
178. The algal cultivation system of any one of embodiments 163-175, wherein the volatile fatty acid comprises formate.
179. The algal cultivation system of any one of embodiments 163-175, wherein the volatile fatty acid comprises acetate and formate.
180. The algal cultivation system of embodiment 178 or 179, wherein the acetate is selected from the group consisting of, sodium acetate, potassium acetate, aluminum acetate, and ammonium acetate.
181. The algal cultivation system of embodiment 176 or 179, wherein the acetate is sodium acetate or potassium acetate.
182. The algal cultivation system of embodiment 176 or 179, wherein the acetate is sodium acetate.
183. The algal cultivation system of embodiment 178 or 179, wherein the formate is sodium formate or potassium formate.
184. The algal cultivation system of any one of embodiments 163-175, wherein the halide is bromide, the volatile fatty acid is formate, and the metabolite is bromoform.
185. The algal cultivation system of any one of embodiments 163-175, wherein the halide is chloride, the volatile fatty acid is formate, and the metabolite is chloroform.
186. The algal cultivation system of any one of embodiments 163-175, wherein the halide is iodide, the volatile fatty acid is formate, and the metabolite is iodoform.
187. The algal cultivation system of any one of embodiments 163-175, wherein the halide is fluoride, the volatile fatty acid is formate, and the metabolite is fluoroform.
188. The algal cultivation system of any one of embodiments 163-187, wherein the reaction solution comprises at least 1 mM of the volatile fatty acid.
189. The algal cultivation system of any one of embodiments 163-187, wherein the reaction solution comprises at least 2.4 mM of the volatile fatty acid.
190. The algal cultivation system of any one of embodiments 163-187, wherein the reaction solution comprises at least 10 mM of the volatile fatty acid.
191. The algal cultivation system of any one of embodiments 163-187, wherein the reaction solution comprises between 1 mM and 40 mM of the volatile fatty acid.
192. The algal cultivation system of any one of embodiments 163-187, wherein the reaction solution comprises between 40 mM and 80 mM of the volatile fatty acid.
193. The algal cultivation system of any one of embodiments 163-187, wherein the reaction solution comprises between 80 mM and 120 mM of the volatile fatty acid.
194. The algal cultivation system of any one of embodiments 163-187, wherein the reaction solution comprises between 120 mM and 200 mM of the volatile fatty acid.
195. The algal cultivation system of any one of embodiments 163-187, wherein the reaction solution comprises at least 200 mM of the volatile fatty acid.
196. The algal cultivation system of any one of embodiments 163-187, wherein the reaction solution comprises at least 500 mM of the volatile fatty acid.
197. The algal cultivation system of any one of embodiments 163-187, wherein the reaction solution comprises at least 1 M of the volatile fatty acid.
198. The algal cultivation system of any one of embodiments 163-197, wherein the reaction solution comprises at least 1 mM hydrogen peroxide.
199. The algal cultivation system of any one of embodiments 163-197, wherein the reaction solution comprises at least 5 mM hydrogen peroxide.

200. The algal cultivation system of any one of embodiments 163-197, wherein the reaction solution comprises at between 2 mM and 200 mM hydrogen peroxide.
201. A method for extracting a secondary metabolite from algae, the method comprising the steps of:
   a) providing an algal biomass; and
   b) exposing said algal biomass to an environmental stress,
   wherein said environmental stress induces the algae to release the secondary metabolite into surrounding environment, thereby allowing extraction of the secondary metabolite.
202. The method of embodiment 201, wherein the environmental stress is selected from the group consisting of, increased acidity, reduced acidity, reduced oxygen content, cold stress, heat stress, osmotic shock, and light stress.
203. The method of embodiment 202, wherein the environmental stress is reduced oxygen content in aqueous solution containing algal biomass.
204. The method of embodiment 203, wherein reduced oxygen content is less than one ppm dissolved oxygen.
205. The method of any one of embodiments 201-204, wherein the algal biomass comprises macroalgae.
206. The method of any one of embodiments 201-204, wherein the algal biomass comprises microalgae.
207. The method of any one of embodiments 201-204, wherein the algal biomass comprises red algae of the order Rhodophyta.
208. The method of any one of embodiments 201-204, wherein the algal biomass comprises red algae of the order Bonnemaisoniales.
209. The method of any one of embodiments 201-204, wherein the algal biomass comprises red algae of the genus *Asparagopsis*.
210. The method of any one of embodiments 201-204, wherein the algal biomass comprises algae selected from the group consisting of: algae of class Florideophyceae, algae of genus *Gracilaria*, algae of genus *Palmeria*, and genus *Chondrus*.
211. The method of any one of embodiments 201-204, wherein the algal biomass comprises brown algae of class Phaeophyceae.
212. The method of any one of embodiments 201-204, wherein the algal biomass comprises green algae.
213. The method of any one of embodiments 201-204, wherein the algal biomass comprises an algae selected from the group consisting of *Laminaria, Macrocystis pyrifera* and *Dichtyota*.
214. The method of any one of embodiments 201-213, wherein the method produces at least a 1.5-fold increase in the secondary metabolite compared to non-stressed algal.
215. The method of any one of embodiments 201-2013, wherein the method produces at least a 2-fold increase in the secondary metabolite compared to non-stressed algal.
216. The method of any one of embodiments 201-213, wherein the method produces at least a 3-fold increase in the secondary metabolite compared to non-stressed algal.
217. The method of any one of embodiments 201-216, wherein the secondary metabolite is a methyl halide.
218. The method of any one of embodiments 201-216, wherein the secondary metabolite is an antimethanogenic compound.
219. The method of any one of embodiments 201-216, wherein the secondary metabolite is selected from methyl bromide, methyl chloride, methyl iodide, methyl fluoride, bromodichlormethane, trichlorethylene, bromoform, chloroform, iodoform, fluoroform, dibromomethane, and combinations thereof.
220. The method of any one of embodiments 1-87, the composition of any one of embodiments 88-143, or the algal cultivation system of any one of embodiments 163-200, wherein the volatile fatty acid is a substrate selected from methanol, formaldehyde, formic acid, urine, ethanol, acetaldehyde, acetic acid, glycolic acid, ethylene glycol, glyoxal, oxalic acid, methoxymethane, methyl formate, 1-Propanol, Isopropanol, Propylene glycol, 1,3-propanediol, Glycerin, Propionaldehyde, Malondialdehyde, malonic acid, pyruvic acid, Mesoxalic acid, Tartronic acid, Methoxyethane, 2-Methoxyethanol, Ethyl formate, methyl acetate, Butanol, Isobutanol, tert-Butanol, 2-Butanol, 1,2-Butanediol, 1,3-Butanediol, 1,4-Butane di ol, 2,3-Butanedi ol, 2-Methyl-1,2-propanediol, 2-Methyl-1,3-propanediol, 2-Methyl-2,4-pentanediol, 1,2,3-Butanetriol, 1,2,4-Butanetriol, 1,3,4-Butanetriol, Erythritol, Butyraldehyde, Succinaldehyde, Isobutyraldehyde, Methyl Ethyl Ketone, Diacetyl, α-Ketobutyric acid, butyric acid, Isobutyric acid, Acetoacetic acid, 4-oxobutanoate, 3-Hy droxy3-formyl prop anoi c acid, 3-oxobutanoi c acid, Succinic Acid, Maleic acid, Fumaric acid, Methoxypropane, Diethyl ether, Methyl propionate, Dimethyl malonate, propyl formate, isopropyl formate, butyl formate, methyl butyrate, ethyl acetate, dimethyl oxalate, Acetonedicarboxylic acid, Glucose, Fructose, Sucrose, Lactose, Maltose, Galactose, Ribose, Xylose, Mannose, sobutyric acid, Valeric acid, Isovaleric acid, Caproic acid, Caprylic acid, Capric acid, Lauric acid, Lactic acid, Citric acid, Pyruvate, Succinate, Oxaloacetate, α-Ketoglutaric acid, Fumarate, Malate, Glutamate, Dimethyl sulfoxide, Sorbitol, Gluconic acid, Methanesulfonic acid, Polyethylene glycol, and combinations thereof.

The invention claimed is:

1. A method for producing an antimethanogenic halide compound, said method comprising the steps of:
   a) providing a haloperoxidase enzyme;
   b) providing a reaction solution, said reaction solution comprising:
      i) formate;
      ii) hydrogen peroxide; and
      iii) bromide;
   c) contacting the haloperoxidase enzyme with the reaction solution for a time period sufficient to produce an antimethanogenic halide compound, and
   d) separating the antimethanogenic halide compound from the reaction solution.

2. The method of claim 1, wherein the haloperoxidase is a vanadium-dependent haloperoxidase.

3. The method of claim 1, wherein the haloperoxidase is a recombinant peroxidase.

4. The method of claim 1, wherein the bromide is selected from the group consisting of sodium bromide, potassium bromide calcium bromide, and combinations thereof.

5. The method of claim 1, wherein the antimethanogenic halide compound is selected from the group consisting of methyl bromide, bromodichloromethane, bromoform, dibromomethane, and combinations thereof.

6. The method of claim 1, wherein the formate is sodium formate or potassium formate.

7. The method of claim 1, wherein the antimethanogenic halide compound is bromoform.

8. The method of claim 1, wherein the reaction solution comprises at least 2.4 mM formate.

9. The method of claim 1, wherein the reaction solution comprises between 100 mM and 400 mM hydrogen peroxide.

10. The method of claim 1, wherein the reaction solution has a pH of at least 5.0.

11. The method of claim 1, wherein the time period is at least 90 minutes.

12. The method of claim 1, wherein the separating the antimethanogenic halide compound from the reaction solution comprises adding a layer of oil on top of the reaction solution.

13. The method of claim 1, wherein the haloperoxidase enzyme is comprised within an algal biomass.

14. A method for producing an antimethanogenic halide compound, said method comprising the steps of:
   a) providing a bromoperoxidase enzyme;
   b) providing a reaction solution, said reaction solution comprising:
      i) formate;
      ii) hydrogen peroxide; and
      iii) bromide;
   c) contacting the bromoperoxidase enzyme with the reaction solution for a time period sufficient to synthesize an antimethanogenic halide compound; and
   d) separating the antimethanogenic halide compound from the reaction solution, wherein the antimethanogenic halide compound is selected from the group consisting of bromoform, methyl bromide, dibromomethane, and combinations thereof.

15. The method of claim 1, wherein the separating the antimethanogenic halide compound from the reaction solution comprises removing at least a portion of the haloperoxidase enzyme from the reaction solution.

16. The method of claim 14, wherein the separating the antimethanogenic halide compound from the reaction solution comprises removing at least a portion of the bromoperoxidase enzyme from the reaction solution.

* * * * *

SEQUENCE LISTING

```
Sequence total quantity: 53
SEQ ID NO: 1           moltype = AA  length = 590
FEATURE                Location/Qualifiers
source                 1..590
                       mol_type = protein
                       organism = Asparagopsis taxiformis
SEQUENCE: 1
MTDTQNPNRA EVAFKVRVSA AELARARGSP THLSNNSESR FRNPDGTRSL LANFTKGLPH    60
TKETALVVSA IDYDSFVRAI DSGDPRDFAD LPLGPQGVEP RFTSGIASDP EVGTRAWESG   120
GAGLVFDLEG PDAQAVTMPP APELDSDELV TEVTECYWMS LLRDVPFPTF DSDPHIQSAA   180
```

```
ESINNTQWIQ FKNNPPAHLT AAERSRLRGP ITTANVFRGI TPGDEVGPYL SQFLLVGTTG   240
IANGNEVGDG FIQYGGMRMD QRVRVAKSHI DYMTTFGAYL DVQNAANVSG RELYNEEEPR   300
FRFIHTPRDL ATYVHFDALY QAYLNACIIL LDIGAPFDSG IPFQLDNDID KQQGFATFGG   360
PHILSLVTEV ATRALKAVRF QKFNVHRRLR PEAIGARVDR YCATKAPEFA GAAKLSEALD   420
KKLLQKVHDH NKKQNLLSDR GNPRANDFNP DGDVSKGNLL MPMAFPEGSP MHPAYGAGHA   480
TVAGACVTVL KAFFDGGYRL PFCYITDENG TGLKAVEIDE PLTVDGELNK ICSNISIGRN   540
WAGVHYFTDY IESIRIGEEI AIGILQEQKL TFSENFSMTL NKFDGSTIRI              590

SEQ ID NO: 2            moltype = AA  length = 586
FEATURE                 Location/Qualifiers
source                  1..586
                        mol_type = protein
                        organism = Asparagopsis taxiformis
SEQUENCE: 2
MAEERRQNAL DIRIQAARLA KKRDHPTHEA NGDEDRYPET LIGSFTKGLP HEKETGLLSN    60
PADFADFVRA INTGAIKDIR RLKLGIDEDP RFISGIASKG DKHPFADTRA WESMAAGLTY   120
DLEGPDAQAV TMPPAPKLDS DELVTEITES YWMALIRDVP FTEFERDGNT AAAAASISRT   180
RWVQFNEQPS QRPSTLTDEE IARLRGPYTK KNVFRGVTIG ENVGPYLSQF LLVGTKGIGD   240
VQQISDGYIQ YGSMRMDQRV RVAAPKRDYM TTWASWLDVQ NAGDLRGREI YDDDTPFRFI   300
TTPRDLATWV HFDALYQAYL NACIILLDIK APFDPHIPFQ ADDDVDKQQG FATFGGPHIL   360
SLCTEVATRA LKAVRFQKYN VHRRLRPEAI GGLVERFKKT NGDAKFAPVK KLVNDLDGDM   420
LRRIEQHNCE QNKLSDDGHA RRDDYSPEGE SNQTYLLPMA FPEGSPMHPS YGAGHATVAG   480
ACVTVLKAFF DHEYELDFCY VPTTDGKRLE KVNINEKLTV EGELNKLCAN ICIGRNWAGV   540
HYYSDYFESI KVGEEIAIGI LQEQKLTYGE DFFMTLSKFD GEKIRI                  586

SEQ ID NO: 3            moltype = AA  length = 598
FEATURE                 Location/Qualifiers
source                  1..598
                        mol_type = protein
                        organism = Corallina pilulifera
SEQUENCE: 3
MGIPADNLQS RAKASFDTRV AAAELALNRG VVPSFANGEE LLYRNPDPDN TDPSFIASFT    60
KGLPHDDNGA IIDPDDFLAF VRAINSGDEK EIADLTLGPA RDPETGLPIW RSDLANSLEL   120
EVRGWENSSA GLTFDLEGPD AQSIAMPPAP VLTSPELVAE IAELYLMALG REIEFSEFDS   180
PKNAEYIQFA IDQLNGLEWF NTPAKLGDPP AEIRRRRGEV TVGNLFRGIL PGSEVGPYLS   240
QYIIVGSKQI GSATVGNKTL VSPNAADEFD GEIAYGSITI SQRVRIATPG RDFMTDLKVF   300
LDVQDAADFR GFESYEPGAR LIRTIRDLAT WVHFDALYEA YLNACLILLA NGVPFDPNLP   360
FQQEDKLDNQ DVFVNFGSAH VLSLVTEVAT RALKAVRYQK FNIHRRLRPE ATGGLISVNK   420
IAPQKGESIF PEVDLAVEEL GDILEKAEIS NRKQNIADGD PDDPSFLLP MAFAEGSPFH   480
PSYGSGHAVV AGACVTILKA FFDSGIEIDQ VFEVDKDEDK LVKSSFKGTL TVAGELNKLA   540
DNIAIGRNMA GVHYFSDQFE SLLLGEQVAI GILEEQSLTY GENFFFNLPK FDGTTIQI     598

SEQ ID NO: 4            moltype = AA  length = 597
FEATURE                 Location/Qualifiers
source                  1..597
                        mol_type = protein
                        organism = Corallina pilulifera
SEQUENCE: 4
MGIPADNLQS RAKASFDTRV AAAELALARG VVPSFANGEE LLYRNCETGD PSFIASFTKG    60
LPHDDNGAII DPDDFLAFVR AINSGDEKEI ADLTLGPARD PETGLPIWRS DLANSLELEV   120
RGWENSSAGL TFDLEGPDAQ SVAMPPAPVL MSPELIAEMA ELYLMALGRD IEFSEFESPK   180
NAAFIRSAIE RLNGLEWFNT PAKLGDPPAE IRRRRGEVTV GNLFRGILPG SEVGPYLSQY   240
IIVGSKQIGS ATVGNKTFVS PNAADEFDGE IAYGSITISQ RVRIATPGRD FMTDLKVFLD   300
VQDGADFRGF ESYEPGARLI RTIRDLATWV HFDALYEAYL NACLILLANG VPFDPNLPFQ   360
QEDKLDNHDV FVNFGSAHVL SLVTEVATRA LKAVRYQKIH IHRRLRPEAT GGLISVNKKS   420
FLAGSDIIFP EVSELVEELS SILDDVAESN EKQNRADGIV SPDKSFLLPM AFAEGSPFHP   480
SYGSGHAVVA GACVTILKAF FDANFQIDKV FEVDTDEDKL VKSSFKGTLT VAGELNKLAD   540
NVAIGRNMAG VHYFSDQFES LLLGEQIAIG ILEEQSLTYG ENFFFNLPKF DGTTIQI      597

SEQ ID NO: 5            moltype = AA  length = 423
FEATURE                 Location/Qualifiers
source                  1..423
                        mol_type = protein
                        organism = Amycolatopsis mediterranei
REGION                  1..423
                        note = strain U32
SEQUENCE: 5
MTTSMSRRHL LVTGGAAAAV LATTGLPSPA AAPAHASGP AVVLAWNREL LAIVRTPGLQ     60
PATVHPTRSF ALLHAAIHDA VVATTGTGRP YLFTVDVPGH AAPEAAAAQA AHDVLAALYP   120
ARAAELADLL AGQLARVTPP AARTDGVRAG QLVARLLLGL RTGDGSAAIP PVLPPGTAPG   180
QYRPTPPAFA PAAFTHWAAV TPFVLDRADR FRAAPYPSLS GARYAKALQE VAAAGRDTST   240
TRTADETVQA RFWAAPIWNY WNEIAQSVVT GSRSNLLVAA RVFARLNLAF ADAVIAFYEA   300
KYHYRIWRPI TAVRLAGEDG NPATDGVPDW SSLATTPADP AYPGAHSVVS QAGALVLRRE   360
YGPRWPVEVA SEALPGVQRR FASFQEAADE AGLSRITAGV HTRLDHEAGR RLGLDVAAFV   420
LRS                                                                 423

SEQ ID NO: 6            moltype = AA  length = 531
FEATURE                 Location/Qualifiers
source                  1..531
```

```
                        mol_type = protein
                        organism = Streptomyces sp.
REGION                  1..531
                        note = Strain CNH189
SEQUENCE: 6
MKTSGHTSAS DLSLGRRSLL LGGSSAALML ALPHPANAGT SEEPPTFDFD LDTDNYIKWV    60
KPATDEQASQ SPLWESVGSM DVTVILWMSR VGNLAVFDAV APYHETAVGV YSRIPRRPSS   120
ESATNRNMNI AILYTQLHTF ERLLPLGLRG PAGSLRAMMV GLGLDPDNKS EDLTTPVGIG   180
NVAFKSVWNA LKNDGMNVLG YEGGRKYNPL PWADYTGYEP VNTPFRLNNP SRWQPQLHAH   240
NGRRPGGGPG DLGIYVSQHF VTPQIALTKP HIFTDPAQFP LAAPKHSDHT RPRDYKRSVD   300
EILEASASLN DERKALAEVM DNKLWGIGYT STVIGRKYDE NNEMGVFGWA AWSLQHFLAT   360
FDALIAVWRN KRKYDTVRPV SAVRHVYGHS KVTAWGGAGM GTVNDIRATE WMPYLPTGDH   420
PEYPSGSTSL CAAGAQTARR YFNSEELDWT LEFNAGTSAV EPETTPAKNL QLHFHTWAEF   480
NKACAESRVW GGVHFRKTVQ QSLIYGEQFG DLAHEFVNRH VKGNIKTDTR N            531

SEQ ID NO: 7            moltype = AA  length = 517
FEATURE                 Location/Qualifiers
source                  1..517
                        mol_type = protein
                        organism = Streptomyces sp.
REGION                  1..517
                        note = strain CNH189
SEQUENCE: 7
MTTSERSSVS DFSPRRRSLL IGSASAAALA TLGSTGTAAA AGAADEPPTV DFDFDNGNFI    60
RDLIITRAGG VFPEEGVIGP MDASVYIWIT SLFQLSWFDA LAPYHPTAVG IHSRIARRPA   120
GEAATNRNKN IAGLYAALRV LEGVFEERVP VMRAGFTAAG LDPDDRSEDP TTPIGIGNIA   180
GKAVVRARAN DGMNHLGNVG RKYHGKPYED YTGYQPVNSP YKLVNPSKWQ PALHPHQRRV   240
GGGPGDKGIW VIQAFVTPQL ALVKPYTYRN PGQFTVPVPD HSTHTNVRKY KQSVDQILEA   300
SATLTDEKKL MAEWFDNKLA GIALAPSAAA LSHDLDLDGW CHLYAVTALA RLDDLIAAWH   360
WKTKFNSVRP FTAVHHVYGR KKISAWGGVG KGTVHDMPAN EWSSYLPVGD HPEYISGSTT   420
LCSAEAQAAR RFLGDDVLDW TYSFPAGSGL TEPGLVPAKD TELHWDTWTR FTRDCADSRV   480
WGGVHFQTTV DRSIEWGAQF GDRAHQFLQR HIKGEVS                            517

SEQ ID NO: 8            moltype = AA  length = 460
FEATURE                 Location/Qualifiers
source                  1..460
                        mol_type = protein
                        organism = Gramella forsetii
REGION                  1..460
                        note = strain KT0803
SEQUENCE: 8
MEKPNFIIST FEMRRIILFI TLIITTISCK KEAQKIVVTE DDFHAANENL SKTMVHDIFS    60
PPVASRVYAY SNIAAYEVIA QFNPEFNSLT GQLTELHPTP KPQSEKVNPE IAALTAFYEI   120
GKSLVFSEER MTTKRDSLFN SWMEMDEETF IVSKAYGMKV AKHINNWMKN DNYAETRTMP   180
KFTVRTDDES RWQPTPPSYM DGIEPHWMKI RPFVIDSSNQ FKPAPPPEFS MEEGSRFHTE   240
LMEVYNIREE IAEDEENSEK MAIAKFWDCN PYVSILRGHL MFATKKITPG GHWIGITKIA   300
CQKSGAGFDK SVYAYAKTSV AIADAFISCW DEKYRSNLVR PETLINKYID ESWSSVLQTP   360
PFPEYTSGHS VISGAAAIAL TDIFGDNFSF EDDTEVDYGL PVRNFTSFKA ASIEAANSRL   420
YGGIHYRVAI EVGLEQGQEL GDFIVNKLKM RNSKADLASK                         460

SEQ ID NO: 9            moltype = AA  length = 484
FEATURE                 Location/Qualifiers
source                  1..484
                        mol_type = protein
                        organism = Zobellia galactanivorans
SEQUENCE: 9
MKRILTLALT LGLLYSGVIF AQKNQEEPRG TENVAYQWGK MALDATASDT ERFKPRPTIT    60
SRYLGLIFVS IFDAWSRYDE SAIPVYLNDV DRRPANERNL KNKEIAISYA AFGAMKEYYF   120
SDTEMPRKLM ADLGLDPDNT SMDPTTPEGV GNLAAKATIE ARKNDGSNQY GEAKGANGEP   180
YSDYTNYSPV NTADENTDIN RWQPKYFSDG KGGQYAPGCL TPYWQKVKPI ALTSADQFRP   240
GPPPLVGSKQ LKKEVKEVVD LQAHLSDEEK ALVEFMRDGP QSVQQAGHWL KFAQDVSRRD   300
NHTLDEDVKM YFLTEITAMD AFIASWDSKM FYDYARPYAL VHEYYKDKTI KAWAGPGKGV   360
IKMKGQEWRP YSPDIFLCPP FPSYTSGHST ISGGCAEVLR LFTGSEHFGE SVKLVAGSMT   420
ELDSAHYGKT VTIHFPTFTE TANMAGMSRV MGGYHIQADN IAGLQLGRDV ASQAWKFYNK   480
HLGQ                                                                484

SEQ ID NO: 10           moltype = AA  length = 441
FEATURE                 Location/Qualifiers
source                  1..441
                        mol_type = protein
                        organism = Zobellia galactanivorans
SEQUENCE: 10
MKRLSRFIIV CTVLMVSCGT NHDKERLDTY FEGGLSRYNR ELTNVIVSDI FTPPVASRIY    60
AYSNIAAYEG IRFMDSTKLS LSSRLNGLKE LSTPDPSKNY YYPLVSIVAF TQVGKSLVFD   120
LDKVEAIKNK MLGEVKEIGM DQEVYRNSID LGETLASEIL AWAAKDGYLR RTALPRYSVS   180
DDPGRWRPTP PDYMEAIEPH WNTLRPFVLD SAAQFDPGLP TPPDSAEDSP FYKEAMEVYE   240
TVENLDDDKL EVAKFWDCNP NISHTKGHVM YFQQQISPGG HWMHIAAQIL EEQKVDGVKA   300
AETMSMLGVA LADAFISCWD QKYKSSLTRP ETYINNYIDQ DWEPILQTPA FPEHTSGHSV   360
ASSAAATVLT GVFGDDYAFV DATEVPYGLP PRSFQSFWQA AEEEAAISRLY GGIHYRPAIE   420
```

```
LGVKQGRAVG RLVLERLRKE H                                              441

SEQ ID NO: 11               moltype = AA  length = 450
FEATURE                     Location/Qualifiers
source                      1..450
                            mol_type = protein
                            organism = Zobellia galactanivorans
SEQUENCE: 11
MKKILIALIS FAFAVSCKAP QKEEPINITP EELDASIDRV TEIMIHDIFS PPVASRIFAY      60
PNVAAYEIVA ATNDNYNSLA GQLNGLTAIP EPDTTKTINY ELAAVHAME LSKRLIFSED      120
RMESLRDSLY MVWEGKNPVL FSDSKAYGLQ VADHIGEWMN KDNYAQTRTM PKFTVDADDP     180
GRWQPTPPAY MDGIEPHWNK IRPFVLDSAA QFKPVPPPAY SLEEDSAFYK ELKEVYDVRN     240
KITEEGDSSE EIQIARFWDC NPYVSVTRGH LMFATKKITP GAHWMGIAKI AARKTNSDFA     300
KTLFAYTKAS VAMADAFISC WDEKYRSNLI RPETVINQHI DDSWKPVLQT PPFPEYTSGH     360
SVVSGAASVV LTEVFGDNFS FDDDTEVPYG LPIRSFKSFK QAADEAAISR MYGGIHYRAA     420
IEVGVKQGRD LGTFVVNKLH MLSDKKVAQN                                     450

SEQ ID NO: 12               moltype = AA  length = 446
FEATURE                     Location/Qualifiers
source                      1..446
                            mol_type = protein
                            organism = Zunongwangia profunda
REGION                      1..446
                            note = strain SM-A87
SEQUENCE: 12
MKKVLVLLLT ISLFTGCADE KSASKESVAI SANNYHEALD KITNIMVHDI FSPPVASRIY      60
SYSNLAAYEI VAQHNPEMNS LTKTINADIE IPVLDTTKAI DYRMAALIAQ LEIGKTLIFS     120
EVEISDYSDS LFVNWKKNNE EIFINSEAYG MLVANVFKQW IDKDNYKQTR TMPKFSVYTE     180
DVSRWQPTPP AYMDGIEPHW MKIRPFTLDS ASQFKPKSHP EFSMEEGSQF YKELMEVYDV     240
RNQMEETGNK SEEMAIAKFW DCNPYVSTQR GHLMFATKKI TPGGHWIGIT KVACNKANLD     300
FDKTVYAYTT TSMAIADAFI SCWDEKYRSN LVRPETLINK FIDDDWKPVL QTPPFPEYTS     360
GHSVVSGASA EVLSKLFGDQ FQFLDDTEVP YGLPKREYAS FRNAAKEAAL SRLYGGIHYR     420
AAIENGLDQG ISLGKHVINT LEVKTL                                         446

SEQ ID NO: 13               moltype = AA  length = 626
FEATURE                     Location/Qualifiers
source                      1..626
                            mol_type = protein
                            organism = Acaryochloris marina
REGION                      1..626
                            note = strain MBIC11017
SEQUENCE: 13
MTDRRQDSYA VRVEAAELAR SRNHPDHQAN GDEERYAGAK YFMSFTKGLP HNEETGLLGD      60
PKDFVEFRRA IDDGFIDPFS SDLIRHGALY KVEGGEVKRV DREVDGDPPN NFRQWEAPTA     120
GVVFDLEGPD AQAVTMPPAP PLLDGNGNPN PELVLEMAEV YELAILRDQP FNDFENGRSN     180
AAITQSIDRL NALSYISNQT GRPRKVNTSG QLDAQTVFRG SSPGVEAGPY LSQFLLIGNT     240
DLNRDADGIG GGKVEDGLIT YGALQINQRV PIAEPGKVPN RSMSEYVEVQ RGIRPPRETY     300
GSTNGGSVAQ PNRPPRRFIS TPRDLSTYVH YDALYEAYLN ACIILLEMGT PFDPGFDHLS     360
GVGAAASSFE SRRNAGGFAL YGGPHILTLV TEVATRALKA VRFQKFNNHI RLRPEALAAR     420
IELVNSFDGL SQADKDTVPE VLKKYIGLFS NALKPTLNAL GGNYLLPMAF PEGSPMHPAY     480
GAGHATVAGA CVTILKAFFD TSAVLAKSGQ SIAFKRLENG DKPIAFRAPD LPGSGPGEGV     540
PKDDLKPFKP NHFLTLEGEL NKLAANISIG RDMAGVHYFT DYYDSLRMGE EIAIGILEEQ     600
ALTYSTDPFV LSVPTFDGDV RRIGRR                                         626

SEQ ID NO: 14               moltype = AA  length = 622
FEATURE                     Location/Qualifiers
source                      1..622
                            mol_type = protein
                            organism = Synechococcus sp.
REGION                      1..622
                            note = strain CC9311
SEQUENCE: 14
MTDQRKLTAQ RVREDANALA AGRIHPRHQA NGDEQRYESA NYAMSFTKGL DHNTTTGLIE      60
QSGDFEAFRS AIDNGFAEDF TRHVAVPRAE PRRKWEAPTA GTVYELQGPD PQAVTIPPAP     120
ALCSDELTFE MAEVYELALL RDLPFNAFVA GGGSAALADS TARLNSLAYA QDGFNRRPRT     180
TNSSNQLDAQ TVFRGSSPGV DQGPYLSQFM LIGNASPSEG ITPEQGFINF GAQRIDQRVL     240
EARQQDDYMM KWDDWHRVQQ GYEVRADRFD PCKSSGPGQA FTGQRRFIHT PRDLATYVHV     300
DALYQAYLNA CLLLLGNGTA FDPGFDLLSG GGEGLLHDPA GGQKVPLNAG GFALWGGPHV     360
LSLVTEVATR GLKAVRYQKF NNHLRLRPEA LAARIEKAQE IESRFPTICG CFSEMASDLQ     420
QVVDLIRNHN QSLAGEATAL LPMAFAEGSP MHPAYGAGHA TVAGACVTIL KAFFNTSALF     480
VKINDVAGFH SKQHILARLK CGDSVEAGAY QETDCGKRLE FERCGSFHLI EGKYATFKPD     540
GKTNQSCCPL TLEGELNKLA ANISIGRNMA GVHYFSDYYD SLRMGEEIAI GILEEQALCY     600
KTDPFVLSVP TFDGDVRRIG QR                                             622

SEQ ID NO: 15               moltype = AA  length = 539
FEATURE                     Location/Qualifiers
source                      1..539
                            mol_type = protein
                            organism = Clostridium botulinum
```

-continued

```
REGION                          1..539
                                note = type A str. ATCC 3502
SEQUENCE: 15
MEEKQDKNIE KYESEDKVCI TKPSCPKYNT IINQCEIGPL TPEQRRSEAF EKRSQSASFQ    60
KDLILQGQRC NDDEILYVNK IGNNTKALPH NVLGEVNLEA YNILISALTT GNPEKFELIP   120
LGGTRKFSDP QAAYAYEMVG PDSHHLTIAP APSFSSAIEA SEMAEDYWMA LTRDVPFVDY   180
DTSPETKTAA EDLSKFSAYD GPKCKGKVTT ETLFRSNVPD TLEGPYVSQF LLKDIPFGAK   240
TITQKYTVPV EKINYMTSYN EWLNIQNGQA PSSILKLDPV PRYISNGRDL GEYVHKDSSI   300
QATLMACSIL LGFGQEALSL SNPYLFSKTQ EGFATFGSPH VLDFATRASR MSLEAAWFQK   360
FLVHRRLRPE EFGGCVQNLK TGDAKYPINP ELLDSKVLEI VFKKYGTYLL PMAYTEGCPT   420
HPAYPAGHAT HIGAGVTILK AFFNEDYIIP NPVVASADGL DLQPYLEGDL KVGGELNKLA   480
TNIALGRDFA GVHWRSDCLE GMKLGEAVAI GLLQDYRNTY NEELRGFSFT KFDGTKVII   539

SEQ ID NO: 16                   moltype = AA  length = 538
FEATURE                         Location/Qualifiers
source                          1..538
                                mol_type = protein
                                organism = Clostridium botulinum
REGION                          1..538
                                note = type F str. Langeland
SEQUENCE: 16
MEEKQDKNIE KYEGEDKGCI TKPVCPKNTI INQCEIGPLI PKQRRIEAFE KRNQSALFQK    60
NLILQGQRCN DNEISYVNKI GNNTKALPHN LLGEVNLEAY NILISALTTG NPEKFELIPL   120
GGTKKFSDPQ AAYAYEMVGP DSHHLTIAPA PSFSSAIEAS EMVEDYWMAL TRDVPFVDYD   180
TNLKTKAAAE DLSKFSAYDG PKCKGKVTTE TLFRSNIPDT LEGPYVSQFL LKDIPFGAKT   240
ITQKYTVPVE KIDYMTSYNE WLNIQNGQAP SSILKLDPVP RYISNGRDLG EYVHKDSSIQ   300
ATLTACSILL GFGQEALSLS NPYLFSKTQE GFATFGSPHV LDFATRASRM ALEAAWFQKF   360
LVHRRLRPEE FGGCVQNLKT GAAKYPINLE LLDSKVLEIV FKKYGTYLLP MAYTEGCPTH   420
PAYPAGHATH IGAGVTILKA FFNEDYIIPN PVVASDDGLE LQPYLEDDLK VGGELNKLAA   480
NIALGRDFAG VHWRSDCLEG IKLGEAVAIG LLQDYRNTYN EEFHGFSFTK FDGTKVII   538

SEQ ID NO: 17                   moltype = AA  length = 538
FEATURE                         Location/Qualifiers
source                          1..538
                                mol_type = protein
                                organism = Dyadobacter fermentans
REGION                          1..538
                                note = strain DSM 18053
SEQUENCE: 17
MEEKQDKNIE KYEGEDKGCI TKPVCPKNTI INQCEIGPLI PKQRRIEAFE KRNQSALFQK    60
NLILQGQRCN DNEISYVNKI GNNTKALPHN LLGEVNLEAY NILISALTTG NPEKFELIPL   120
GGTKKFSDPQ AAYAYEMVGP DSHHLTIAPA PSFSSAIEAS EMVEDYWMAL TRDVPFVDYD   180
TNLKTKAAAE DLSKFSAYDG PKCKGKVTTE TLFRSNIPDT LEGPYVSQFL LKDIPFGAKT   240
ITQKYTVPVE KIDYMTSYNE WLNIQNGQAP SSILKLDPVP RYISNGRDLG EYVHKDSSIQ   300
ATLTACSILL GFGQEALSLS NPYLFSKTQE GFATFGSPHV LDFATRASRM ALEAAWFQKF   360
LVHRRLRPEE FGGCVQNLKT GAAKYPINLE LLDSKVLEIV FKKYGTYLLP MAYTEGCPTH   420
PAYPAGHATH IGAGVTILKA FFNEDYIIPN PVVASDDGLE LQPYLEDDLK VGGELNKLAA   480
NIALGRDFAG VHWRSDCLEG IKLGEAVAIG LLQDYRNTYN EEFHGFSFTK FDGTKVII   538

SEQ ID NO: 18                   moltype = AA  length = 598
FEATURE                         Location/Qualifiers
source                          1..598
                                mol_type = protein
                                organism = Rhodopseudomonas palustris
REGION                          1..598
                                note = strain HaA2
SEQUENCE: 18
MTIRRVFVAT FILSLTPVVS TAQPVLQTQS LDDFRRILSP GLISREVTSE KVSQLNAEAA    60
KSCFAPDAFQ RAIPALPIRY KRPLPCAPQN AFDRFVMWNQ IALDTTSMDH APPPLGTPDN   120
PALHNYGPHR SSRVMAIVHI AMFDAINLAM RFDSKSPDKP RYVFATYLQG IPNPKEDASV   180
DMAITYSAGE TLKALYPQQV DVIENLIAID EGAVLSGKDR NAPMYRAGRE LGITVAKAIL   240
RARRRNDGSAH EEPQVGDPGF PLAEKSGQWR PDPVSNIAAA LGGKWKDVQP FVIKNVPTFR   300
PPPPPSTDSA EYARDFEEVR KLGGENTERS RSERSADQTL IGTFWAYDGT AFLCAPPRLY   360
NQVIRQIVQQ QIKDGDTKDE DPKLLNYARL FALANIAMAD AAIAAWDAKY HYRYWRPVVG   420
IRAAATDGND ATHADVYWKA LGAPASNSVR GPNFTPPFPA YPSGHATFGG ALFEVLRAFY   480
PDDTSFSFIS DEYNGQNKPA GSDVPRPEVT RRFVNFRAAE DENARSRVYL GVHWQFDADA   540
GIAQGNQVGS FVVGSTLRCL DDDGRALDCK PGSGFDVKRK FLISTEKRVL STPFTPSQ   598

SEQ ID NO: 19                   moltype = AA  length = 466
FEATURE                         Location/Qualifiers
source                          1..466
                                mol_type = protein
                                organism = Sorangium cellulosum
REGION                          1..466
                                note = So ce56
SEQUENCE: 19
MNRSAARWVS VSFAALATAL LAARAFAHVP EAQGDPPDRD AVLDWNAVAL DAVAEDTAGA    60
RARDQGGPTR VSRALAIVHA AIFDAVNSIV PGYKPYSILL DMPDASIDAA VATAAHRTLT   120
ALFPSQRALL DGRLREYLAE IPESDAKEDG RALGGAVADE ILGEREDDMS DAPMPYTPDI   180
```

```
APGRHRVDPL YPEQGYLTPR WGKVRPFAIE SGAEFRSRPP PPLWSLEYAL SFYEVFLLGG  240
DGQRTPTART PEQTVIGIFW SYDSAPRLGE PPRLYNQIAR VLAVKECNSE IENARYFALV  300
NVALADAAIA TWETKYHYEF WRPIVAIRRA DRDGNSLTVA DRRWTPLGSP GSNQGPPRMT  360
PAFPAYTSGH ASFGAAMFQV LTRYYGTDCI PFCFMSDEYN GVTTDERGNV RPEITRCYSS  420
FEEASWENAV SRVYLGVHWR FDGVQGIRQG KRVGDAVFDR ILRPLP                 466

SEQ ID NO: 20           moltype = AA   length = 609
FEATURE                 Location/Qualifiers
source                  1..609
                        mol_type = protein
                        organism = Curvularia inaequalis
SEQUENCE: 20
MGSVTPIPLP KIDEPEEYNT NYILFWNHVG LELNRVTHTV GGPLTGPPLS ARALGMLHLA   60
IHDAYFSICP PTDFTTFLSP DTENAAYRLP SPNGANDARQ AVAGAALKML SSLYMKPVEQ  120
PNPNPGANIS DNAYAQLGLV LDRSVLEAPG GVDRESASFM FGEDVADVFF ALLNDPRGAS  180
QEGYHPTPGR YKFDDEPTHP VVLIPVDPNN PNGPKMPFRQ YHAPFYGKTT KRFATQSEHF  240
LADPPGLRSN ADETAEYDDA VRVAIAMGGA QALNSTKRSP WQTAQGLYWA YDGSNLIGTP  300
PRFYNQIVRR IAVTYKKEED LANSEVNNAD FARLFALVDV ACTDAGIFSW KEKWEFEFWR  360
PLSGVRDDGR PDHGDPFWLT LGAPATNTND IPFKPPFPAY PSGHATFGGA VFQMVRRYYN  420
GRVGTWKDDE PDNIAIDMMI SEELNGVNRD LRQPYDPTAP IEDQPGIVRT RIVRHFDSAW  480
ELMFENAISR IFLGVHWRFD AAAARDILIP TTTKDVYAVD NNGATVFQNV EDIRYTTRGT  540
REDPEGLFPI GGVPLGIEIA DEIFNNGLKP TPPEIQPMPQ ETPVQKPVGQ QPVKGMWEEE  600
QAPVVKEAP                                                         609

SEQ ID NO: 21           moltype = AA   length = 613
FEATURE                 Location/Qualifiers
source                  1..613
                        mol_type = protein
                        organism = Embellisia didymospora
SEQUENCE: 21
MTIDFTPVEL PVVEEDAEYN WNYILFWNNV GLELNRVTHT FGALKAGPPL SPRALGMLQL   60
AVHDAYFAIH PSAGFTTFLT PGAEDGAYRL PDPSYAKDAR QAVAGAAIAM LSKLYMKPKV  120
VPRSPISHNA YAQLQHVLDI SVTKAPAACD PASSSFIFGK AVATAVFDLL FHKEGADQSG  180
YSPKPGPFKF NDEPTHPVEL IPVDANIPDG DKMPRRQYHA PYYGETAKRF GTQTEHMLAD  240
PPGIRCAGEV AEYDDAIREV YAMGGAPGLN TTKRTPHQTV QGMFWAYDGP KLIGTPPRLY  300
NQIVRKIAVT YKKDNDLVNS EVNNADFARL LALVNVAMTD AGIFAWKEKW EFEFWRPLSG  360
VRDDVLRDPE GKASTAAIHS GLASAPQLQN SDEAPFKPPF PAYPSGHATF GAAAFQMVRK  420
YYNGRLGKWA TTSRDTIAVE MFVSEELNGV SRDLSNPHDP KRPITDQPGI VPTRMPRRFS  480
SCWEMMFENA VSRIFLGVHW RFDAAAGQDI LIPTTKKDVY AVDDKGAALF KNVEDIRYKT  540
KGTRKGHKGL LPIGGVPLGI EIANEIYNNK LSPTPPGEQP MPQPPHQGP PRKKGELAEA  600
KDEEQAPMMD VAP                                                    613

SEQ ID NO: 22           moltype = AA   length = 596
FEATURE                 Location/Qualifiers
source                  1..596
                        mol_type = protein
                        organism = Gaeumannomyces graminis
REGION                  1..596
                        note = var. tritici R3-111a-1
SEQUENCE: 22
MIPILPPTGE PAEYNDNYIL YWNNLALDLN RLSHSLPTNP QGGPAASSRV LGILHLAIHD   60
AYFAINPPAD QSFTCYLAEL PPHGGLMDAR TAVAGAAITA LEMLYTTPSA GIATATTFAM  120
RQTIGQAIDG FSNLDARLPE YQFGAAVARA LIALLIPPND PGVGQGAYRT KEGPYKFRVE  180
PNHPVRLVPV DPNNPNGPKQ AIAESYGPFY GGVRRFAVQT DDHVIADPPA GAAREDPVED  240
IDSLLDTIRS GVVPEDNRSR RSPSQNVTAH FWAYDGTNLL GTPPRLYNQI LRKLAFERRP  300
DTSDLAAEAN NADFARLLLAL CNAAMGDAGI FSWREKYTFE IWRPLTGVRE HPSGLGDPFF  360
QTVGSPETNN NGISFKPPFP AYPSGHATFG GATFQMARLY YKRRDGLDFA DDAPDDIGLE  420
FVSDELNGVN RDLREDYDPA RPITQQVGTV RTRVPVCFSS LWEIMHENAL SRVFLGVHWR  480
FDAFAARDVL VANPNPEPGA SPYALNPDGS TRYKPVAEVR YETRASRFDR DGLFPIGGVP  540
LGIGIANEIF SANLQPTPEN AQPGQTTQGL AAGSGKGQGA QRKLNGTNGT NGGVAA      596

SEQ ID NO: 23           moltype = AA   length = 621
FEATURE                 Location/Qualifiers
source                  1..621
                        mol_type = protein
                        organism = Pyrenophora tritici-repentis
REGION                  1..621
                        note = Pt-1C-BFP
SEQUENCE: 23
MANFTPVRLP KVEEDEVYNK NYILYWNNVG LDLNRVTHTL GGPQTGPPIS ARALGMLQLA   60
IHDAYFTIKP SADFTTFLTP NAEIDAYRLP DPTHSDDARQ AVAGAAVTML SMLYMRPAEM  120
PRPSPISNDT YAQLEYIIES SMTNAPGGCN TVSYSFNFGK AVATKFFDLL FHEEGANQRG  180
YTPTFAPFKF NDEPTHPVDL VPEDANEPGG NIVPRRQYHA PFYGTRAKRF ATQTDHIIAD  240
PPGIRSGAGE VTEYDDAIRE VYAMGGAASL NTTKRTPHQT VQGMFWAYDG AKLIGTPPRL  300
YNQIIRKIAV AYKQEDNLAE SEINNADFAR LLALVNAVAMA DAGIFSWKEK WQFEFWRPLS  360
GVRADSLRDP KLVDRGDPFW LTLGAPATNS DSLPFKPPFP AYPSGHATFG GAAFQMVRKY  420
YNGRPGLGSW ADDEPDNIAV EFVSEELNGI SRDLRQPHDP KRDITDQPGT VRTRLPRHFS  480
SCWEMMFENA VSRIFLGVHW RFDAAAAKDI LVPTTKKDVY AVDDKGASLF KNVEDIRYRT  540
KSTREGFEGK YPIGGVPLGI EIANEIFDNG LVPTPPELQP VVQGMPQPTP QPPQHQGPPR  600
```

```
KMEKLPKPKD EDQVPMMDVE P                                              621

SEQ ID NO: 24           moltype = AA  length = 635
FEATURE                 Location/Qualifiers
source                  1..635
                        mol_type = protein
                        organism = Naegleria gruberi
SEQUENCE: 24
MMFFMMILFM ASLSHAYSPT TETDPDEYDT QFSLSLVSNT LGSIEPGPVT RYPDAYEKAT      60
SFFRNQYGLD ISADGSRLPV GAQLVTGSAS AYVMNYAKVR GYPILAGSQD VGVHDDTISI     120
VLSQPAVVHG AYGGKNGTFV DGNSVLIFGF YTFFWKVNGT SVFPRSTFAG MMPMKIGPDG     180
SMVVDCELTS NIFGKGMARG IMLIRINPLT GQPYTTIVSS HTYQMSKTDT SPKCAVLTTE     240
KDIHNDDFVV KWNNVLLSVI RDLKVAPPIA SRQMAILHTA IDDALGNCRR LRYTSRKCTR     300
ATLVSVISYA AHRVLSNLYP AQIDCFNGAL KRALECNECK TVPRTELVAI GKSGSLAADR     360
VLRCRDNDGS TDFVDYNFSN GPMSYQSHAP NYVRVPLLPQ WPNVEPFGVQ DVDSFDQGPP     420
PQIGTPAFES SYDEVFTYGK NDSSVRTFEQ RRIALFWADN AGTSTPPGHW NIILQSIIRK     480
MNIVDTFKIS GMFKVLTSSL ADAAIVCWYH KYKYDAFRPV TAIANRNRNT NWFPFLATPP     540
FPEYSSGHST FSAAGARALS LLLGTDDISF ETISEGYVHH VRQFSKLSDA AKEAGKSRIY     600
GGIHFEYANQ AGYTSGVAVA NAVYNQLCRN GSCLV                               635

SEQ ID NO: 25           moltype = AA  length = 642
FEATURE                 Location/Qualifiers
source                  1..642
                        mol_type = protein
                        organism = Naegleria gruberi
SEQUENCE: 25
MSIPLTRLLL VFTLIFSPFL LINAYSPTTE TNPQEYDAQF HLSILADGIQ AGNIAPITRY      60
PDAHEKATNF YRNQYGLDVS DNGARLPDGA QFFTSVGDQY VVHYAKVRGY PNLAGSQDLG     120
VYDDAFAIML TKPLVVHGAY GGKNGTWVDT GSILPFGFYT YFWKVNGSIA FPRITWSSPM     180
PMRISADGSL VVDCELSSNI WGKGMARGLN LIRINPVTNQ YYVSVVSSHT FPISQTDIAP     240
KCAAITTEKD IFNEDFIVKW NNVLLSTVRD FKVAPPIASR AMAILHTATD DALGSCRRSR     300
NSNKACDYAT IATTISFSAH RVLSQLFPNN IDCYNAALKR ALQCNGCSQY DVSELTKIGK     360
SAVTTADRVL RSRDNDGSAE FVDYQFRDGA MDYQSHAPNY VRNPLLPQWP NVEPFGIQNV     420
ESFRQGPPPQ LGTPLFETSY DEVFLYGRND SSVRTFDQR IAWFWDDGAG TATPPGHWNV     480
ILQSIIRSQG ITDIFKVSAI FKLLGCTLAD AGIVSWDHKY FYNALRPVTA VNNRNRNLNW    540
FPLLATPPFP EYTSGHSTFS GAAARILSLV LGSDDISFDV VSDGYKYHTR TFNKLSDAAK    600
EAGKSRIYGG IHFEYANQAG WNSGVAVANA VYNQLCRNAS CL                      642

SEQ ID NO: 26           moltype = AA  length = 623
FEATURE                 Location/Qualifiers
source                  1..623
                        mol_type = protein
                        organism = Naegleria gruberi
SEQUENCE: 26
MMVSSYSPTT ETDPQEFDAQ FHLSYLADGI QAGDIAPITR YPDAYEKATS FYRNQYGLDI      60
SDNGSRLPPG TQFFTSVGDK YVVEYAKVRG YPTLAGSQDL GVYDDAFAIM LTQPLVVHGA     120
YGGKNGTWVD SGSVLPFGFY TYFWKVNGTT AFPRITWSSP MPMRISADGS LVVDCELTSN     180
IWGKGMARGL NLIRINPATG QYYVSVVSSH TFPVSQTDIS PKCAAITTEK DIFNEDFIIK     240
WNNVLLATVR DFKVAPPVAS RAMAIVHSAV DDALGFCRRL RYTGRPCDYA TIATTVSYAA     300
HRVLGQLFPN NIDCYTAALK SALKCNGCQE YESSELTRIG KVAILAADRV LRSRDNDGSS     360
DFVDYQFRDG PMDYQSHAPN YVRIPLLPQW SAVEPFGIQD VESFRQGPPP QIGTPAFETA     420
YDEVFLYGRN DSSVRTFDQR RISWFWDDGA GTATPPGHWN VILQSIIRSQ GITDTFKISA     480
MFKLLGCSVA DAGIVSWDHK YFYNALRPVT AVNNRNRNLN WFPLLATPPF PEYTSGHSTF     540
SGAAARILSL LLGSDDITFD VTSDGYKYHT RTFNRLSDAA KEAGKSRIYG IHFEYANQA     600
GWNSGVAVAN AVYNQLCRNG NCL                                            623

SEQ ID NO: 27           moltype = AA  length = 502
FEATURE                 Location/Qualifiers
source                  1..502
                        mol_type = protein
                        organism = Chondrus crispus
SEQUENCE: 27
MVLHVLAFIV LLFSHCVNAQ APEEPTLLQN LTIDFTPPNE LANLLFPTDV ILAETPIAIR      60
TVLVFTIQGY EVIAACDSKA LGFLGKRNAI PPHLCAPLPA AKISAFLLNR LYRSQFPLEG     120
RNLEAFLIRQ GLDPTSDSTD PTTEIGIANA MAMDLVAYLE TDGWNSLGDL SRDHFRQQYS     180
DYTGFKPQNH AELDVSRLRR PLRWQPLKQE ADRRGRFTSQ VHVAPHIGRA KPLVLSREEF     240
LSRKSESPYA SADRKKTIGA KDKRTMRRLL REVLKLNRDL TKEQIAQAHW WDNKFLSLGS     300
FIAFYQGVYG FSLVDPIVIA LGEVMAQHDS VMLAWKEKLR HQLVRPPTML RRLFEGKKIR     360
AFKSLDEGVG LVRAEEWEPI VPIQPHSEYP SASALICQAT MDHLHAALTN FIKVNGTIAA     420
YETDIFPFGR SPLTENVVKV KYETLQAAALN CGKSRLYAGV HFSPSVDAGF ELGKGIGAVA   480
QKHAQDLWEG RIPDNCERCS DA                                            502

SEQ ID NO: 28           moltype = AA  length = 505
FEATURE                 Location/Qualifiers
source                  1..505
                        mol_type = protein
                        organism = Chondrus crispus
SEQUENCE: 28
MVLHAFAFLV LLFFHHVSAQ APEEPTLLQN LTVLGAGSGP PNEFANLLFP SNIIGIETPI      60
```

```
AIRLVLVVTI PFYEVIAACD SKALGFLGKR NVIPPHLCAP LPFAKISAFL LNRLYRSQFP     120
LEGRNLEAFL IRQGLDPTSD STDPTTEIGI ANAMAMDLLA YLETDGWNSL GDLSRDHFRQ     180
QYSDYTGFKP QNHAELDFSR LRRPLRWQPL KQEADHRGRF TSQVHVVPHI GRAKPLVLSR     240
EEFLSRKSES PYASADRKKT IGAKDKRTMR RLLREVLKLN RDLTKEQIAQ AHWWDNKFLS     300
LGSFIAFYQG VYGFSDTKLV VIGLGEVMAQ HDSVMLAWKE KLRHDLVRPP TMLRRLFEGK     360
KIRAFKSLDE GVGLVKAEEW EPIVPIQPHS EYPSASALIC QASMDHLHAA LTNFIKVNGT     420
IAAYETDIFP FGRSPLTENV KVKYETLQAA ALTCGKSRLY AGVHFSPSVD VGFELGKGIG     480
AVAQKHAQDL WEGRVPENCE RCSEA                                         505

SEQ ID NO: 29            moltype = AA   length = 666
FEATURE                  Location/Qualifiers
source                   1..666
                         mol_type = protein
                         organism = Chondrus crispus
SEQUENCE: 29
MATPCFAQAP APTLRRSPRR LPLTPTSFLP RPFLPKPFPR SPRHPHPRLN AASARTSAAQ     60
PPDRAATPCA TRQQQALELR RAAAQLAHDR AHPAHVSNGS EELHLHPKTG APLLLANFTK    120
GLPHERDTGL AADAAHYDLF VAAVHSGLPD DIRAIPLGPQ AAPGVRLPRS LRFRSGIARS    180
SHLFPHTDVR AWESMAAGNA FDLQGPDAQA VTMPPAPALA SPELALEMTE NYWMALLRDV    240
RFSQFAADPT VAAAMESMNA TEWVALACGD ASAVAEEERK RLRGPFTAQN VFRGNTQGDC    300
KGPYISQFLL SGSAGLGQVN SGADGYIQYG AMRMDQRVRV ALEGLDYMTT WESWLDVQNG    360
ADLRGRELYE DGERFRFICT PRDLATYVHY DALYQAYLNA CIIMLNKKIP FDKGLPFQKD    420
DDDIDKQQGFA LFGPPHILTL CTEVATRALK GIRFQKYNVH RRLRPEAVGG RVERYHHNCE    480
DPLFADVKPL YDALDKDMLE RVAAHNAEQN AKDDFGNSRF EDYSPTGSSG RTYLLPMAFP    540
EGSPMHPAYG AGHAAVAGAC TTILKAFFDH EHELDFAYVP TADGSKLEDV VDSLGEKLTV    600
EGELNKVCSN ISVGRNWAGV HYFTDYRESI ILGEKIALGL LEEQKLTYAE EFSMTIPLFD    660
GSTVTI                                                              666

SEQ ID NO: 30            moltype = AA   length = 535
FEATURE                  Location/Qualifiers
source                   1..535
                         mol_type = protein
                         organism = Chondrus crispus
SEQUENCE: 30
MRAALFTALT CSALLILGAA LAVDAPPGRK TPNAIDRESG VLASLVFPEI FDRIVVDGLE     60
TPIQFRGTTY LNIAAWNAWC NYHPTAADIF NRTRFRRPAS EHTRDNKNVA VLYALFRLYE    120
ASPVSFGGNS GIPVFSALLE REGLNPNDRS TDMNTPVGIG NRAGRDTARL MAIDGWNAEG    180
DIAGTPAQYR QPFADYTGYT PKNSPWKISH PFRWQPLLES NGRGFFFRQK NVVPFAGRTI    240
AFGLTRSEVR ARRAPAPFKR GGATVKTALK SDVAALRRHA RKVLATFAAL TTEQRVLAEY    300
FDNKGKAFRT EDNPAGLPGI ATALRFGILG PANHWNLDDD MVYGLGGAVA TLDSMVTAWK    360
EKRRVDAVRP TGQTMEFLFG ERKVKVWGGP GKKAVRIRAG DWQPYIRTMP HQEFSSGSSC    420
TCSALVEHAK LNAPREDLPF GITVPKGSSK FYPGQVPEKD TRIEFKNLSE WSELCGVSRL    480
YAGVHFEPSI QAGVDVCKGI GESSQKFAEG LRDGRLMGKW MTWFPEDTEK FWEEE          535

SEQ ID NO: 31            moltype = AA   length = 399
FEATURE                  Location/Qualifiers
source                   1..399
                         mol_type = protein
                         organism = Chondrus crispus
SEQUENCE: 31
MMREMGYDPN DQSMDLTTAV GIGNRAGRDT ARLMRDGWN GEGDISGTPK GYRQPFLDYT      60
NYIPKNTPWR LRYPFRWQPL LENNGRGFFF RQESVTPYAG SAIAFSLTPE EVKRRKVPSP    120
YKKGSVQAKN ALPEDIKTLK RNAKEVLEVS RKLTEMQMIY AELFDNKAKA FRTKENPFGL    180
GGIATAIRFS VLAPALDWNL DEEMIYGLGA NIATFDSMVT AWKEKRRVDG VRPTGQTMEY    240
LFGEKQFSVW GGPGRRPVKI RAGDWSPFIR TMPHAEFPSG SSCACTAVVE HALINTKNRD    300
DFPFRFTVPK GSSKFYPGQL PSRDTDVEIK TLSEWAQLCG ESRLYAGVHF KPSIQAGSDL    360
CKGIAQSAQE LTDKLVAGSL DAKWMKWLPE GADRFWETE                          399

SEQ ID NO: 32            moltype = AA   length = 532
FEATURE                  Location/Qualifiers
source                   1..532
                         mol_type = protein
                         organism = Chondrus crispus
SEQUENCE: 32
MRAALFTALT LLILGAALAV DAPPGRKTPN AIDRESGVLA SLVFPEVFDR IVVDGLETPI     60
QFRATTYLNI AAWNAWCNYH PTAADIFNRT RFRRPASEHT RDNKNVAVLY ALFRLYEASP    120
VSFGGNSGIP VFSALLEREG LNPNDRSTDM STPVGIGNRA GRDTARLMAI DGWNAEGDIA    180
GTPAQYRQPF ADYTGYTPKN SPWKISHPFR WQPLLESNGR GFFFRQENVV PFAGRTIAFG    240
LTRSEVRARR APAPFKRGGA TVKTALKSDV AALRRHARKV LATSAALTTE QRVLAEYFDN    300
KGKAFRTEDN PAGLPGIATA LRFGILGPAN DWNLDDDMVY GLGGAVATLD SMVTAWKEKR    360
RVDAVRPTGQ TMEFLFGERK VKVWGGPGKK AVRIRAGDWQ PYIRTMPHQE FPSGSSCTCS    420
ALVEHAKLNA PREDLPFGIT VPKGSSKFYP GQVPEKDTRI EFKNLSEWSE LCGVSRLYAG    480
VHFEPSIQAG VDVCKGIGES SQKFAEELRD GRLMGKWMTW LPEDTEKFWE EE             532

SEQ ID NO: 33            moltype = AA   length = 518
FEATURE                  Location/Qualifiers
source                   1..518
                         mol_type = protein
                         organism = Chondrus crispus
```

```
SEQUENCE: 33
MLLLGVALAQ NVTENTRDRE SSVFGYVAFP RVFDGVLVDN LETPVQFRGI LYLSFAAWNA    60
WCNYHPTAVD MFGRDKFKRP AEEHTRDNKN VAVLYSLYRV YQASPHSFGG AQGLPLYRQM   120
MREMGYDPND QSMDLTTAVG IGNRAGRDTA RLMRMDGWNG EGDISGTPKG YRQPFLDYTN   180
YIPKNTPWRL RYPFRWQPLL ENNGRGFFFR QESVTPYAGS AIAFSLTPEE VKRRKVPSPY   240
KKGSVQAKNA LPEDIKTLKR NAKEVLEVSR KLTEMQMIYA ELFDNKAKAF RTKENPFGLG   300
GIATAIRFSV LAPALDWNLD EEMIYGLGAN IATFDSMVTA WKEKRRVDGV RPTGQTMEYL   360
FGEKQFSVWG GPGRRPVKIR AGDWSPFIRT MPHAEFPSGS SCACTAVVEH ALINTKNRDD   420
FPFRFTVPKG SSKFYPGQLP SRDTDVEIKT LSEWAQLCGE SRLYAGVHFK PSIQAGSDLC   480
KGIAQSAQEL TDKLVAGSLD AKWMKWLPEG ADRFWETE                          518

SEQ ID NO: 34           moltype = AA  length = 656
FEATURE                 Location/Qualifiers
source                  1..656
                        mol_type = protein
                        organism = Chondrus crispus
SEQUENCE: 34
MHLAALKLPH DIPSPAGTHR ANSAKSLRDL CTDIARHRAH AASESNGEEA DFASACYPTN    60
FTKGLAHNNF GLVAQAEDYR VFVEAINSPA PGLFDSHVKS AEDREVAFKC RVKGAKPKWR   120
GWESPRAGHV YELQGPDAGS LGMAPAPRVG SSELSAEMAE VYAMALLRDV PFKDICAGKS   180
KEKFCEKDGD AAFSGTEIAN LLNSIGLNQY ERNRRFARTQ EDTAPYVAPL SAQTLFRGST   240
PGALVGPYIS QFMLIGARSI AGDGNGQSNF PAKEAAFDLN DGFIPYGSLI IDQRTISHKG   300
CLDHMTNWAH WLDVQNGANL AKTDCWEPER RFITTPRDLA TYVHFDALYE AYLNAALILI   360
AMESPPSKGF PERSPSGRRT PFATFGGPHI LSLVTEVATR CLKAVRRQKF NYHRRARPEV   420
MGARLTLAEY IRQAIIEHNE SQNRPDMVEM RAKCGLTCND LHAFEGYDPK CNLLLPMAFP   480
EGSPMHPAYG AGHATVAGGC VTILKAFFEM FEDCDAGKER ELCDSKGMPI AFVPTSDGTK   540
LMKDAKTKEP LTIQGELDKL AANISIGRNM AGVHYYSDYY DSLRMGERVA VGILLEQAPT   600
YGDPVEMTFR SFDGDLIRVS GQAESAPTLT ILDRNGSRVS VDDWWLRHVV GEEVIL       656

SEQ ID NO: 35           moltype = AA  length = 607
FEATURE                 Location/Qualifiers
source                  1..607
                        mol_type = protein
                        organism = Chondrus crispus
SEQUENCE: 35
MSAARRQEAF QTRVRAARLA RDRDHQVFEP NGEEDRYFRP NSQIFSYLGS YTKGLPHNRR    60
TALITSPNHF VRFVRAIDSG EPADFIKVPL GPRPALQFES EEECRAANLF KSGIAGRNNT   120
FPSSCLRAWE SMGAGLVFDL EGPDAQAVGM PPAPTLDSDE LVAEISEVYW MALLRDVRFT   180
DFTNPGPIGR AINTLNKTAW IRAARDPPDS LTPQERARLR GPFNPSNIFR GTLPGDDVGP   240
YLSQFLLVGT KGIGGAQDMA DGFISYGAHR IDQRVRHARK ELDYMTSWEA FLDVQNGADV   300
TGRDTFESGS DAFRFITTPR DLATYVHFDA LYQAYLNACL IMLDSGVRFD KGIPFGEPDF   360
KDHQRGFAHF GGPHILSLVT EVATRALKAV RFQKFNTHRR LRPEAVGGLI ERFNSNPDDP   420
QFQDVKPLFE ALDEDMMRRV ARHNREQNQG SDFGMPRADD FNPAGDTLET MLLPMAFPEG   480
SPMHPSYGAG HATVAGACVT VLKAFFQHDT ELDCFVPSD DGSRLVDASH NMNKKLTVEG   540
ELNKVCSNIS IGRNWAGVHY FTDYIESILL GEQIALGILE EQMLTFPETF TMTVPLFSGE   600
LKVLRST                                                           607

SEQ ID NO: 36           moltype = AA  length = 528
FEATURE                 Location/Qualifiers
source                  1..528
                        mol_type = protein
                        organism = Chondrus crispus
SEQUENCE: 36
MNNLISFSLL IALTIAQAIA ECVQPTGISN PSAYAALPPN SPSPADAVFF KHILLARVEI    60
AKREPPIQFY YVQNIVSTLY NTMGSFEELA LDAWGNDQPV RFCNDSSNFA LYRSVALAYI   120
THMCFSNSFP ELRAEFDSLV TPWGINPKLC TDSSKPNACG DINTPWGLAF LRYRQFLDWT   180
SRDGWNRDGA ISREYNRIPF QDWTQDPYVP ENTPWELKKK ENWQPLMEDN NIGFLFYQEH   240
VTAHIGQYGR SLYVDDEDYC SAEAPKPKYK YDEELRELIR RSAAMAQDDV AKAKVQIFDN   300
KFSSLVFLQI DLLFANGFHA DSWKFIEADT ISAAALYESL MLVWKEKIAH DACRPPSRMV   360
RDLAGQKIFA YAGANQGKKQ MRAEDWEPYI RTMPHSEYPS GSACFCAVFA ESMKLFFGSD   420
NFLANGKPSP LSLKVAAGQS LVEPGRPSAD VTLVYNSWSA VAEDCGKSRL TGGMHFTASV   480
PAGAALCAPF GRRMFDVIKA LSSGRKEGFI QDFEKPLQME SRCRKRRR              528

SEQ ID NO: 37           moltype = AA  length = 495
FEATURE                 Location/Qualifiers
source                  1..495
                        mol_type = protein
                        organism = Chondrus crispus
SEQUENCE: 37
MKCKVSLFLS LLLLSTAFTG AAGQNTTATA PTLAEVLTIS AAPTNEAVRA LFPPSILFAQ    60
TPIAVRYSLF TFVGEYEAAA ACDPVALSFL GTKDPIPPRL CTPDNAAIIQ SYISLHLVSS   120
EFPVEGRRYA AFLARVGLQP FSMSTDETTA EGWARRSAQR LEAHFKSDGW NSLGDATRAD   180
FRNPFEDSIN YRPRNPAHLS PDALRFPLRW QPLPFSVDGR GNYAHQRHVT PHLSRRVAPL   240
GLSRRAFRAA RVEGPYATPD RRGSLSRGDE RVARALLRDM LAATRGLSEE QRAVIAFWDN   300
KFFSLASFAF FYARXLAWKE KVRHDLVRPA TLVRRLLRGG RVRAWRGAGR GEGGVRAEEW   360
QAAIPVQPHS EFPSASAVLC TAVLEHLQEV LGEVVGGNTT MVPYEVTVTP GVNPLNPARV   420
VVGIRFDSLG EAARSCGVSR LWAGLHFRPA VEAGFTLGKG TGRAAYLHLK DLAEGRVPKN   480
CARCVGRGGA TSSDE                                                  495
```

```
SEQ ID NO: 38            moltype = AA  length = 510
FEATURE                  Location/Qualifiers
source                   1..510
                         mol_type = protein
                         organism = Chondrus crispus
SEQUENCE: 38
MVLHVLAFIV LLFSHCVNAQ APEEPTLLQN LTIDFTPLNE YANVLFPVDV VSMETPIAIR    60
YVLVFTIPFY EVFAACDSKA LGFLGKRNVI LPHLCEPLSI AKTTAFLMSR LYRSQFPLEG   120
RNLEAFLIRQ GLDPTSDSTD PTTEIGIANA MAVDLVAYLE TDGWNSLGDL SRDHFRQQYS   180
DYTGFKPQNH AELDVSRLRR PLRWQLRRPL RWQPLKQEAD RRGRFTSQVH VVPHIGRAKP   240
LVLSREEFLS RTSESPYASA DRKKTIGAKD KRTMRRLLRE VLKLNRDLTK EQIAQAHWWD   300
NKFLSLGSFI TFYQGVYGFN NADAAVLGLG EVMAQHDSVM LAWKEKLRHD LVRPPTMLRR   360
LFEGKKIRAF KSLDEGVGLV RAEEWEPIVP IQPHSEYPSA SALICQASLD HLHAALTNFI   420
KVNGTIAAYE TDIVPFLRSP LTENVKVKYE TLQAAALTCG KSRLYAGVHF SPSVDVGFKL   480
GQGIGAVAQK HIQDLWEGRI PENCERCSNV                                   510

SEQ ID NO: 39            moltype = AA  length = 631
FEATURE                  Location/Qualifiers
source                   1..631
                         mol_type = protein
                         organism = Chondrus crispus
SEQUENCE: 39
MSDMSTEISP RQQEAYDIRV AAATLALARD RKRKVFEPNG EEDRYFRPNS QILSYLGSYT    60
KGLPHNRSTA LVTSPNHFVR FVQAIDSGEP ADFIKVPLGP RPALEFTTEE ECIAANLFKS   120
GIATRNDSFD PACLRAWESM GAGLVFDLEG PDAQAVGMPP APTLDSDELV AEISELYWMA   180
LLRDVRFTDF TNPGPIRRAI NTLNRTTWIR AARDPPDSLT PQERARLRGP FNPSSIFRGT   240
LPGDDVGPYL SQFLLVGTEG IGGAQDRADG FISYGAHRID QRVRHATKEL DYMTSWEAFL   300
DVQNGADVAG RDTFESGSDA FRFITTPRDL ATYVHFDALY QAYLNACLIL LDNKVKFDQG   360
IPMGEPDFNG NQGIPFQDPD FKDHQRGFAH FGGPHILSLV TEVATRALKA VRFQKFNTHR   420
RLRPEAVGGL IERFNSNPDD PQFQDVKPLF EALDEDMLRR VASHNREQNE RSDFGMPRAD   480
DFNPAGDTLE TMLLPMAFPE GSPMHPSYGA GHATVAGACV TVLKAFFQHD ATLDFCYVPS   540
DDGSRLDDAS HTLNKKLTVE GELNKVCSNI SIGRNWAGVH YFTDYIESIL LGEQIALGIL   600
EEQMLTFPET FTMTVPLFSG GFRTLISTSD P                                 631

SEQ ID NO: 40            moltype = AA  length = 598
FEATURE                  Location/Qualifiers
source                   1..598
                         mol_type = protein
                         organism = Corallina officinalis
SEQUENCE: 40
MGIPADNLQS RAKASFDTRV SAAELALARG VVPSLANGEE LLYRNPDPEN GDPSFIVSFT    60
KGLPHDDNGA IIDPDDFLAF VRAINSGDEK EIADLTLGPD RDPDTGLPIW RSDLANSLEL   120
EVRGWENSSA GLTFDLEGPD AQSIAMPPAP VLTSPELIAE IAELYLMALG REIEFSEFDS   180
PKNAEYIQFA IDQLNGLEWF NTPAMLGDPP AEIRRRRGEV TVGNLFRGIL PGSEVGPYLS   240
QYIIVGSKQI GSATGGNKTL VSPNAADEFD GEIAYGSITI SQRVRIATPG RDFMTDLKVF   300
LDVQDAADFR GFESYEPGAR LIRTIRDLAT WVHFDALYEA YLNACLILLA NRVPFDPNIP   360
FQQEDKLDNQ DVFVNFGDAH VLSLVTEVAT RALKAVRYQK FNIHRRLRPE ATGGLISVNK   420
IAAEKGESVF PEVDLAVEEL EDILEKAEIS NRKQNIADGD PDPDPSFLLP QAFAEGSPFH   480
PSYGSGHAVV AGACVTILKA FFDSNFQIDQ VFEVDKDEDK LVKSSFKGTL TVAGELNKLA   540
DNIAIGRNMA GVHYFSDQFE SILLGEQVAI GILEEQSLTY GENFFFNLPK FDGTTIQI    598

SEQ ID NO: 41            moltype = AA  length = 597
FEATURE                  Location/Qualifiers
source                   1..597
                         mol_type = protein
                         organism = Corallina pilulifera
SEQUENCE: 41
MGIPADNLQS RAKASFDTRV AAAELALARG VVPSFANGEE LLYRNCETGD PSFIASFTKG    60
LPHDDNGAII DPDDFLAFVR AINSGDEKEI ADLTLGPARD PETGLPIWRS DLANSLELEV   120
RGWENSSAGL TFDLEGPDAQ SVAMPPAPVL MSPELIAEMA ELYLMALGRD IEFSEFESPK   180
NAAFIRSAIE RLNGLEWFNT PAKLGDPPAE IRRRRGEVTV GNLFRGILPG SEVGPYLSQY   240
IIVGSKQIGS ATVGNKTFVS PNAADEFDGE IAYGSITISQ RVRIATPGRD FMTDLKVFLD   300
VQDGADFRGF ESYEPGARLI RTIRDLATWV HFDALYEAYL NACLILLANG VPDPNLPFQ    360
QEDKLDNHDV FVNFGSAHVL SLVTEVATRA LKAVRYQKFN IHRRLRPEAT GGLISVNKKS   420
FLAGSDIIFP EVSELVEELS SILDDVAESN EKQNRADGIV SPDKSFLLPM AFAEGSPFHP   480
SYGSGHAVVA GACVTILKAF FDANFQIDKV FEVDTDEDKL VKSSFKGTLT VAGELNKLAD   540
NVAIGRNMAG VHYFSDQFES LLLGEQIAIG ILEEQSLTYG ENFFFNLPKF DGTTIQI     597

SEQ ID NO: 42            moltype = AA  length = 598
FEATURE                  Location/Qualifiers
source                   1..598
                         mol_type = protein
                         organism = Corallina pilulifera
SEQUENCE: 42
MGIPADNLQS RAKASFDTRV AAAELALNRG VVPSFANGEE LLYRNPDPDN TDPSFIASFT    60
KGLPHDDNGA IIDPDDFLAF VRAINSGDEK EIADLTLGPA RDPETGLPIW RSDLANSLEL   120
EVRGWENSSA GLTFDLEGPD AQSIAMPPAP VLTSPELVAE IAELYLMALG REIEFSEFDS   180
PKNAEYIQFA IDQLNGLEWF NTPAKLGDPP AEIRRRRGEV TVGNLFRGIL PGSEVGPYLS   240
QYIIVGSKQI GSATVGNKTL VSPNAADEFD GEIAYGSITI SQRVRIATPG RDFMTDLKVF   300
```

```
LDVQDAADFR GFESYEPGAR LIRTIRDLAT WVHFDALYEA YLNACLILLA NGVPFDPNLP    360
FQQEDKLDNQ DVFVNFGSAH VLSLVTEVAT RALKAVRYQK FNIHRRLRPE ATGGLISVNK    420
IAPQKGESIF PEVDLAVEEL GDILEKAEIS NRKQNIADGD PDPDPSFLLP MAFAEGSPFH    480
PSYGSGHAVV AGACVTILKA FFDSGIEIDQ VFEVDKDEDK LVKSSFKGTL TVAGELNKLA    540
DNIAIGRNMA GVHYFSDQFE SLLLGEQVAI GILEEQSLTY GENFFFNLPK FDGTTIQI     598

SEQ ID NO: 43           moltype = AA   length = 605
FEATURE                 Location/Qualifiers
source                  1..605
                        mol_type = protein
                        organism = Gracilaria changii
SEQUENCE: 43
MASHIPRFTK AYAVREQAAL MAKSRPHPLH VSNNEELRYR IPTSGEPSHI GSYTKGLPHD     60
RNTGVLSNPD DFQSFIRAMD AGDQFSIRDV PLGPQNEQQA FQSGIAKGVS ARAWESMAAG    120
LTYDLEGPDA QSVTMPPAPA LDSDELLTEV TELYWMALLR DVPFSEFNGD KNNDIQEAVD    180
SLNSTPWVQI AKNGVVPTTL TDAERVRLRG PFTVDNVFRG TTRGDRDGPY LSQFMLIGNT    240
GIGNGNRIED GFIRYGAHRV DQRVRVAEMG RDFMTTWSAF VDVQNGADVR GREVYNNDVR    300
YRFISTPRDL ATYVHFDALY QAYLNACLIL LGMRVPFDKG LPFQREDDID HQQTFATFGA    360
PHILSLVTEV ATRALKAVRF QKFNVHRRLR PEAVGGLLHR YMQETTNDLY RGAKQLAENL    420
DANLLDKVKR HNAKQNMKSD GDAPRANDLG ECEDADEITL LPMAFPEGSP MHPSYGAGHA    480
TVAGACVTIL KAFFDHGYEL RMLDEDGETM IPFAFVPTAD GSGLENRIGE YRNLTALTVE    540
GELNKVCSNI CIGRNWGGVH YFSDYRESIR VGEQVAIGLL EEQKLTYGEN FSMTVPLFDG    600
SVHRI                                                                605

SEQ ID NO: 44           moltype = AA   length = 641
FEATURE                 Location/Qualifiers
source                  1..641
                        mol_type = protein
                        organism = Ascophyllum nodosum
SEQUENCE: 44
MMKASGGIIT ALLAAFPPCL SQTVNELADM QTRPLLSGSV CRVRDTVDFL SPTKRAKITF     60
KRRIGIAAGE LAVGPTCHLN NGDEANVPLF DGQFHKSLPH DDVGRVNPEA YQLLLDCIES    120
NDINVCDQVP SGVESDGRKL VNPLGGGHQ VDGADSDNIF IKQPDNLLSE RLAAQQAEVY    180
WMALLRDIPF SQFGTNNTVQ MAAANLQGFD AFNGLSISRD ADGNIDPMQD LPFRTDWPGVS    240
SGPMVSQFML ANFDIDGIVV EPKAKTLVPE MEYMTGVDTW LNIQNGGPPE DTLFVDEPLF    300
IRNGRDLAAL SFNDVLYTEA FRTILILFNE SILAEAGPYG SSTRQEGFTT LGTSHYIHAM    360
AAGSSSTRHA WYAKWQVHRV LRPEAYGGLL HFVINNLIDD VPLPASIVSN TELLNAVESL    420
NQAQNGGTNQ VFLLPMAVGE GSPVHPAYPS GHAINLGAYL TVLKAFLGFE LGQRCFPSPM    480
ISNDAGTDRI PFVPSDGDRV GTCINEDGEE EVGLTYEGEL NKVTSNVAIG RSHLGVHWRM    540
DGVFGAEMGE AGAIRRLQQE LGGGLPEARDT EGPIPPASYK FRLYSGTMIE LFPDNRYMLG    600
DQMCKGFFTG DDFCVPADEE ETAELEDLVL GSVVDQTCAE L                        641

SEQ ID NO: 45           moltype = AA   length = 557
FEATURE                 Location/Qualifiers
source                  1..557
                        mol_type = protein
                        organism = Ascophyllum nodosum
SEQUENCE: 45
QTCSTSDDAD DPTPPNERDD EAFASRVAAA KRELEGTGTV CQINNGETDL AAKFHKSLPH     60
DDLGQVDADA FAALEDCILN GDLSICEDVP VGNSEGDPVG RLVNPTAAFA IDISGPAFSA    120
TTIPPVPTLP SPELAAQLAE VYWMALARDV PFMQYGTDDI TVTAAANLAG MEGEFPNLDAV    180
SIGSDGTVDP LSQLFRATFV GVETGPFISQ LLVNSFTIDS ITVEPKQETF APDVNYMVDF    240
DEWLNIQNGG PPAGPELLDD ELRFVRNARD LARVFTDNI NTEAYRGALI LLGLDAFNRA    300
GVNGPFIDID RQAGFVNFGI SHYFRLIGAA ELAQRSSWYQ KWQVHRFARP EALGGTLHLT    360
IKGELNAFDF DLSLLENAELL KRVAAINAAQ NPNNEVTVLL PQAIQEGSPT HPSYPSGHAT    420
QNGAFATVLK ALIGLDRGGD CYPDPVYPDD DGLKLIDFRG SCLTFEGEIN KLAVNVAFGR    480
QMLGIHYRFD GIQGLLLGET ITVRTLHQEL MTFAEESTFE FRLFTGEVIK LFQDGTFTID    540
GFKCPGLVYT GVENCVS                                                   557

SEQ ID NO: 46           moltype = AA   length = 642
FEATURE                 Location/Qualifiers
source                  1..642
                        mol_type = protein
                        organism = Ectocarpus siliculosus
SEQUENCE: 46
MKAFVGIAAL LAASPPCLGA TSNEEHQPTH PLLSGSVCRV RDSLDFLSPT ERAKVTLQKR     60
VDTAKEEFQV GPTCHITNGD ETNVPDFIGQ FHKSLPHDKF GTVSKTSYQK LLDCVFSADV    120
NVCDVPSGA SARGAKMINP LGGTAHQVDG ADSDNVFITT PDGVLSEELA AQMAEVYWMA    180
LTRDIPFSEF ATNSLVRAAA ENLERLPAFK GLNIPKSAGG KIDPVQDLFR TDWPGVTAGP    240
VVSQLLLSDF AIDNIVVPPK QVTLVKEMDY MTTFQDWLDV QNGASKVKTE FVDEDKPLFI    300
RNGRDLAALA FTDLLYTEAF RAALVMFRQG ILSSAEGPYS TSERQVGFAT FGEPHILTSL    360
AASSSSTRHA WYAKWQVHRV LRPEAYGGLV HNTLTGRLHT PLPKAILQNT ELLNRVRTHN    420
AKCNGDGKGG HGDGTYLLPM AVAEGSPVHP AYPSGHAINL GAYITTLKAF LGFELGQRCY    480
LGDLVVSNDE GTKRIEYVPR KGETCIDQNG REVQGLTYEG ELNKVASNVI IGRSHIGVHY    540
RMDGVYGALM GETSAVRRLQ QELPNLSEAR DTKGSIPPAS YKFRLYSGKV LELLAKDIFK    600
LDGRTCKGLY TGDDFCDEHQ DGGHYLEHLV NKGGDFAFHV EL                       642

SEQ ID NO: 47           moltype = AA   length = 676
FEATURE                 Location/Qualifiers
```

```
source                  1..676
                        mol_type = protein
                        organism = Fucus distichus
SEQUENCE: 47
MLCHAADTTR GSPMPDTGVL RLLTSEQRAK GWRRQLEGEK SLGFHPSETP YIKYLEGSET    60
WKKVKLPTDG ISASKILGKI MARVRIATAL AVVLAAPCLA FDEVTASGVF PEEHKHTGEG   120
RHLQTCTNSD DALDPTAPNR RDNVAFASRR DAARRERDGT GTVCQITNGE TDLATMFHKS   180
LPHDELGQVT ADDFAILEDC ILNGDFSICE DVPAGDPAGR LVNPTAAFAI DISGPAFSAT   240
TIPPVPTLSS PELAAQLAEL YWMALARDVP FMQYGTDEIT TTAAANLAGM GGFPNLDAVS   300
IGSDGTVDPF SQLFRATFVG VETGPFVSQL LVNSFTIDAI TVEPKQETFA PDLNYMVDFD   360
EWLNIQNGGP PAGPEELDEE LRFIRNARDL ARVSFVDNIN TEAYRGSLIL LELGAFSRPG   420
INGPFIDSDR QAGFVNFGTS HYFRLIGAAE LAQRASCYQK WQVHRFARPE ALGGTLHNTI   480
AGDLDADFDI SLLENDELLK RVAEINAAQN PNNEVTYLLP QAIQVGSPTH PSYPSGHATQ   540
NGAFATVLKA LIGLDRGGEC FPNPVFPSDD GLELINFEGA CLTYEGEINK LAVNVAFGRQ   600
MLGIHYRFDG IQGLLLGETI TVRTLHQELM TFAEEATFEF RLFTGEVIKL FQDGTFSIDG   660
DMCSGLVYTG VADCQA                                                  676

SEQ ID NO: 48           moltype = AA length = 624
FEATURE                 Location/Qualifiers
source                  1..624
                        mol_type = protein
                        organism = Laminaria digitata
SEQUENCE: 48
MKGLAGPAGA MAVVALGLVP GGAIGKSLRQ EPSEPRLSGG VDTAASPSKD TLKGSLSRKL    60
QVVNDDALDV SGTPAERAAN ALNQRIEFAE TEFTASEGTL HLNNGDRSSA ATFHKSLPHD   120
SLGQVNSEDF DLLMECIAQG DFDTCELVPA GDDGRLSNPL GGIAVEMAGA AGPALTLPPA   180
SAINSEDLAA QMAEQYWMAL TRDVPFSQYG EDEATVAAAD NLATMPGFAD IVGVAVDPET   240
RRADPQSQLF RSSAFGVETG PFISQLLVKD FTIDSITVTP MQKTFAPGAD YMTDYDEWLS   300
IQNGGSPDSE ADLDDEDRYI RNSRDLSRLV ATDTVNTEAY RAALILLLDPD QGADGRAAIS   360
APGLNGPYAD SSRQAGFVNY GVSHLMRLVG TAELAQKSAW YQKWNVHMFV RPEAFGGSIH   420
NVLLGKLDVE IAPSLLKNTD LLDRVAARNG EINGRPGVLD RTYLLSQALP EGSPTHPSYP   480
AGHATQNGAF ATVLKALVGL ERGSVCFNDP VFPDDEGLTL LPYTGDDGNN CLTFEGEINK   540
LAVNVALGRN MLGVHWRIDS ELGLLLGETA AVRILQQEAV AYPENAGYEF RLMSGKTIRL   600
ETDGTFFIDD TLCSGDAFMG ADLC                                         624

SEQ ID NO: 49           moltype = AA length = 613
FEATURE                 Location/Qualifiers
source                  1..613
                        mol_type = protein
                        organism = Laminaria digitata
SEQUENCE: 49
MKGLAGPAGA MVVVALGLVP GGAIGKSLRQ EPSEPRLSGG VDTAVSPSKD TLKGSLSRNL    60
QVANDDALDV NGTPAERAAN ALAQRIELAE TEFAASEGLF HVNNGDRSSA ATFHKSLPHD   120
SLGQVDSAAF EALTECIAQG DFDICELVPA GDVGRLSNPL AGITVEMAGA AGSALTLPPA   180
SALDSEDLAA QMAELHWMAL TRDVPFSQYG EDEATVAAAD NLATMPGFQN MVGVAVDRDG   240
RADPQSQLFR TSAFGVETGP FISQLLVQDF TIDSITVAPI QKTFEPGADY MADYDEWLFI   300
QNGGVPHDD VLFDDVNRYI RNSRDLSRLV AADTVNTEAY RAALILLEQG AISGPGSNGP   360
YAGSSRQAGF VNYGVSHLMR LVGTAELSQK SAWYQKWNVH MFVRPEAFGG TIHNVLLGKL   420
NVDINPSLLK NTELLERVAE RNGVINGRPG VLDRTYLLSQ AVIEGSPTHP SYPAGHATQN   480
GAFATVLKAL VGLERGSDCF RDPKVPDDEG LTLLDFTGDC LTFEGEINKL AVNVAFGRNM   540
CGVHWRIDSE QGLLLGEMAA VRILQQEAVT FPENAGYEFN LMSGETIRLE TDGTFFINDR   600
LCSGDAFMGA DLC                                                     613

SEQ ID NO: 50           moltype = AA length = 645
FEATURE                 Location/Qualifiers
source                  1..645
                        mol_type = protein
                        organism = Laminaria digitata
SEQUENCE: 50
MKSFVGLTAL LAAFPPCFAA GDHDEVRATL PLLSGSVCRV RDSLDFLDPV QRATVTLEKR    60
LAIAKNEFGV GPTCHITNGD EEDVPLFAGQ YHKSLPHDKF GQVDAADYQK LLDCVFTSDI   120
NVCDKVPSGA AGGGGAKLVN PIGGTAHQTT GADSDSVFIT TPDALLSERL AAQQTEVYWM   180
ALTRDVPFNQ FGNDGLVQIA AENLAALPEF KGLSIPRNAD GTIDPVTQLF RTEWPGVTAL   240
PVVSQLMLAD FVIDSIIVPP TAVTLVPRMD YMTAFQPWLD VQNGDSDVVT EFIDPAEPLF   300
IRNGRDLANL SFNDQLYTEA FRAALILFSE SVLGGSIGPY AESLRQQGFT TFGESHILAA   360
MASSSSSTRH AWYTKWQVHR VLRPQAYGGL LHNTLMKDVI TPLPQSILGN TDLLSRVAAN   420
NIRMNPDGEK TFLLPMATAQ GSPNHPAYPS GHAINLGGYI TTLKAFVGFE AGQKCFPNLV   480
ESDDGGLARV PYVPTGTEFL EDCVDKDGNK TTGLTIEGEL NKVASNVIIG RSHLGVHWRM   540
DGVSGALMGE TSAVRRLQQE LSGLPEARVV DGARSDDIPP ATYKFRLYSG KMLEIFGVTL   600
YRLDGQLCKG AYTGDDFCNV VNEDKFETFE DIVKHSATVS VHTEL                  645

SEQ ID NO: 51           moltype = AA length = 646
FEATURE                 Location/Qualifiers
source                  1..646
                        mol_type = protein
                        organism = Laminaria digitata
SEQUENCE: 51
MKISSLGLTA LLAAFAPCLG YEEPPEPTQP LLSGNVCRVR DSLDFLDPVP RAKVTLLKRL    60
AIAKDEISVG PTCHINNGDE ENVPLFAGQY HKTLPHDKFG QVDEDAYKKL LECVFTSDIN   120
```

```
ECEKVPSGAG RRGGAKLTNP LGGTAHQVTG ADSDNVFITT PDSLLSERLA AQQAEVYWMA    180
LLRDIPFGEF AKNDYVRLAA ENLQGLPAFK GLNIPRSEGG KIDPVTDLFR TTWPGVTTGP    240
VVSQFMLSDF LIDSIKVTPK ADPLTPGVDY MTAFQPWLDV QNGASKLETT FDEENPRFIR    300
NGRDLATIAL RDQLYTEAFR AALILFTEGA LGGEVGPYAE AERQQGFATF GEPHILTAMA    360
SASSVTRHAW YAKWQVHRML RPEAYGALVH NTLMRDVITP LPDSILRNTE LLNRVEVHNQ    420
RMNPDGEKTF LLPMAAAQGS PTHPAYPSGH AINNGAYITA LKAFLGYEAG QKCFPNPVVS    480
NDEGTKRIKY KPSGREIVGE CVNEKGKLVE GLTYEGELNK ISANVLLGRS HIGVHWRMDG    540
VYGALMGETS CVRRLQQELP GLPEAREVEG KKRRGDIPPA TYKFRLYSGK ILELYGRNLY    600
KLDGKLCEGA FTGDDFCDPI DEDDYSSFDD IVEEHAQFSL HGHTEL                   646

SEQ ID NO: 52           moltype = AA  length = 416
FEATURE                 Location/Qualifiers
source                  1..416
                        mol_type = protein
                        organism = Chlamydomonas reinhardtii
SEQUENCE: 52
MHQLSAYAAL ALLALATLPS SLAVQSIVTD WLTVTQSTVI ATGIDHQTTA RLYGDVASAQ     60
YDAIKIVRDY KKTKLNEEAA VAYASHSVLS TFFHWRQSTI YDILLQQQLD KWGISDSQVP    120
LYKKLIVPTI QARLQKRIGD NFSIYANFRP AGNGTANWGK YQYTPGQTSA RYPQLAYTTA    180
NYLSAADVDE VTKEFKRFQL DDPEYARQLQ QSKDYGSVNS TVRSAYDSNS PRFWALGGGT    240
ATVAGLYVNI SIAVIPDSTP LIHQARFFKL LGSSFFDAAV ACFRIKYREL FWRPITAIRT    300
THGVGTADPT WTPLLATPAH PEYPSGHQCS SGAWTAINEA YFGALGPLNV TSYGALDISP    360
RTFPSFRSAA VECGDSRLYA GVHFNKSNVD GFNLGYKVAQ HIHTKYFAGK TFVDSI        416

SEQ ID NO: 53           moltype = AA  length = 457
FEATURE                 Location/Qualifiers
source                  1..457
                        mol_type = protein
                        organism = Coccomyxa subellipsoidea
REGION                  1..457
                        note = strain C-169
SEQUENCE: 53
MLMASALPAR AANNAVIQWQ DAVEQVVRNY NISNQISAKF YALTNIAQYQ ALLANKAQDN     60
KINDTAVTAF AAHYILSYYW PYKQNVFDGI IAKQLAGLPA SEKLAARTLA QPYAIKLIVS    120
RVNDSTQQWA DFKPASAENG PTGAYAFTPN QTFVLYPQLA NATTLATPNA NSPPSQQAGA    180
APAQYSNADT LTVGPAQTFF SSKLTQYKPL DLSSAEYAND FNTTATLGSK NSTARKEYDT    240
ETAWFWADLD GTSTVNGHYY TIAKSLLPND TSLLDTAELF ARLGSAQFDS NIVGWYIKFY    300
YLFWRPVTAI RRGDAKHPAD PTWTPLLNTP AHPEYPSTHT VTAAASGQVL ARWFKSDNVT    360
FTVGSEYAPK KLAPRTYSSF SEAAQEVGWS RIYGGIHFPK SGPDGAGVGT KVGDTVSDNF    420
PAAIDSIFGT TYAATRAANS GSTSPSPKAA TGRRLFA                            457
```